US010420856B2

(12) United States Patent
Arinzeh et al.

(10) Patent No.: US 10,420,856 B2
(45) Date of Patent: Sep. 24, 2019

(54) SCAFFOLD FOR TISSUE GROWTH AND REPAIR

(71) Applicant: New Jersey Institute of Technology, Newark, NJ (US)

(72) Inventors: Treena Arinzeh, West Orange, NJ (US); George Collins, Maplewood, NJ (US); Yee-Shuan Lee, Kearny, NJ (US)

(73) Assignee: New Jersey Institute of Technology

( * ) Notice: Subject to any disclaimer, the term of this patent is extended or adjusted under 35 U.S.C. 154(b) by 74 days.

(21) Appl. No.: 15/242,711

(22) Filed: Aug. 22, 2016

(65) Prior Publication Data

US 2016/0354515 A1 Dec. 8, 2016

Related U.S. Application Data

(60) Division of application No. 13/651,296, filed on Oct. 12, 2012, now Pat. No. 9,476,026, which is a continuation-in-part of application No. 12/661,264, filed on Mar. 12, 2010, now Pat. No. 9,334,476, which is a continuation-in-part of application No. 12/411,320, filed on Mar. 25, 2009, now abandoned.

(60) Provisional application No. 61/546,257, filed on Oct. 12, 2011, provisional application No. 61/159,751, filed on Mar. 12, 2009.

(51) Int. Cl.
| | |
|---|---|
| A61L 27/16 | (2006.01) |
| A61L 27/54 | (2006.01) |
| C12N 5/00 | (2006.01) |
| C12N 5/079 | (2010.01) |
| A61L 27/38 | (2006.01) |
| C12N 5/0775 | (2010.01) |

(52) U.S. Cl.
CPC .......... *A61L 27/16* (2013.01); *A61L 27/3834* (2013.01); *A61L 27/54* (2013.01); *C12N 5/0068* (2013.01); *C12N 5/0618* (2013.01); *C12N 5/0668* (2013.01); *A61L 2300/414* (2013.01); *A61L 2400/12* (2013.01); *A61L 2430/02* (2013.01); *A61L 2430/06* (2013.01); *C12N 2529/00* (2013.01); *C12N 2533/30* (2013.01)

(58) Field of Classification Search
None
See application file for complete search history.

(56) References Cited

U.S. PATENT DOCUMENTS

| | | | |
|---|---|---|---|
| 4,846,835 | A | 7/1989 | Grande |
| 5,030,225 | A | 7/1991 | Acbischer et al. |
| 5,250,843 | A | 10/1993 | Eichelbeger |
| 5,353,498 | A | 10/1994 | Eillion et al. |
| 5,486,359 | A | 1/1996 | Caplan |
| 5,522,879 | A | 6/1996 | Scopelianos |
| 5,626,861 | A | 5/1997 | Laurencin et al. |
| 5,666,467 | A | 9/1997 | Colak |
| 5,681,873 | A | 10/1997 | Norton et al. |
| 5,766,618 | A | 6/1998 | Laurencin et al. |
| 5,811,094 | A | 9/1998 | Caplan |
| 5,827,735 | A | 10/1998 | Young |
| 5,842,193 | A | 11/1998 | Eichelberger |
| 5,906,934 | A | 5/1999 | Grande et al. |
| 5,955,529 | A | 9/1999 | Imai et al. |
| 6,095,148 | A | 8/2000 | Shastri et al. |
| 6,165,486 | A | 12/2000 | Marra et al. |
| 6,174,333 | B1 | 1/2001 | Kadiyala |
| 6,214,369 | B1 | 4/2001 | Grande et al. |
| 6,306,424 | B1 | 10/2001 | Vyakarnam |
| 6,355,239 | B1 | 3/2002 | Bruder |
| 6,387,367 | B1 | 5/2002 | David-Sproul |
| 6,464,983 | B1 | 10/2002 | Grotendorst |
| 6,472,210 | B1 | 10/2002 | Holy et al. |
| 6,482,231 | B1 | 11/2002 | Abatangelo |
| 6,489,165 | B2 | 12/2002 | Bhatnager et al. |
| 6,511,511 | B1 | 1/2003 | Slivka et al. |
| 6,541,024 | B1 | 4/2003 | Kadiyala |
| 6,685,956 | B2 | 2/2004 | Chu |
| 6,689,166 | B2 | 2/2004 | Laurencin et al. |
| 6,689,374 | B2 | 2/2004 | Chu |
| 6,730,252 | B1 | 5/2004 | Teoh et al. |
| 6,734,478 | B2 * | 5/2004 | Johansson ............ B82Y 10/00 257/295 |
| 6,783,712 | B2 | 8/2004 | Slivka et al. |
| 6,790,455 | B2 | 9/2004 | Chu |

(Continued)

FOREIGN PATENT DOCUMENTS

| | | |
|---|---|---|
| WO | WO 2006/068809 | 6/2006 |
| WO | WO 2006/095021 A1 | 9/2006 |

(Continued)

OTHER PUBLICATIONS

Hardingham, Proteoglycans: Their Structure, Interactions and Molecular Organization in Cartilage, Biochemical Society Transactions, vol. 9, No. 6, pp. 489-497, 1981.
Davis, et al., Structural and Dielectric Investigation on the Nature of the Transition in a Copolymer of Vinylidene *Fluoride and Trifluoroethylene, Macromolecules*, 15: 329-333, 1982.
Lovinger, Ferroelectric Polymers, Science, New Series, vol. 220, No. 4602, pp. 1115-1121, 1983.
Patel, et al., Perturbation of the Direction of Neurite Growth by Pulsed and Focal Electric Fields, Journal of Neurosci, vol. 4, pp. 2939-2947, 1984.
Humphrey, et al., The Dielectric Piezoelectric and Pyroelectric Properties of VDF-TrFE Copolymers, Plessey Research (Caswell) Limited, Allen Clark Research Centre, Caswell, Towcester, Northants, NN12 8EQ, England, 1986.

(Continued)

*Primary Examiner* — Blaine Lankford
(74) *Attorney, Agent, or Firm* — McCarter & English, LLP

(57) ABSTRACT

Provided is an electroactive structure and method for growing isolated differentiable cells comprising a three dimensional matrix of fibers formed of a biocompatible synthetic piezoelectric polymeric material, wherein the matrix of fibers is seeded with the isolated differentiable cells and forms a supporting scaffold for growing the isolated differentiable cells, and wherein the matrix of fibers stimulates differentiation of the isolated differentiable cells into a mature cell phenotype on the structure.

14 Claims, 28 Drawing Sheets

(56) References Cited

U.S. PATENT DOCUMENTS

| | | | |
|---|---|---|---|
| 6,790,528 B2 | 9/2004 | Wendorff et al. | |
| 6,863,900 B2 | 3/2005 | Kadiyala | |
| 6,930,365 B2 * | 8/2005 | Bergaud | B01L 3/5085 |
| | | | 257/414 |
| 7,012,106 B2 | 3/2006 | Yuan et al. | |
| 7,022,522 B2 | 4/2006 | Guan et al. | |
| 7,247,313 B2 | 7/2007 | Roorda et al. | |
| 7,271,234 B2 | 9/2007 | Kohn et al. | |
| 7,579,070 B2 * | 8/2009 | Rockford | B32B 37/00 |
| | | | 428/316.6 |
| 7,601,525 B2 | 10/2009 | Batich et al. | |
| 7,619,901 B2 | 11/2009 | Eichelberger et al. | |
| 7,767,221 B2 | 8/2010 | Lu et al. | |
| 7,803,574 B2 | 9/2010 | Desai | |
| 2002/0004039 A1 | 1/2002 | Reid et al. | |
| 2002/0034796 A1 | 3/2002 | Shastri et al. | |
| 2002/0173213 A1 | 11/2002 | Chu et al. | |
| 2003/0054035 A1 | 3/2003 | Chu et al. | |
| 2003/0069369 A1 | 4/2003 | Belenkaya et al. | |
| 2003/0077311 A1 | 4/2003 | Vyakarnam et al. | |
| 2003/0211130 A1 | 11/2003 | Sanders et al. | |
| 2004/0018226 A1 | 1/2004 | Wnek et al. | |
| 2005/0095695 A1 | 5/2005 | Shindler et al. | |
| 2005/0196423 A1 | 9/2005 | Batich et al. | |
| 2006/0057377 A1 | 3/2006 | Harrison et al. | |
| 2006/0094320 A1 | 5/2006 | Chen et al. | |
| 2006/0128012 A1 | 6/2006 | Arinzeh et al. | |
| 2006/0198865 A1 | 9/2006 | Freyman et al. | |
| 2006/0204539 A1 | 9/2006 | Atala et al. | |
| 2006/0240064 A9 | 10/2006 | Hunter et al. | |
| 2007/0179594 A1 | 8/2007 | Llanos et al. | |
| 2007/0267725 A1 | 11/2007 | Lee et al. | |
| 2008/0009599 A1 | 1/2008 | East et al. | |
| 2008/0112150 A1 | 5/2008 | Jones | |
| 2008/0206343 A1 | 8/2008 | Edinger et al. | |
| 2008/0246126 A1 | 10/2008 | Bowles et al. | |
| 2009/0028921 A1 | 1/2009 | Arinzeh | |
| 2009/0048358 A1 | 2/2009 | Kim | |
| 2009/0325296 A1 | 12/2009 | Arinzeh et al. | |
| 2010/0078771 A1 | 4/2010 | Barth et al. | |
| 2010/0078776 A1 | 4/2010 | Barth et al. | |
| 2010/0173158 A1 | 7/2010 | Furuzono et al. | |
| 2010/0233234 A1 | 9/2010 | Arinzeh et al. | |
| 2010/0233807 A1 | 9/2010 | Arinzeh et al. | |
| 2010/0274742 A1 | 10/2010 | Hodjat et al. | |
| 2010/0324697 A1 | 12/2010 | Arinzeh et al. | |
| 2011/0300626 A1 | 12/2011 | Arinzeh | |
| 2013/0052254 A1 | 2/2013 | Arinzeh et al. | |

FOREIGN PATENT DOCUMENTS

| | | |
|---|---|---|
| WO | WO 2008/055038 A2 | 5/2008 |
| WO | WO 2008/157594 | 12/2008 |
| WO | WO 2013/023064 | 2/2013 |

OTHER PUBLICATIONS

Friedenstein, A. et al., Bone Marrow Osteogenetic Stem Cells: In Vitro Cultivation and Transplantation in Diffusion Chambers, Cell Tissue Kinet, 20(3):263-72, 1987.
Borgens, Electric Fields in Vertebrate Repair, Natural and Applied Voltage in Vertebrate Regeneration and Hearling, Wiley-Liss, 1989.
Sambrook et al., Molecular Cloning: A Laboratory Manual, $2^{nd}$ 3d., Cold Spring Harbor Laboratory, Cold Spring Harbor Laboratory Press, Cold Spring Harbor, NY, 1989. (cover page and Table of Contents for vols. 1-3).
Koga, et al., Crystallization, Field-Induced Phase Transformation, Thermally Induced Phase Transition, and Piezoelectric Activity in P(Vinylidene Fluoride-TrFE) Copolymers with High Molar Content of Vinylidene Fluoride, J. Appl. Phys, 67(2), pp. 965-974, 1990.
Safronova, et al., Characteristics of the Macromolecular Components of the Extracellular Matrix in Human Hyaline Cartilage at Different Stages of Ontogenesis, Biomedical Science, 2:162-168, 1991.
Haynesworth, S. et al., Cell Surface Antigens on Human Marrow-Derived Mesenchymal Stem Cells are Detected by Monoclonal Antibodies, J. Cell Physiol., 138:8-16, 1992.
Valentini, Electrically Charged Polymeric Substrates Enhance Nerve-Fiber Outgrowth in Vitro, Biomaterials, vol. 13, pp. 183-190, 1992.
Ausubel, et al., Current Protocols in Molecular Biology, John Wiley & Sons, New York, NY, 1993. (cover page and Table of Contentst).
Rickard, D. J. et al., Induction of rapid osteoblast differentiation in rat bone marrow stromal cell cultures by dexamethason and BMP-2, Dev. Bio., 161:218-28, 1994.
Ohigashi, et al., Formation of "Single Crystalline Films" of Ferroelectric Copolymers of Vinylidene Fluoride and Trifluoroethylene, Appl. Phys. Lett., 66(24), pp. 3281-3283, 1995.
Kapur., et al., Fabrication and Selective Surface Modification of 3-Dimensionally Textured Biomedical Polymers from Etched Silicon Substrates, Journal of Biomedical Materials Research, vol. 33, pp. 205-216, 1996.
Kapur, et al, Human Monocyte Morphology is Affected by Local Substrate Charge Heterogeneity, J, Biomed Mater. Res., 32: 133, 1996 (abstract only).
Bouaziz, et al., Vascular Endothelial Cell Responses to Different Electrically Charged Poly(Vinylidene Fluoride) Supports Under Static and Oscillating Flow Conditions, Biomaterials, vol. 18, No. 2, 107-112, 1997.
Christie, et al., Ferroelectric and Piezoelectric Properties of a Quenched Poly(Vinylidene Fluoride-Trifluoroethylene) Copolymer, Journal of Polymer Science: Part B: Polymer Physics, vol. 35, 2671-2679, 1997.
Furukawa, Structure and Functional Properties of Ferroelectric Polymers, Advances in Colloid and Interface Science, 71-72; 183-208, 1997.
Jaiswal, N. et al., Osteogenic differentiation of purified culture-expanded human mesenchymal stem cells in vitro, J. Cell Biochem., 64:295-312, 1997.
Kadiyala, S. et al., Culture-expanded, bone marrow-derived mesenchymal stem cells can regenerate a critical-sized segmental bone defect, Tissue Engineering, 3(2):173-185, 1997.
Miraglia, S. "A Novel Five-Transmembrane Hematopoietic Stem Cell Antigen: Isolation, Characterization, and Molecular Cloning," *Blood* 90:5013-21, 1997.
Omote, et al., Temperature Dependence of Elastic, Dielectric, and Piezoelectric Properties of "Single Crystalline" Films of Vinylidene Fluoride Trifluoroethylene Copolymer, J. Appl. Phys., 81(6), pp. 2760-2769, 1997.
Schmidt, et al., Stimulation of Neurite Outgrowth Using an Electrically Conducting Polymer, Proc. Natl. Acad. Sci, vol. 94, pp. 8948-8953, 1997.
Virts, E. et al. "Murine Mast Cells and Monocytes Express Distinctive Sets of CD45 Isoforms," *Immunology* 34(16-17):1119-97, 1997.
Yin, A.H. "AC133, A Novel Marker for Human Hematopoietic Stem and Progenitor Cells," *Blood* 90:5002-12, 1997.
Bruder, S. P. et al., Bone Regeneration by Implantation of Purified, Culture-Expanded Human Mesenchymal Stem Cells, J. Orthop. Res., 16:155-162, 1998.
Bune, et al., Two-Dimensional Ferroelectric Films, Nature, vol. 391, 874-877, 1998.
Mackay, A. M. et al., Chrondrogenic differentiation of cultured human mesenchymal stem cells from marrow, Tissue Engineering, 4(4):415-428, 1998.
Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.
Borgens, Electrically Mediated Regeneration and Guidance of Adult Mammalian Spinal Axons into Polymeric Channels, Neuroscience, 91(1):251-64; 1999.
Laurencin, C.T. "Tissue Engineering: Orthopedic Applications," *Ann. Rev. Biomed. Eng'g* 1:19-46, 1999.
Pittenger, M. F. et al., Multilineage potential of adult human mesenchymal stem cells, Science, 284:143-7, 1999.

(56) References Cited

OTHER PUBLICATIONS

Praemer, A., Musculoskeletal conditions in the United States, American Academy of Orthopaedic Surgeons, p. 34-39, 1999.
Sittinger et al., Joint cartilage regeneration by tissue engineering, Z. Rheumatol, 58:130-5, 1999.
Browne, J. E. et al., Surgical alternatives for treatment of articular cartilage lesions, J. Am. Acad. Orthop. Surg., 8(3):180-9, 2000.
DeLise, A. M. et al., Cellular interactions and signaling in cartilage development, Osteoarthritis and Cartilage, 8:309-34, 2000.
Fuchs, et al., Stem Cells: A New Lease on Life, *Cell* 100: 143-155, 2000.
Hilczer, et al., The Method of Matching Resonance Frequencies in Coupled Transmitter PVDF/TRFE Diaphragms, IEEE Transactions on Dielectrics and Electrical Insulation, vol. 7, No. 4, pp. 498-502, 2000.
Ponticello et al., Gelatin-Based Resorbable Sponge As A Carrier Matrix For Human Mesenchymal Stem Cells In Cartilage Regeneration Therapy, *J Biomed Materials Res* 52: 246-255, 2000.
Watt, et al., Out of Eden: Stem Cells And Their Niches, *Science* 287:1427-1430, 2000.
Xie, et al., A Niche Maintaining Germ Line Stem Cells in *Drosophila* Ovary, Science 290:328-330, 2000.
Barry, et al., Chondrogenic Differentiation of Mesenchymal Stem Cells from Bone Marrow: Differentiation-Dependent Gene Expression of Matrix Components, Experimental Cell Research, 268:189-200, 2001.
Brook et al., Columns of Schwann Cells Extruded Into the CNS Induce In-Growth Of Astrocytes To Form Organized New Glial Pathways, GLIA, 33:118-130, 2001.
Christensen, N. D. et al., Papillomavirus microbicidal activities of high-molecular-weight cellulose sulfate, dextran sulfate, and polystyrene sulfonate, Antimicrobial Agents and Chemotherapy, 45(12):3427-32, 2001,.
Guo et al., Biological features of mesenchymal stem cells from human bone marrow, Chinese Med J.. 114:950-3, 2001.
Harrison, et al., Piezoelectric Polymers, ICASE, NASA Langley Research Center, Hampton, Virginia, NASA/CR-2001-211422, ICASE Report No. 2001-43, pp. 1-26, 2001.
Ishihara, M. et al., Heparin-carrying polystyrene (HCPS)-bound collagen substratum to immobilize heparin-binding growth factors and to enhance cellular growth, J. Biomed. Mat. Res., 56(4):536-44, 2001.
Koombhongse, et al., Flat Polymer Ribbons and Other Shapes by Electrospinning, Journal of Polymer Science: Part B: Polymer Physics, vol. 39, 2598-2606, 2001.
Kotwal, et al., Electrical Stimulation Alters Protein Adsorption and Nerve Cell Interactions With Electrically Conducting Biomaterials, Biomaterials, 22: 1055-1064, 2001.
Negishi, Optic Nerve Regeneration Within Artificial Schwann Cell Graft In The Adult Rat, Brain Research Bulletin, 55:409-419, 2001.
N.S.C.I.A., Spinal Cord Injury Fact Sheet, Birmingham, 2001; http://users.erols.com/nscia/resource/factshts/.
Ploss, et al., Poling Study of PZT/P(VDF-TrFE) Composites, Composites Science and Technology, 61, 957-962, 2001.
Rahman et al., Enhancement of Chondrogenic Differentiation of Human Articular Chondrocytes by Biodegradable Polymers, Tissue Engineering, 7:781-90, 2001.
Rogovina, S. Z. et al., Solid state production of cellulose-chitosan blends and their modification and the diglycidyl ether of oligo(ethylene oxide), Polymer Degradation and Stability, 73(3):557-60, 2001.
Yannas IV, Tissue and Organ Regeneration in Adults, Springer, 2001(cover page and Table of Contents).
Anderson, R. A. et al., Preclinical evaluation of sodium cellulose sulfate (Ushercell) as a contraceptive antimicrobial agent, Journal of Andrology, 23(3):426-38, 2002.
Arinzeh, T. et al.,In vivo evaluation of a bioactive scaffold for bone tissue engineering, J. Biomed. Mat. Res., 62:1-13, 2002.
Dozin, B. et al., Response of young, aged and osteoarthritic human articular chondrocytes to inflammatory cytokines: molecular and cellular aspects, Matrix Biology, 21(5):449-59, 2002.
Li et al., Electrospun Naofibrous Structure: A Novel Scaffold For Tissue Engineering, Journal of Biomedical Materials Research, vol. 60, No. 4, pp. 613-621, 2002.
Muller, P. Y. et al., Processing of gene expression data generated by quantitative real-time RT-PCR, Biotechniques, 32(6):1372-4, 2002.
Nettles et al., Potential Use of Chitosan as a Cell Scaffold Material for Carilage Tissue Engineering, Tissue Engineering, Vo.. 8, No. 6, pp. 1009-1016, 2002.
Arinzeh, T. et al, Allogeneic mesenchymal stem cells regenerate bone in a critical-sized canine segmental defect, Journal of Bone and Joint Surgery American, 85-A(1):1927-35, 2003.
Benz, et al., Determination of the Crystalline Phases of Poly(Vinylidene Fluoride) Under Different Preparation Conditions Using Differential Scanning Calorimetry and Infrared Spectroscopy, Journal of Applied Polymer Science, vol. 89, 1093-1100, 2003.
Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.
Li, et al., Biological Response of Chondrocytes Cultured in Three-Dimensional Nanofibrous Poly($\epsilon$-caprolactone) Scaffolds, J. Biomed. Mat. Res. Part A., 67A, 4, pp. 1105-1114, 2003.
Livingston, et al., Mesenchymal Stem Cells Combined With Biphasic Calcium Phosphate Ceramics Promote Bone Regeneration, Journal of Materials Science: Materials in Medicine, 14: 211-218, 2003.
Luu et al., "Development of a Nanostructured DNA Delivery Scaffold via Electrospinning of PLGA and PLA-PEG block copolymers". Journal of Controlled Release, vol. 89, pp. 341-353, 2003.
Murphy et al., Stem Cell Therapy In A Caprine Model Of Osteoarthritis, *Arthritis Rheumatism* 48: No. 12, 34643474, 2003.
Sachlos, et al., Making Tissue Engineering Scaffolds Work, Review of the Application of Solid Freeform Fabrication Technology to the Production of Tissue Engineering Scaffolds, *European Cells & Materials* 5: 29-40, 2003.
Seoul, et al., Electrospinning of Poly(Vinylidene Fluoride)/ Dimethylformamide Solutions With Carbon Nanotubes, Journal of Polymer Science: part B: Polymer Physics, vol. 41, 1572-1577, 2003.
Sikavitsas et al., "Mineralized Matrix Deposition By Marrow Stromal Osteoblasts in 3D Perfusion Culture Increases With Increasing Fluid Shear Forces". PNAS, vol. 100, No. 25, pp. 14683-14688, Dec. 9, 2003.
Wan-Ju, et al., Biological Response of Chondrocytes Cultured in Three-Dimensional Nanofibrous Poly($\epsilon$-caprolactone) Scaffolds, J. Biomed. Mater. Res. 67A:1105-1114, 2003.
Yeh, E.T.H. et al., "Transdifferentiation of Human Peripheral Blood CD34+-Enriched Cell Population Into Cardiomyocytes, Endothelial Cells, and Smooth Muscle Cells in Vivo," Circulation 108:2070-73, 2003.
Yoshimoto et al., A Biodegradable Nanofiber Scaffold by Electrospinning and its Potential for Bone Tissue Engineering, Biomaterials, 24, pp. 2077-2082, 2003.
Zong et al., Electrospun Non-woven Membranes As Scaffolds For Heart Tissue Constructs. 226th ACS National Meeting, 2003.
Bhattarai, et al., Novel Biodegradable Electrospun Membrane: Scaffold for Tissue Engineering, Biomaterials, vol. 25, No. 13, pp. 2595-2602, 2004.
Bryan, et al., Enhanced Peripheral Nerve Regeneration Through A Poled Bioresorbable Poly(Lactic-co-glycolic Acid) Guidance Channel, J. Neural Eng., 1, 91-98, 2004.
Dezawa, Specific Induction of Neuronal Cells From Bone Marrow Stromal Cells and Application for Autologous Transplantation, Journal of Clinical Investigation; 113:1701-1710, 2004.
Jin et al., "Human Bone Marrow Stromal Cell Responses on Electrospun Silk Fibroin Mats", Biomaterials, vol. 25, pp. 1039-1047, 2004.
Li et al., Carbon Nanotubes Induced Nonisothermal Crystallization of Ethylene-Vinyl Acetate Copolymer, Materials Letter, 58, pp. 3967-3970, 2004.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.

(56) References Cited

OTHER PUBLICATIONS

Shields, K. J. et al., Mechanical properties and cellular proliferation of electrospun collagen Type II, Tissue Engineering, 10(9-10):1510-7, 2004.
Shin et al., In Vivo Bone Tissue Engineering Using Mesenchymal Stem Cells on a Novel Electrospun Nanofibrous Scaffold, Tissue Engineering, 10, pp. 33-41, 2004.
Stinger et al., Current Strategies for Cell Delivery in Cartilage and Bone Regeneration, Current Opinion in Biotechnology, vol. 115, Issue 5, pp. 411-418, 2004.
Wei et al., Structural and Properties of Nano-Hydroxyapatite/ Polymer Composite Scaffolds for Bone Tissue Engineering, Biomaterials, 25, pp. 4749-4757, 2004.
You, J. 0. et al., Calcium-alginate nanoparticles formed by reverse microemulsion as gene carriers, macromolecular Symposia, 219(147):153, 2004.
Rosenzweig, et al., Rodent Models for Treatment of Spinal Cord Injury: Research Trends and Progress Toward Useful Repair, Current Opinion in Neurology, 17(2); 121-31, 2004.
Arinzeh et al., A Comparative Study of Biphasic Calcium Phosphate Ceramics for Human Mesenchymal Stem-Cell-induced Bone Formation, Biomaterials, 26(17): 3631-8, 2005.
Aroen, A. et al, "Articular Cartilage Defects in a Rabbit Model, Retention Rate of Periosteal Flap Cover", Acta Orthrop. 76(2):220-4, 2005.
Browne, J. E. et al., Clinical outcome of autologous chondrocyte implantation at 5 years in US subjects, Clinical Orthopaedics and Related Research, 436:237-45, 2005.
Clar, C. et al., Clinical and cost-effectiveness of autologous chondocyte implantation for cartilage defects in knee joints: systematic review and economic evaluation, Health Technology Assessment, 9(47):four pages, 2005.
Cummings, et al., Human Neural Stem Cells Differentiate and Promote Locomoter Recovery in Spinal Cord-Injured Mice, Proceedings of the National Academy of Sciences, 102(39):14069-74, 2005.
Ducharme, et al., Ferroelectric Polymeric Langmuir-Blodgett Films for Non-Volatile Memory Applications, Nebraska Research Initiative, the National Science Foundation and the Office of Naval Research, Department of Physics and Astronomy and the Center for Materials Research and Analysis at the University of Nebraska, Lincoln, NE, pp. 1-41, 2005.
Fujihara, et al., Guided Bone Regeneration Membrane Made of Polycaprolactone/Calcium Carbonate Composite Nano-fibers, Biomaterials, 26, pp. 4139-4147, 2005.
Holmes, N. "CD45: All is Not Yet Crystal Clear", Immunology 117:145-155, 2005.
Kang, S. W. et al., Ply(lactic-co-glycolic acid) microspheres as an injectable scaffold for cartilage tissue engineering, Tissue Engineering, 11(3-4):438-47, 2005.
Klein, et al., Influence of Composition on Relaxor Ferroelectric and Electromechanical Properties of Poly(Vinyliden Fluoride-Trifluoroethylene-Chlorofluoroethylene), Journal of Applied Physics, 97, 094105, pp. 14, 2005.
Laxminarayana, et al., Functional Nanotube-Based Textiles: Pathyway to Next Generation Fabrics With Enhanced Sensing Capabilities, Textile Res. J., 75(9), 670-680, 2005.
Li et al., Multilineage Differentiation of Human Mesenchymal Stem Cells in a Three-Dimensional Nanofibrous Scaffold, Biomaterials, vol. 26, No. 25, pp. 5158-5166, 2005.
Livingston, et al., A Comparative Study of Biphasic Calcium Phosphate Ceramics for Human Mesenchymal Stem-Cell-Induced Bone Formation, Biomaterials, 26, pp. 3631-3638, 2005.
Maire, M. et al., Retention of transforming growth factor using functionalized dextran-based hydrogels, Biomaterials, 26(14):1771-80, 2005.
Montjovent et al., Biocompatibility of Bioresorbable Poly(L-lactic acid) Composite Scaffolds Obtained by Supercritical Gas Foaming With Human Fetal Bone Cells, Tissue Engineering 11, pp. 1640-1649, 2005.

Naber, et al., Low-Voltage Programmable Ferroelectric Polymer Field-Effect Transistors, Applied Physics Letters, 87: 203509, pp. 51-57, 2005.
Schaffellner, S. et al., Porcine islet cells microencapsulated in sodium cellulose sulfate, Transplantation Proceedings, 37(1):248-52, 2005.
Shapiro, et al., Oscillating Field Stimulation for Complete Spinal Cord Injury in Humans: A Phase 1 Trial, Journal of Neurosurgery Spine, 2005:2(1):3-10.
Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 18811891, 2005.
Wutticharoenmongkol, Preparation and Characterization of Novel Bone Scaffolds Based on Electrospun Polycaprolactone Fibers Filled with Nanoparticles, Macromolecular Bioscience, vol. 6, pp. 70-77, 2005.
Zhang et al., Tissue-Engineering Approaches for Axonal Guidance, Brain Res. Brain Res. Rev, vol. 49, pp. 4864, 2005.
Zhao, et al., Preparation and Properties of Electrospun Poly(Vinylidene Fluoride) Membranes, Journal of Applied Polymer Science, vol. 97, 466-474, 2005.
Beloti, et al., In Vitro Biocompatibility of a Novel Membrane of the Composite Poly(Vinylidene-Trifluoroethylene)/Barium Titanate, InterScience Journal of Biomedical Materials Research Part A, 281-288, 2006.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Gama, C. L., Sulfation patterns of glycosaminoglycans encode molecular recognition and activity, Nature Chemical Biology, 2(9):467-73, 2006.
Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.
Himes, et al., Recovery of Function Following Graf ing of Human Bone Marrow-Derived Stromal Cells Into the Injured Spinal Cord, Neurorehabilitation and Neural Repair, 20:278-96, 2006.
Hung, et al., The Effect of Chitosan and PVDF Substrates on the Behavior of Embryonic Rat Cerebral Cortical Stem Cells, Biomaterials, 27, 4461-4469, 2006.
Kuo, C. K. et al., Cartilage tissue engineering: its potential and uses, Current Opinion in Rheumatology, 18(1):64-73, 2006.
Li et al., Electrospinning Polyaniline-Contained Gelatin Nanofibers for Tissue Engineering Applications, Biomaterials, vol. 27, pp. 2705-2275, 2006.
Li et al., Electrospun Silk-BMP-2 Scaffolds for Bone Tissue Engineering, Biomaterials, 27, pp. 3115-3124, 2006.
Nasir, et al., Control of Diameter, Morphology, and Structure of PVDF Nanofiber Fabricated by Electrospray Deposition, Journal of Polymer Science: Part B: Polymer Physics, vol. 44, 779-786, 2006.
Oudega, et al., Schwann Cell Transplantation for Repair of the Adult Spinal Cord, Journal of Neurotrauma, 23(3-4), 453-67, 2006.
Pelttari, K. et al., Premature induction of hypertrophy during in vitro chondrogenesis of human mesenchymal stem cells correlates with calcification and vascular invasion after ectopic transplantation in SCID mice, Arthritis and Rheumatism, 54:3254-66, 2006.
Rezwan et al., Biodegradable and Bioactive Porous Polymer/ inorganic Composite Scaffolds for Bone Tissue Engineering, Biomaterials, 27, pp. 3413-3431, 2006.
Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.
Stiegler, P. B. et al., Cryopreservation of insulin-producing cells microencapsulated in sodium cellulose sulfate, Transplantation Proceedings, 38(9):3026-30, 2006.
Tashiro, et al, Structural Correlation Between Crystal Lattice and Lamellar Morphology in the Ferroelectric Phase Transition of Vinylidene Fluoride-Trifluoroethylene Copolymers as Revealed by the Simultaneous Measurements of Wide-Angle and Small-Angle X-Ray Scatterings, Polymer, 47, 5433-5444, 2006.

(56) References Cited

OTHER PUBLICATIONS

Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487493, 2006.
Wu, et al., Poly(Vinylidene Fluoride)/Polyethersulfone Blend Membranes: Effects of Solvent Sort, Polyethersulfone and Polyvinylpyrrolidone Concentration on Their Properties and Morphology, Journal of Membrane Science, 285, 290-298, 2006.
Wutticharoenmongkol et al., Preparation and Characterization of Novel Bone Scaffolds Based on Eletrospun Polycaprolactone Fibers Filled with Nanoparticles, Macromol. Biosci. 8, pp. 70-77, 2006.
Wutticharoenmongkol et al., Novel Bone Scaffolds of Electrospun Polycaprolactone Fibers Filled With Nanoparticles, Journal of Nanoscience Nanotechnology, 6(2), pp. 514-522, 2006.
Yang, et a. Preparation fo Bioelectret collagen and Its Influence on Cell Culture In Vitro, J. Mater. Sci: Mater Med, 17:767-771, 2006.
Catalani, et al. Evidence for Molecular Orientation and Residual Charge in the Electrospinning of Poly (Butylenes Terephthalate) Nanofibers, macromolecules, vol. 40, pp. 1693-1697, 2007.
Collins, M. N. et al., Comparison of the effectiveness of four different crosslinking agents with hyaluronic acid hydrogel films for tissue-culture applications, Journal of Applied Polymer Science, 104(5):3183-91, 2007.
Greco, S. et al., An interdisciplinary approach and characterization of neuronal cells transdifferentiated from huma mesnechyma stem cells, Stem cells and development, 16(5):811-26, 2007.
Greco, S. J. et al., Functional similarities among genes regulated by Oct. 4 in human mesenchymal and embryonic stem cells, Stem Cells, 25(12):3143-54, 2007.
Greiner et al, Electrospinning: A Facination Method for the Preparation of Ultrathin Fibers, Angewandte Chemie Int. Ed. Engl. 46: 5670-5703, 2007.
Huang, Isothermal Cystallization of High-Densidty Polyethylene and Nanaoscale Calcium Carbonate Composites, Journal of Applied Science, 107, pp. 3163-3172, 2007.
Karlsson, C. et al., Differentiation of human mesenchymal stem cells and articular chondrocytes: analysis of chondrogenic potential and expression pattern of differentiation-related transcritption factors, Journal of Orthopaedic Research, 25:152-63, 2007.
Lack, S. et al., High-resolution nuclear magnetic resonanace spectroscopy studies of polysaccharides crosslinked by sodium trimetaphosphate: a proposal for the reaction mechanism, Carbohydrate Research, 342(7): 943-53, 2007.
Miyazaki, et al, Crystallization Rate of Amorphous Nifedipine Analogues Unrelated to the Glass Transition Temperature, Interational Journal of Pharmaeceutics, 336, pp. 191-195, 2007.
Osiris Therapeutics Announces Positive One Year Data from Chondrogen Trial for Knee Repair, Osiris Therapeutics, Inc., Ref. Type: Internet Communication, 2007.
http://stemcells.nih.gove/info/scireport/appendixE.asp, (visited Dec. 28, 2007; last visited Aug. 25, 2011), 6 pages.
Sun, et al. Crystallization and Thermal Propertiese of Polyamide 6 Composites Filled With Different Nanofilelrs, Materials Letters, 61, pp. 3963-3966, 2007.
Temple, M. M. et al., Age- and site-associate biomechanical weakening of human articular cartilage of the femoral condyle, Osteoarthritis and Cartilage, 15: 1042-52, 2007.
Venguopal et al., Biocomposite Nanofibres and Osteoblasts for Bone Tissue Engineering, Nanotechnology, 18, pp. 1-8, 2007.
Wi, et al., Characterization of Poly(Vinylidene Fluoride-Trifluoroethylene) 50/50 Copolymer Films as a Gate Dielectric, J. Mater Sci: Mater Electron, pp. 1-6, 2007.
Xin, X. et al, Continuing differentitation of human mesenchymal stem cells and induced chondrogenic and osteogenic lineages in electrospun PLGA nanofiber scaffold, Biomaterials, 28(2):316-25, 2007.
Zhou et al., In Vitro Bone Engineering Based on Polycaprolactone and Polycaprolactone-Tricalcium Phosphate Composites, Polym. Int. 56, pp. 333-342, 2007.

Bian, L. et al., Influence of chondoitin sulfate on the biochemical, mechanical and frictional properties of cartilage explants in long-term culture, Journal of Biomechanics, In press 2008.
Chen, Y. et al., Development of a chitosan-based nanoparticle formulation for delivery of a hydrophilic hexapeptide, dalargin, Biopolymers, 90(5):663-70, 2008.
Chondrogen clinical trial information for the treatment of knee injuries, Osiris Therapeutics, Inc., Ref. Type: Internet Communication, 2008.
Duffell., et al., Long-Term Intensive Electrically Stimulated Cycling by Spinal Cord-Injured People: Effect on Muscle Properties and Their Relation to Power Output, Muscle and Nerve, 38:1304-11, 2008.
Forsten-Williams, K., et al., Control of growth factor networks by heparin sulfate proteoglycans, Annals of Biomedical Engineering, 36(12):2134-48, 2008.
Kim, et al., The Role of Aligned Polymer Fiber-Based Constructs in the Bridging of Long Peripheral Nerve Gaps, Biomaterials, 29(21):3117-27, 2008.
Lankford, et al., Olfactory Ensheathing Cells Exhibit Unique Migratory, Phagocytic and Myelinating Properties in the X-Irradiated Spinal Cord Not Shared by Schwann Cells, Glia, (epub ahead of print), 2008.
Liu, Z. et al., Polysaccharides-based nanoparticles as drug delivery systems, Advanced Drug Delivery Reviews, 60(15):1650-62, 2008.
Magnussen, R. A. et al., Treatment of focal articular cartilage defects in the knee: a systematic review, Clinical Orthopaedics and Related Research, 466(4):952-62, 2008.
Mueller, M. B. et al., Functional characterization of hypertrophy in chondrogenesis of human mesenchymal stem cells, Arthritis and Rheumatism, 58(5):1377-88, 2008.
PCT International Search Report and Written Opinion for PCT/US2005/043876 dated Jun. 25, 2008.
PCT International Search Report and Written Opinion for PCT/US2008/067322 dated Sep. 29, 2008.
ISP Dec. 24, 2008 for PCT/US2008/067322.
European Search Report dated Dec. 9, 2009 for PCT/US2005/043876.
IPRP Dec. 22, 2009 for PCT/US2008/067322.
Shanmugasundaram, S. et al., Regulation of human mesenchymal stem cell chondrogenesis by scaffold geometry and mechanical properties, Society for Biomaterials Annual Meeting, 2009.
Shanmugasundaram, et al., Microscale Versus Nanoscale Scaffold Architecture for Mesenchymal Stem Cell Chondrogenesis, Tissue Engineering: Part A, vol. 60, No. 00, pp. 1-10, 2010.
PCT International Search Report and Written Opinion for PCT/US2012/050156 dated Feb. 1, 2013.
European Patent Office Action for European Patent Application No. 05852938.9 dated Jul. 1, 2014.
U.S. Appl. No. 11/291,701, filed Dec. 1, 2005, US-2006-0128012-A1, Jun. 15, 2006.
U.S. Appl. No. 12/141,340, filed Jun. 18, 2008, US-2009-0028921-A1, Jan. 29, 2009.
U.S. Appl. No. 12/411,320, filed Mar. 25, 2009, US-2009-0325296-A1, Dec. 31, 2009.
U.S. Appl. No. 12/661,242, filed Mar. 12, 2010, 9,192,655, Nov. 24, 2015.
U.S. Appl. No. 12/661,264, filed Mar. 12, 2010, 9,334,476, May 10, 2016.
U.S. Appl. No. 12/763,755, filed Apr. 20, 2010, US-2010-0233807-A1, Sep. 16, 2010.
U.S. Appl. No. 13/097,657, filed Apr. 29, 2011, 9,180,166, Nov. 10, 2015.
U.S. Appl. No. 13/210,806, filed Aug. 16, 2011, 9,181,636, Nov. 10, 2015.
U.S. Appl. No. 13/651,296, filed Oct. 12, 2012, 9,476,026, Oct. 25, 2016.
U.S. Appl. No. 14/381,496, filed Aug. 27, 2014, US-2016-0000974-A1, Jan. 7, 2016.
PCT/US2005/043876, Dec. 1, 2005, WO 2006/068809, Jun. 29, 2006.

(56) References Cited

OTHER PUBLICATIONS

PCT/US2008/067322, Jun. 18, 2008, WO 2005/157594, Dec. 24, 2008.
PCT/US2012/050156, Aug. 9, 2012, WO 2013/023064, Feb. 14, 2013.

* cited by examiner

A

B

A

B

A

B

C

D

E

C

D

SCAFFOLD FOR TISSUE GROWTH AND REPAIR

CROSS-REFERENCE TO RELATED APPLICATIONS

This application claims the benefit under 35 U.S.C. § 119(e) of U.S. Provisional Patent Application Ser. No. 61/546,257; filed: Oct. 12, 2011, which is hereby incorporated by reference its entirety. In addition, this application is a divisional patent application claiming priority benefit to U.S. application Ser. No. 13/651,296, filed Oct. 12, 2012, which was a continuation-in-part application claiming priority benefit to U.S. application Ser. No. 12/661,264, filed Mar. 12, 2010, which was a continuation-in-part application claiming priority benefit to U.S. application Ser. No. 12/411,320, filed Mar. 25, 2009, which claimed the benefit of U.S. Provisional Application Ser. No. 61/159,751, filed Mar. 12, 2009.

GOVERNMENT RIGHTS

This invention was made with government support under DMR-1006510 awarded by the National Science Foundation and ILS-0534520 awarded by the National Science Foundation. The government has certain rights in the invention.

FIELD OF THE INVENTION

This invention relates to the fields of biotechnology, neuroscience, and regenerative medicine, such as, for example, cell growth/differentiation and/or tissue repair.

BACKGROUND

It has long been a goal of orthopeadics to identify rapid and effective means and materials for repairing complex tissues, including connective tissues, such as bone and cartilage, due to defects caused by, for example, injury, disease, wounds, or surgery. Tissue engineering principles have been utilized in recent years as an approach for such tissue repair and may be a suitable approach even for more complex tissue types.

The general approach to the use of tissue engineering in the repair and/or regeneration of tissue is to combine cells and/or biological factors with a biomaterial that acts as a scaffold for tissue development. The cells should be capable of propagating on the scaffold and acquiring the requisite organization and function in order to produce a properly functioning tissue. Such cells might include mesenchymal stem cells (MSCs) which are adult stem cells that are thought, due to their proliferative capacity and ability, to differentiate based on environmental cues into various connective tissue lineages, including bone and cartilage, and could be used in combination with engineered biomaterials for more complex tissue reconstructions, such as connective tissues like bone and/or cartilage. In addition, the biomaterials for use in such tissue engineering approaches might include certain "smart" biomaterials which may optimally imitate the natural organization and/or properties of a complex tissue sought to be repaired or regenerated.

Innovative technologies are needed for tissue engineering of inherently complex tissues, and in particular, musculo-skeletal connective tissue such as articular cartilage and the underlying bone tissue. Accordingly, compositions and methods that are capable of inducing bone and/or cartilage growth and repair are provided herein.

SUMMARY

Described herein are compositions and methods useful for promoting the growth and/or differentiation and/or repair of a cell and/or tissue, for example, a differentiable cell such as an isolated stem cell or progenitor cell. In one aspect that isolated stem cell or progenitor cell is a bone or cartilage stem or progenitor cell.

In certain aspects, the present invention provides an electroactive, or piezoelectric, biomaterial as an electroactive scaffold for facilitating growth, differentiation, and/or repair of a cell and/or a tissue. The piezoelectric material acts as a highly sensitive mechanoelectrical transducer that will generate charges in response to minute vibrational forces. Further provided are piezoelectric compositions comprising a three-dimensional matrix of micro and/or nanofibers of piezoelectric synthetic or biological polymers used as an implantable scaffolding for delivery of differentiable stem/progenitor cells, e.g., human mesenchymal cells, bone or cartilage stem/progenitor cells or the like, in tissue engineering applications and methods of preparing them. The piezoelectric scaffolds, which demonstrate electrical activity in response to minute mechanical deformation, allow the achievement of local electric fields characteristic of the natural extracellular matrix observed during development and regeneration or repair.

In one aspect, the present invention provides an electroactive structure for growing isolated differentiable cells that comprises a three dimensional matrix of micro- and/or nanosized fibers formed of a biocompatible synthetic piezoelectric polymeric material wherein the matrix of fibers is seeded with the isolated differentiable cells and forms a supporting scaffold for growing the isolated differentiable cells, and wherein the matrix of fibers alone or in combination with other factors stimulates differentiation of the isolated differentiable cells into a mature cell phenotype on the structure. In any of the embodiments described herein, the micro- or nanofibrous matrix of the electroactive structure or scaffold includes a random, and/or aligned, and/or patterned fibrous mesh of fibers.

In other aspects, presently described are polymer scaffolds for promoting tissue growth, differentiation, and/or repair. In an exemplary embodiment of this aspect, the scaffold matrix is comprised of a polymer that demonstrate piezoelectric properties. In certain embodiments, the piezoelectric polymer is a polyvinyl polymer or co-polymer, for example, a polyvinylidine fluoride (PVDF), trifluoroethylene (TrFE), or permanently piezoelectric poly (vinylidene fluoride trifluoroethylene) (PVDF-TrFE) copolymer. In another aspect, the piezoelectric polymer is annealed (e.g., annealed PVDF-TrFE).

In another aspect, presently described are polymer scaffolds formed by electro spinning. In an exemplary embodiment of this aspect, the scaffold is comprised of a matrix of micro and/or nanosized fibers formed by electrospining a piezoelectric polymer (i.e., a polymer that exhibits piezoelectric properties). In certain embodiments, the piezoelectric polymer to be electrospun into fibers comprises a polyvinyl polymer or co-polymer, for example, a polyvinylidine fluoride (PVDF), trifluoroethylene (TrFE), or permanently piezoelectric poly (vinylidene fluoride trifluoroethylene) (PVDF-TrFE) copolymer. In another embodiment, the matrix fibers are a non-woven mesh of micro- and/or nanosized fibers. In another embodiment, the three dimensional matrix of fibers formed of a biocompatible synthetic piezoelectric polymeric material is formed by electrospinning. In any of the embodiments described herein, the polymer tissue scaffold can be formed by electrospinning at a low voltage, e.g., 12 kV. In other embodiments, the polymer tissue scaffold can be formed by electrospinning at a high voltage, e.g., 25 kV. In another aspect, the piezoelectric polymer is annealed, for example, by heating or by chemical means. In certain embodiments, the polymer tissue scaffold is formed from electrospun, annealed PVDF-TrFE.

In some embodiments, the low voltage used during electrospinning can be about 11 kV or less, or about 12 kV, or about 13 kV. In other embodiments, the low voltage can be between about 5-8 kV, or between 8-11 kV, or between about 10-13 kV.

In other embodiments, the high voltage used during electrospinning can be about 15 to about 30 kV. In other embodiments, the high voltage can be between about 15-20 kV, or between about 18-23 kV, or between about 21-27 kV, or between about 24-30 kV, or between about 27-33 kV, or between about 30-40 kV.

In still other embodiments, the voltage applied during the electrospinning process can be varied between two or more voltages. In certain embodiments, the voltage during electrospinning can be varied between a low voltage, e.g., 10-13 kV, and a high voltage, e.g., 15-30 kV. The number and timing of the oscillations between two or more voltages are unrestricted. For example, during elecrospinning, the voltage can be varied between 11 kV and 30 kV, or between 11 kV and 25 kV, or between 11 kV and 15 kV, every nanosecond, microsecond, millisecond, second, or every multiple seconds, or even minutes.

In still other embodiments, the temperature(s) of any of the materials involved in the electrospinning process (e.g., the electrospinning apparatus, the material being electrospun, or the target substrate, such as an aluminum plate) may be any suitable temperature(s) and such temperatures may be the same or difference, and further, such temperatures may vary during the process. Suitable temperatures in certain embodiments can include, for example, about 25 degrees Celsius, or about 25-30 degrees Celsius, or between about 25-50 degrees Celsius, or any temperature below about 75 degrees Celsius.

In certain aspects of the invention, the differentiable cell matures or differentiates within and/or on the scaffold. The differentiation status of a cell can be determined by assessing suitable phenotypic markers, e.g., cell surface proteins, and/or gene expression profiles, which are specific for a differentiated cell. In certain aspects, the mature cell phenotype comprises a bone or cartilage cell phenotype. Therefore, in certain embodiments, the isolated differentiable cells are multipotent human mesenchymal cells or bone or cartilage (e.g., osteocyte or chondrocyte) stem/progenitor cells. In certain aspects, the cells are grown on a polymer tissue scaffold as described herein, wherein the scaffold is comprised within a compression bioreactor.

In another aspect, the present invention provides a composition for use in tissue engineering that comprises (a) isolated differentiable cells, and (b) a supporting electroactive scaffold for growing the isolated differentiable cells, the supporting scaffold comprising a three dimensional matrix of fibers formed of a biocompatible synthetic piezoelectric polymeric material, wherein the matrix of fibers is seeded with the isolated differentiable cells and forms a supporting scaffold for growing the isolated differentiable cells, and wherein the matrix of fibers stimulates differentiation of the isolated differentiable cells into a mature cell phenotype on the structure. In one embodiment, the biocompatible synthetic piezoelectric polymeric material is poly(vinylidene fluoride trifluoroethylene) copolymer. In another embodiment, the three dimensional matrix of fibers is a non-woven mesh of nanofibers. In still another embodiment, the three dimensional matrix of fibers formed of a biocompatible synthetic piezoelectric polymeric material is formed by electrospinning. In certain embodiments, the isolated differentiable cells are multipotent human mesenchymal cells, or neuronal stem/progenitor cells. In another embodiment, the mature cell phenotype comprises a neuronal cell phenotype. In another embodiment, step (a) further comprises the step of obtaining the differentiable human mesenchymal cells from bone marrow or other tissue, e.g., brain or spine.

In an additional aspect, presently described are polymeric scaffolds for modulating or promoting the growth, differentiation, and/or repair of a cell or tissue, for example, a mesenchymal stem cell, neuronal stem/progenitor cell, neuron, or the like. In certain embodiments, the polymeric scaffolds may include a matrix producing or supporting cell, e.g., a fibroblast. In further aspects, the polymeric scaffolds provided by the invention can be used alone or in combination with a cell to promote repair of damaged tissue, e.g., nerve tissue, in a subject. In certain embodiments, the cell or cells seeded in or on the scaffold comprises a mesnechymal stem cell. In additional embodiments, the polymeric scaffolds are seeded with a matrix producing or supporting cell.

In an additional aspect, the polymeric scaffolds provided by the invention are generated or fabricated in order to more closely mimic the structure of the natural extracellular matrix. In an exemplary embodiment of this aspect, the scaffold is comprised of an electrospun polymer that demonstrates piezoelectric properties. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer. In certain embodiments, the PVDF-TrFE is fabricated into a fibrous scaffold and the fibers are random, aligned or a combination of both. In certain embodiments the scaffold matrix, and/or fibers additionally comprise an exogenous protein or compound to promote cell growth, differentiation, and/or repair, including for example, growth factors, chemokines, polysaccharides, glycans, or the like.

In another aspect, described herein are methods for promoting and/or enhancing the growth, differentiation, and/or repair of a cell or of a tissue, e.g., a bone or cartilage tissue, comprising seeding a cell on a scaffold comprised of an electrospun polymer that demonstrates piezoelectric properties, wherein the scaffold promotes the growth, differentiation, and/or repair of a cell or tissue within or outside of the scaffold matrix. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer. In certain embodiments, the cell is a mesnechymal stem cell or other progenitor cell, e.g., a chrondrocyte progenitor cell, chondroblast progenitor cell, osteoblast progenitor cell, an osteocyte progenitor cell, or an osteoclast progenitor cell, or a combination thereof. In additional embodiments, the cell is seeded together with a matrix producing, and/or supporting cell or progenitor thereof.

In a particular embodiment, the present invention provides an electroactive structure for growing and differentiating a differentiable cell comprising a three dimensional matrix of electrospun biocompatible synthetic piezoelectric polymer fibers formed by electrospinning the polymer at a high electric potential, wherein the fiber matrix forms a scaffold for supporting cell growth and differentiation; and wherein the scaffold conditions are sufficient to induce differentiation of a mesenchymal stem cell into either an osteogenic or chondrogenic phenotype.

In certain embodiments, the biocompatible synthetic piezoelectric polymer is a homopolymer, a copolymer or combination thereof. homopolymer is a polyvinylidene fluoride (PVDF), or a ifluoroethylene polymer.

In other embodiments, the copolymer is a poly(vinylidene fluoride trifluoroethylene) (PVDF-TrFE) copolymer.

In yet other embodiments, the biocompatible synthetic piezoelectric homopolymer fibers are annealed.

In still other embodiments, the biocompatible synthetic piezoelectric copolymer fibers are annealed.

In still other embodiments, the fibers further comprise a growth factor capable of further promoting the differentiation of the mesenchymal stem cell into a osteogenic or chondrogenic phenotype. Such growth factor can be associated with the matrix of fibers through at least one of a covalent interaction, a non-covalent interaction or a combination of both.

In other embodiments, the matrix fibers can be a non-woven mesh of nanofibers, microfibers or a combination of both. The matrix fibers can also be arranged in the matrix randomly, substantially aligned or a combination of both.\

In still other embodiments, the fibers are thermally or chemically annealed, and wherein after annealing the fibers demonstrate enhanced piezoelectric characteristics, crystal organization or a combination of both.

In yet other embodiments, the fibers are thermally or chemically annealed, and wherein after annealing the fibers demonstrate enhanced piezoelectric characteristics, crystal organization or a combination of both.

In still other embodiments, the osteogenic or chondrogenic phenotype is demonstrated by at least one of increased collagen expression, growth or a combination thereof.

In other embodiments, the high electric potential is a voltage of at least between 15 to 30 kV.

In one embodiment, the high electric potential is 25 kV.

In still a further embodiment, the invention provides an implantable electroactive scaffold produced according to the steps comprising: (a) electropsinning a biocompatible synthetic piezoelectric polymeric material at at least 25 kV to form a three-dimensional matrix of piezoelectric fibers, wherein the fibers have an average fiber diameter of from about 500 nm to about 5 μm; (b) annealing the electrospun piezoelectric polymeric fibers; and (c) seeding the annealed three-dimensional matrix of piezoelectric fibers with a mesenchymal stem cell under conditions sufficient to induce differentiation of a mesenchymal stem cell into either an osteogenic or chondrogenic phenotype.

In other embodiments, the biocompatible synthetic piezoelectric polymeric material is at least one of a homopolymer, a copolymer or a combination of both.

In still the embodiments, the homopolymer is a polyvinylidene fluoride (PVDF), or a trifluoroethylene polymer or a copolymer such as a poly(vinylidene fluoride trifluoroethylene) (PVDF-TrFE) copolymer.

In other embodiments, the method of making the material can comprise the step of shaping the scaffold using a presses or mold.

In still another embodiment, the invention provides a method for repairing bone or cartilage tissue in a subject comprising the steps: (a) isolating at least one differentiable bone or cartilage progenitor cell from a donor subject; (b) preparing the electroactive scaffold of the invention; (c) seeding the cell scaffold with the isolated bone or cartilage progenitor cell; (d) growing the bone or cartilage progenitor cell on the cell scaffold ex vivo or in vitro; and (e) implanting the scaffold comprising the bone or cartilage progenitor cell at the site of injury, wherein the bone or cartilage progenitor cell differentiates into a mature bone or cartilage cell phenotype on the scaffold.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
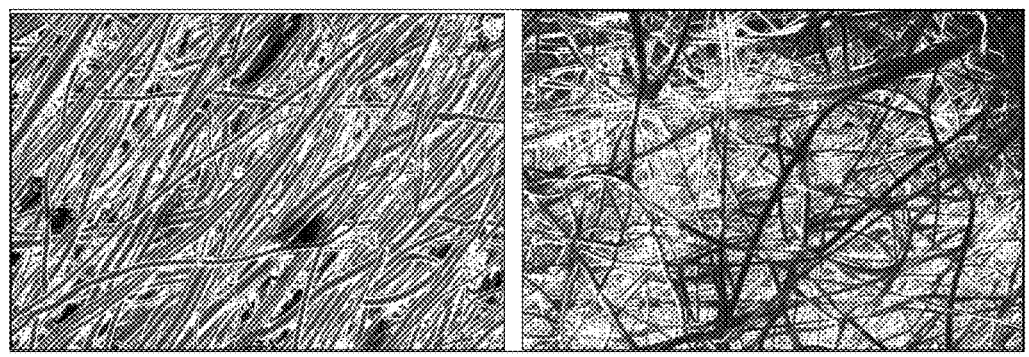
FIG. 1 depicts SEM images (magnification of 3500) of aligned (left) and random (right) electrospun PVDF-TrFE scaffolds.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Described herein are compositions and methods useful for promoting the growth, differentiation, and/or repair of a cell and/or tissue, e.g., a stem or progenitor cell. In particular, the present invention is based upon the surprising and unexpected discovery that cell and/or tissue growth, differentiation, and/or repair is/are enhanced when grown on a three-dimensional electroactive structure or scaffold comprising microsized or nanosized fibers, or both, of a piezoelectric polymer material. Unless otherwise indicated, the term "polymer" refers to either or both of a homopolymer and heteropolymer (i.e., co-polymer). The compositions and methods provided by the invention are useful as a research tool, a surgical implantation device, a cell or tissue culture device or a combination thereof for in vitro, in vivo, and/or ex vivo culture of a cell and/or tissue, e.g., a stem or progenitor cell, or other cell or tissue for the generation of tissue for repair of damaged tissue, for allographic or xenographic transplantation or any combination thereof.

The following patents and published patent applications are relevant to the subject matter of the present invention: U.S. Pat. Nos. 6,689,166 and 6,790,528; and U.S. Published Pat. App. Nos. 2004-0018226; 2006-0204539; 2009-0325296; 2009-0028921; and 2006-0128012, the disclosures of which are all incorporated herein by reference in their entirety for all purposes.

Unless defined otherwise, all technical and scientific terms used herein have the same meaning as commonly understood by one of ordinary skill in the art to which this invention belongs.

As used herein, the term "stem cell" refers to undifferentiated cells having high proliferative potential with the ability to self-renew that can migrate to areas of injury and can generate daughter cells that can undergo terminal differentiation into more than one distinct cell phenotype. These cells have the ability to differentiate into various cells types and thus promote the regeneration or repair of a diseased or damaged tissue of interest.

The term "progenitor cell" as used herein refers to an immature cell isolated from a tissue, including, e.g., bone marrow, brain, spinal cord, heart, adipose, connective, epithelium, endothelium, or the like, that can be isolated by growing suspensions of the cells in culture dishes with added growth factors. Progenitor cells are referred to as colony-forming units (CFU) or colony-forming cells (CFC). The specific lineage of a progenitor cell is indicated by a suffix, such as, but not limited to, CFU-F (fibroblastic).

As used herein, the term "polymer" refers to a macromolecule formed by the chemical union of five or more identical combining units called monomers. In most cases, the number of monomer is quite large and often is not precisely known. In synthetic polymers, this number may be controlled to a predetermined extent. Combinations two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon). Organic polymers may be natural [e.g., polysaccharides, such as starch, cellulose, pectin, seaweed gums, vegetable gums; polypeptides, such as casein, albumin, globulin, keratin, insulin, DNA; and hydrocarbons], synthetic [such as thermoplastics (unvulcanized elastomers, nylon, polyvinyl chloride, poly (vinylidene fluoride trifluoroethylene) linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)]. The term "homopolymer" refers to a natural or synthetic polymer derived from a single monomer. The term "heteropolymer" refers to a natural or synthetic polymer derived from more than one monomer subunit (i.e., co-polymer). Unless otherwise indicated, the term "polymer" is used generally to refer to both homopolymers and heteropolymers (i.e., co-polymer) as described herein.

The term "cellular differentiation" as used herein refers to the process by which cells acquire a cell type.

The term "$\Delta Hf$" refers to Heat of Fusion.

The term "nanoscale fiber" generally refers to fibers whose diameter ranges from about 1 to about 1000 nanometers.

The term "piezoelectric material" as used herein refers to any material that exhibits piezoelectric properties or effects. The terms "piezoelectric properties" or "piezoelectric effects" are used interchangeably to refer to the property exhibited by piezoelectric materials of becoming electrically polarized when mechanically strained and of becoming mechanically strained when an electric field is applied.

The present invention described hereinabove has both human and veterinary utility. The term "subject" as used herein therefore includes animals, e.g., those of mammalian origin, including humans.

The term "Tm" refers to melting point.

The term "growth factor" refers generally to bioactive cell signaling molecules, including cytokines and chemokines, which are known to elicit physiological effects through their interaction with cell surface receptors (typically receptor tyrosine kinases, Ser/Thr kinases, immunoglobulins or GPCRs) on a cell. The phyiological effects of growth factor binding to its receptor include, for example, changes in gene expression, and/or cell proliferation, differentiation, activation, quiescence, or apoptosis. In certain cases, growth factors are pleiotropic, i.e., they may induce different physiological effects depending on the concentration, cell type, and/or cell status. In any of the embodiments provided herein, the fiber, matrix, and/or scaffold may additionally include one or more growth factors to enhance, e.g., cell or tissue growth, differentiation, and/or repair.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

In certain aspects, the present invention provides an electroactive, or piezoelectric, biomaterial as an electroactive scaffold for enhancing or facilitating growth, differentiation, and/or repair of a cell and/or a tissue. The piezoelectric material acts as a highly sensitive mechanoelectrical transducer that will generate charges in response to minute vibrational forces. In certain embodiments, the invention provides piezoelectric compositions comprising a three-dimensional matrix of micro- and/or nanofibers of piezoelectric synthetic or biological polymers used as an implantable scaffolding for the growth and/or delivery of differentiable cells, for example, mesenchymal stem cells, progenitor cells, including neuronal stem/progenitor cells or any other cell for tissue engineering applications and methods of preparing them. The piezoelectric scaffolds, which demonstrate electrical activity in response to minute mechanical deformation, allow the achievement of local electric fields characteristic of the natural extracellular matrix observed during development and regeneration or repair. The differentiable cells can be isolated according to well known methods and may be isolated from any suitable subject, for example, a mammal, including a human.

Random, aligned, and patterned nano-fibrous mesh and three-dimensional structures can be fabricated by altering collection methods as described herein. The topographic features of nano-aligned-fibrous scaffolds create contact guidance. For example, in the case of a isolated differentiable neuronal stem or progenitor cell, the aligned fibrous scaffold fabricated in accordance with the present description can further facilitate axonal extension. Experimental results have demonstrated for certain exemplary embodiments, enhanced neuronal differentiation and neurite extension on PVDF-TrFe meshes. Also, cells on aligned nanofiber scaffolds extend neurites unidirectionally, parallel with the aligned fibers.

Specialized protein receptors that have the capability of selectively binding or adhering to other signaling molecules coat the surface of every cell in the body. Cells use these receptors and the molecules that bind to them as a way of communicating with other cells and to carry out their proper functions in the body. Each cell type has a certain combination of receptors, or markers, on their surface that makes them distinguishable from other kinds of cells. In certain embodiments, comprising a neuronal stem/progenitor cell, piezoelectric polymers can induce transient change of surface charge without requiring additional energy sources or electrodes and have been shown to yield a higher level of neuronal differentiation and neurite outgrowth of mouse neuroblastoma cells.

Therefore, in one aspect the present invention provides a novel electroactive structure or scaffold to be used to promote growth, differentiation, and/or repair of a differentiable stem/progenitor cell, e.g., a mesenchymal cell or neuronal stem/progenitor cell. As described herein, in an exemplary embodiment, the piezoelectric property of the fiber matrix promotes neurite extension by neuronal stem/progenitor cells incorporated into the piezoelectric scaffold. The piezoelectric scaffold in an aligned nanofibrous format provides the appropriate physical cues to promote axonal regeneration.(8-10) By combining the scaffold with neuronal stem/progenitor cells, the cells may provide the therapeutic benefit of neuroprotection(11) and/or functionally integrate into the spared spinal cord circuitry (e.g. forming new oligodendrocytes and/or neurons)(12;13) to improve therapeutic outcomes.

Thus, in an exemplary embodiment, the invention provides an electroactive structure for growing an isolated differentiable stem/progenitor cell comprising a three dimensional matrix of fibers comprising a biocompatible synthetic piezoelectric polymeric material, wherein the matrix of fibers is seeded with at least one isolated differentiable stem/progenitor cell and forms a supporting scaffold for growing the isolated differentiable stem/progenitor cell. In certain embodiments, the isolated differentiable cell is a differentiable neuronal stem/progenitor cell or other cell or progenitor cell capable of being differentiated into a nerve cell. In another embodiment, the matrix of piezoelectric fibers stimulates growth, differentiation, and/or repair of the isolated differentiable neuronal progenitor cell into a mature neuronal cell phenotype on the structure, for example, a peripheral nerve, brain or spinal cord neuron. In this context, it is to be understood that the word "on" is used in broad sense and refers to, and includes, by way of example, cells growing partially or completely "on," "in," "within," and/or "through" the structure.

After spinal cord injury (SCI) unidirectional aligned structure of the axons is disrupted [1] and restoring the original structure is necessary for functional recovery. A tissue-engineered bridging device as described herein is a promising method to guide axonal outgrowth for repair of SCI. However, the cell favors the implantation site more [1], thus appropriate topographic cues within the bridging device may be crucial in successfully guiding axons to extend out of the bridge and to enhance host-implant interaction. As discussed above, local electric fields have been measured during neural development or after nerve injury in various vertebrate systems [2]. Electric fields generated via electrodes have been shown to influence growth and orientation of neurons in vitro [3]. It was surprisingly and unexpectedly discovered that piezoelectric polymers can induce transient change of surface charge without requiring additional energy sources or electrodes and have been shown to yield a higher level of cell growth, differentiation, and repair as exemplified by the observed neuronal differentiation and neurite outgrowth of mouse neuroblastoma cells [4].

In any of the embodiments described herein, the biocompatible synthetic piezoelectric polymer may be comprised of any suitable polymeric material that demonstrates piezoelectric properties. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer. The steric hindrance of the TrFe polymer in PVDF-TrFE forces the copolymer into an all-trans configuration and is considered piezoelectric [5].

In certain embodiments, the piezoelectric polymeric scaffold as described herein is formed by electrospinning. Electrospinning is used to synthesize polymeric tissue engineering scaffolds by applying a high voltage to an ejectable polymer solution. The basic principle behind this process is that an electric voltage sufficient enough to overcome the surface tension of a polymeric solution causes the polymer droplets to elongate so that the polymer is splayed randomly as very fine fibers, which when collected on a grounded metal plate, form a non-woven mat or mesh. Traditionally, electrospinning has yielded non-woven (i.e., mesh) mats (also called matrices and scaffolds) of nanometer sized fiber diameters and nanometer sized pore diameters. However, in order for cells to infiltrate into a scaffold and proliferate, micron sized fiber diameters and micron sized pore diameters are optimal. Since the diameter of a cell is approximately 10 µm to 20 µm, pore sizes at the cellular level or above are needed to allow for cell infiltration. In an exemplary embodiment, the matrix fibers comprise a non-woven mesh of random and/or aligned nanofibers or microfibers or a combination thereof.

In certain embodiments, the electrospun fibers have an average fiber diameter of from about 100 nm to about 100 microns. In an additional embodiment, the electrospun fibers have an average fiber diameter of from about 600 nm to about 5 microns. In a preferred embodiment, the electrospun fibers are PVDF-TrFE fibers and have an average fiber diameter of from about 750 microns to about 5 microns.

In certain embodiments, the polymer, e.g., PVDF-TrFE, is fabricated into a fibrous matrix scaffold and the fibers are arranged randomly, substantially or approximately aligned or a combination of both. As used herein, "substantially or approximately aligned" refers to a matrix in which the fibers show more directional uniformity in any desired plane as compared to a "random" fiber matrix. In an exemplary embodiment of this aspect, the scaffold is comprised of a matrix of substantially axially aligned electrospun fibers using a polymer that demonstrates piezoelectric properties. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer.

In any of the embodiments described herein, the fibers of the electroactive structure may be thermally annealed prior to seeding with an isolated differentiable stem/progenitor cell. The annealing step increases the size of the beta phase crystal in the piezoelectric materials, which results in an increase in the piezoelectric property or resulting electrical activity of the material. As described in further detail below, thermal annealing of the matrix fibers results in enhanced piezoelectric characteristics, and/or improved crystal organization. The improved piezoelectric properties of the annealed fibers improves stem/progenitor cell growth, and/or differentiation. In a preferred embodiment, the fibers are annealed by incubating the scaffold at 135° C. for 96 hours and quenched with ice water prior to seeding with a cell. In any of the embodiments described herein, the annealing time can be varied, however, the annealing step must occur below the melting temperature of the material.

In certain additional embodiments, the scaffold demonstrates polarity in one or more planes such as through a gradient in, for example, fiber diameter, fiber composition, pore size, concentration of chemical or growth factor cues or a combination thereof. By varying the polarity of the scaffold directional growth or polarized cell growth may be enhanced.

In certain aspects the scaffold matrix, and/or fibers additionally comprise an exogenous protein or compound to promote cell growth, differentiation, and/or repair, including for example, growth factors, chemokines, polysaccharides, glycans, or the like. In any of the embodiments described herein, the polymer fiber, matrix, and/or scaffold may additionally include one or more growth factors. In certain embodiments, the growth factor to be included is capable of enhancing or further promoting cell growth and/or differentiation of the differentiable stem/progenitor cell into a mature cell phenotype. For example, in one exemplary embodiment, the cell to be seeded is an isolated differentiable neuronal progenitor cell, and a suitable growth factor to be included comprises nerve growth factor (NGF), brain-derived neurotrophic factor or a combination thereof. In any of the embodiments described herein, the growth factor may be associated to at least one of the polymeric fiber, matrix, and/or scaffold through a covalent interaction, a non-covalent interaction or a combination of both.

In certain aspects of the invention, the differentiable cell matures or differentiates within and/or on the scaffold. The differentiation status of a cell can be determined by assessing suitable phenotypic markers, e.g., cell surface proteins, and/or gene expression profiles, which are specific for a differentiated cell. In one embodiment, the mature cell phenotype comprises a neuronal cell phenotype. The mature neuronal cell phenotype is demonstrated by at least one of increased tubulin expression, reduced expression of nestin, neurite growth or a combination thereof. The mature cell phenotype can be detected using any suitable method or assay, e.g., immunoglobulin or PCR-based methods, including ELISA, Western Blot, Northern Blot, RTQ-PCR, chemiluminescence/FACS cell sorting or a combination thereof. Suitable molecular biological and biochemical techniques for assaying for the phenotype of a cell are known in the art and are described in, for example, Ausubel, et al., CURRENT PROTOCOLS IN MOLECULAR BIOLOGY, John Wiley & Sons, New York, N.Y., 1993; Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In an additional aspect, the invention provides the electroactive structure for growing isolated differentiable cell described herein comprise a three dimensional matrix of fibers comprising a biocompatible synthetic piezoelectric polymeric material, wherein the matrix of fibers is seeded with a combination of at least one isolated differentiable cell and a matrix producing or supporting cell, for example, a fibroblast, wherein the structure forms a supporting scaffold for growing/differentiating the isolated differentiable cell. In certain embodiments, the isolated differentiable cell is a differentiable neuronal stem/progenitor cell or cell capable of being differentiated into a nerve cell. In certain additional embodiments, the matrix producing or supporting cell to be included comprises a fibroblast, a glial cell, a satellite cell, a Schwann cell or a combination thereof, wherein the combination stimulates differentiation of the isolated differentiable neuronal stem/progenitor cell into a mature neuronal cell phenotype on the structure.

The polymeric scaffolds provided by the invention are generated or fabricated in order to more closely mimic the structure of the natural extracellular matrix in order to promote growth and differentiation of the seeded cell and to facilitate transplantation and/or implantation of the scaffold or cells grown on the same. For example, experimental results have demonstrated for certain exemplary embodiments, enhanced neuronal progenitor cell differentiation and neurite extension on PVDF-TrFe meshes. Also, cells on aligned nanofiber scaffolds extend neurites unidirectionally, parallel with the aligned and/or annealed fibers.

Therefore, in another aspect, described herein are methods for promoting and/or enhancing the growth and/or differentiation of a differentiable stem/progenitor cell, e.g., a neuronal stem/progenitor cell, comprising seeding a differentiable stem/progenitor cell on a scaffold comprised of an electrospun polymer that demonstrates piezoelectric properties, wherein the scaffold promotes the growth and/or differentiation of the differentiable stem/progenitor cell. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer. In certain embodiments, the differentiable stem/progenitor cell is a neuronal stem/progenitor cell or cell capable of being differentiated into a mature nerve cell type. In an additional embodiment, the fibers are substantially aligned and/or annealed.

In other aspects, the invention provides a method of making an implantable electroactive scaffold. In an exemplary embodiment, the method comprises the steps of (a) isolating differentiable stem/progenitor cell from a donor subject; (b) preparing a three-dimensional matrix of fibers formed of a biocompatible synthetic piezoelectric polymeric material to form a cell scaffold; (c) seeding the cell scaffold with the isolated differentiable stem/progenitor cell; and (d) growing the differentiable stem/progenitor cell on the cell scaffold so that the differentiable stem/progenitor cell differentiates into a mature cell phenotype on the scaffold. In a preferred embodiment, the differentiable stem/progenitor cell is a neuronal stem/progenitor cell or a cell capable of being differentiated into a mature nerve cell, e.g., a peripheral nerve, a CNS or spinal cord nerve. In certain embodiments, the subject is a mammal, for example a human. In an additional embodiment, the biocompatible synthetic piezoelectric polymeric material in step (b) is poly(vinylidene fluoride trifluoroethylene) copolymer. In any embodiment of this aspect, the three dimensional matrix of fibers may be formed of a biocompatible synthetic piezoelectric polymeric material by electrospinning. Further still, in any embodiment described herein, the three dimensional matrix of fibers is a non-woven mesh of nanofibers, microfibers or a combination of both. In still further embodiments, the fibers are aligned and/or annealed.

In another aspect, the invention provides methods of repairing a damaged neuronal cell or tissue in a subject. An exemplary embodiment of this aspect comprises the steps of (a) isolating at least one differentiable stem/progenitor cell from a donor subject; (b) preparing a three-dimensional matrix of fibers formed of a biocompatible synthetic piezoelectric polymeric material to form a cell scaffold; (c) seeding the cell scaffold with the isolated differentiable stem/progenitor cell; (d) growing the isolated differentiable stem/progenitor cell on the cell scaffold ex vivo or in vitro; and (e) implanting the scaffold comprising the differentiable stem/progenitor cell at the site of injury, wherein the differentiable stem/progenitor cell differentiates into a mature cell phenotype on the scaffold. In certain embodiments, the differentiable stem/progenitor cell fully differentiates on the scaffold in vivo.

In a preferred embodiment, the differentiable stem/progenitor cell is a neuronal stem/progenitor cell or a cell capable of being differentiated into a mature nerve cell, e.g., a peripheral nerve, a CNS or spinal cord nerve. In certain embodiments, the subject is a mammal, for example a human. In an additional embodiment, the biocompatible synthetic piezoelectric polymeric material in step (b) is poly(vinylidene fluoride trifluoroethylene) copolymer. In any embodiment of this aspect, the three dimensional matrix of fibers may be formed of a biocompatible synthetic piezoelectric polymeric material by electrospinning. Further still, in any embodiment described herein, the three dimensional matrix of fibers is a non-woven mesh of nanofibers, microfibers or a combination of both. In still further embodiments, the fibers are aligned and/or annealed.

The following examples are put forth so as to provide those of ordinary skill in the art with a complete disclosure and description of how to make and use the present invention, and are neither intended to limit the scope of what the inventors regard as their invention nor they intended to represent that the experiments below are all or the only experiments performed

EXAMPLES

Materials and methods useful for practicing the present invention may be further described in one or more of the following: U.S. Pat. Nos. 6,689,166; and 6,790,528; and U.S. Published Pat. App. Nos. 2004-0018226; 2006-0204539; 2009-0325296; 2009-0028921; and 2006-0128012, the disclosures of which are all incorporated herein by reference in their entirety for all purposes.

Example 1: Fabrication of Piezoelectric Tissue Engineering Scaffolds

The present invention makes use of fibers formed from a permanently piezoelectric poly(vinylidene fluoride trifluoroethylene) (PVDF-TrFE) copolymer. The PVDF-TrFE copolymer was fabricated into a nanofibrous scaffold using an electrospinning technique.

The electrospinning process is affected by varying the electric potential, flow rate, solution concentration, capillary-collector distance, diameter of the needle, and ambient parameters like temperature. PVDF-TrFE and PLLA were electrospun into fibers according to commonly used optimization procedures whereby porosity, surface area, fineness and uniformity, diameter of fibers, and the pattern thickness of the sheet could be manipulated. See, e.g., Greiner, A. et al Angew Chem. Int. Ed. Engl. 46: 5670 (2007).

The electrospinning setup used herein is described in U.S. patent application Ser. No. 11/291,701, which is incorporated herein by reference. It is comprised a syringe pump containing a 13-20 gauge needle mounted on a robotic arm in order to control the splaying of fibers on the collector. An electrically grounded stainless steel plate of dimensions 15×30 cm is used as the collector.

PVDF-TrFE copolymer (65/35) purchased from Solvay Solexis, Inc. (NJ, USA) was dissolved in Methylethylketone (MEK). For the successful formation of fibers, a 15% w/v solution concentration of the polymer in MEK was used. The syringe pump was filled with the polymer solution, and a constant flow rate of 0.035 ml/min was maintained using the syringe pump. The positive output lead of a high voltage power supply (Gamma High Voltage, Inc.) was attached to a 20 gauge needle, and a 25 kvolt voltage was applied to the solution. The collector-to-needle distance was 18.5 cm. The electrospinning process was performed in about 12% to about 13% humidity at 25 degrees C. When the charge of the polymer at increasing voltage exceeded the surface tension at the tip of the needle, the polymer splayed randomly as fibers. These were collected as nonwoven mats on the grounded plate.

Example 2: Characterization of the Electrospun PVDF-TrFE Fibers

Structure and piezoelectric activity of PVDF-TrFE fibers were examined by differential scanning calorimetry (DSC), thermogravimetric analysis (TGA), thermally stimulated current (TSC) spectroscopy, X-ray diffraction (XRD) and fourier transform infrared spectroscopy (FTIR). Comparisons were made between PVDF-TrFE polymer powder and electrospun PVDF-TrFE fibers.

The fiber diameter of electrospun PVDF-TrFE fibers was characterized using Scanning Electron Microscopy (SEM) according to established methods and compared to poly L-lactic acid (PLLA) meshes. FIG. 1 shows that the resulting fibrous meshes had an average fiber diameter of 970±480 nm, with uniform fiber morphologies having no beading, as characterized by scanning electron microscopy. The fiber mats were free of droplets.

Thermally stimulated current (TSC) spectroscopy is widely used to understand dielectric relaxation in complex solid systems. TSC is based on the ability of polar molecules to be moved by an electric static field. At a temperature Tp, an electric field is applied during a time tp long enough to let the dipoles orient themselves. This configuration is fixed by a rapid decrease in temperature to reach a temperature T0. At T0, the sample is short-circuited during a time t0 to remove the space charges and to equilibrate the temperature. The progressive and sequential release of the entities oriented previously can be observed during a linear rise in temperature. The depolarization current is then recorded as a function of the temperature.

Figure 2:
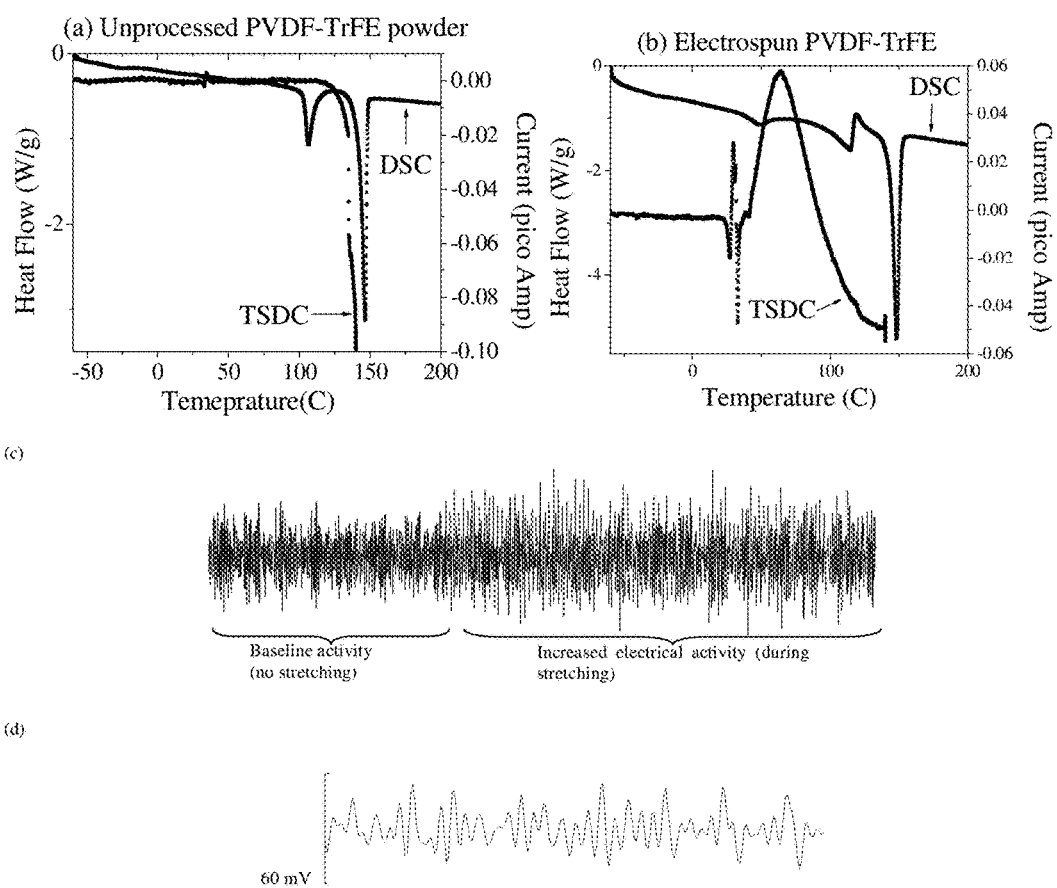
FIG. 2 depicts DSC (heat flow) and TSDC (current) results for unprocessed powder (a) and electrospun PVDF-TrFE (b). Electric response of PVDF-TrFE scaffold (c) when initializing deformation and (d) 25 ms duration while deforming.

TSC measurements confirmed that the electrospun PVDF-TrFE fiber scaffolds have internal charges comparable to the original piezoelectric polymer powder. The electrospun and powder forms were heated from −60° C. to 140° C. (7 C per min) and were subjected to an externally applied field of 100 V. FIG. 2 shows the data resulting from TSC analysis of the electrospun PVDF-TrFE mat and the non-processed powder form. It shows that for both the powder and electrospun forms, there was polarization due to the applied electric field followed by a spontaneous relaxation.

Thermal Gravimetric Analysis (TGA) was performed to detect any remaining solvent in the nanofiber mat using a Thermal Gravimetric Analyzer (TA Instrument model Q50). The analyzer measures weight changes in materials with regard to temperature, which allows for the effective quantitative analysis of thermal reactions that are accompanied by mass changes resulting from dehydration, decomposition and oxidation of a sample.

The nanofiber mat was subjected to vacuum prior to the analysis. A sample of the test material was placed into a high alumina cup supported on, or suspended from, an analytical balance located outside the furnace chamber. The balance was zeroed, and the sample cup heated according to a predetermined thermal cycle. The balance sends the weight signal to the computer for storage, along with the sample temperature and the elapsed time. The TGA curve plots the TGA signal, converted to percent weight change, on the Y-axis against the reference material temperature on the X-axis.

The results showed that fibrous meshes with vacuum treatment had a 0.5% solvent content as demonstrated by a loss of 0.5 weight percent as compared to the unprocessed/raw polymer.

Results obtained by DSC, XRD and FTIR showed that the electrospinning process did not alter significantly the polymer structure compared to the original piezoelectric polymer powder.

Differential scanning calorimetry (DSC) is used to study the thermal behavior of polymers. In this technique, separate chambers for the sample and reference are heated equally. Transformations taking place in the sample are detected by the instrument, which compensates by changing the heat input so that there is a zero temperature difference between the reference and sample. The amount of electrical energy supplied to the heating elements is then proportional to the heat released by the sample. Thermal analysis was performed with a TA Model Q100 Differential Scanning calorimeter.

Fourier-Transform Infrared Spectroscopy (FTIR) is used to observe vibrational changes in chemical bonds. Here, infrared radiation in the range from 4000 to 600 cm$^{-1}$, the mid-infrared region, was used. The presence and intensity of specific vibrational frequencies allows for determination of functional groups in organic molecules. The class of material (proteinaceous, cellulosic, and so forth) then can be identified from these functional groups.

A micro x-ray diffractometer capable of focusing a collimated x-ray beam (20 to 800 micron diameter range) onto areas of interest within the sample was used to generate an x-ray diffraction (XRD) pattern characteristic for the crystalline phases contained within the sample. X-rays diffracted by the sample strike a detector and are converted to an electronic signal that is then further processed by software. Search-match software then was used to match the unknown diffraction pattern to a database of diffraction patterns collected from reference compounds.

The degree of crystallinity was determined, and the piezoelectric crystal form of the copolymer present in the electrospun PVDF-TrFE mats was confirmed, by DSC. Comparisons of PVDF-TrFE mats with the piezoelectric unprocessed powder and solvent-cast film as well as with nonpiezoelectric-unpoled PVDF pellets were made.

TABLE 1

Comparison of DSC data with literature values

| Physical form | PVDF Pellet | PVDF-TrFE (65/35) Powder | PVDF-TrFE (65/35) Solvent-cast film | PVDF-TrFE (65/35) Electrospun fiber |
|---|---|---|---|---|
| Tm(C) | 171 (161*) | 107 (1 peak) 147 (154.55**) (2 peak) | 115 (1 peak) 147 (2 peak) | 115 (1 peak) 149 (2 peak) |
| ΔHf(J/g) | 45 (50*) | 13 (1 peak) 23 (30**) (2 peak) | 13 (1 peak) 34 (2 peak) | 15 (1 peak) 28 (2 peak) |

*Zhao, Z. et al., J. Appl. Polym. Sci. 97: 466-74 (2005);
**Data provided by supplier (Solvay Solexis, Inc.)

Table 1, which compares the experimental DSC data with literature values for test polymers (in parentheses), shows that low and high temperature peaks were observed in the PVDF-TrFE polymer during the first and second heating cycle. The differences in the first heating cycle between the test polymers were not detectable in the second heating cycle, which suggests that there is no chemical degradation or changes in the chemical structure due to the fabrication process. The melting points and heats of fusion for PVDF-TrFE materials are distinct from values obtained for the unpoled PVDF pellet, indicating that the piezoelectric beta-phase crystal form is present in the electrospun mat.

Moreover, the electrospun electroactive PVDF-TrFE fibers of the present invention do not require poling to show a piezoelectric effect. The term "poling" as used herein refers to the adjustment of the polarity of a substance. For example, electric dipoles may be aligned (meaning arranged, positioned or synchronized in a manner that allows for proper or optimal functioning) by utilizing an electric field. In this content, the term "polarity" refers to the property, state or condition of having or manifesting two opposite or opposing charges within the same body (versus, e.g., cellular polarity, which refers to a situation in which a cell has two or more anatomically and/or functionally distinct cellular domains).

Example 3: PVDF-TrFE Fiber Mats Support Stem Cells

Three studies were conducted to establish that the PVDF-TrFE fiber mesh can be used as a scaffold to support stem cells or other cell types.

Materials and Methods

Cells.

(a) Cell line model for neuronal differentiation. When treated with nerve growth factor (NGF), PC12 cells, a cell line derived from a pheochromocytoma of the rat adrenal medulla, stop dividing, grow long neurites, and undergo terminal differentiation, which makes this cell line a useful model system for neuronal differentiation.

PC12 cells (ATCC number CRL-1721) were seeded at $3 \times 10^3$ cells per $cm^2$ culture dish and maintained in ATCC formulated F-12K medium containing 1.5% fetal bovine serum and 15% horse serum. Cultures were maintained at 37° C., 95% air, 5% $CO_2$ atmosphere. For induction of the neuronal phenotype, 50 ng/ml NGF (Chemicon) was added to the medium at the start of the culture and maintained throughout the duration of the culture. The term "induction media" refers to the medium containing NGF.

(b) Fibroblasts. Normal human skin fibroblasts (ATCC number SCRC-1041) were seeded at $5 \times 10^3$ cells per $cm^2$ culture dish and maintained in Dulbecco's modified Eagle's medium containing 15% fetal bovine serum.

(c) Mesenchymal stem cells. Human mesenchymal stem cells (hMSCs) were prepared as described in Livingston, et al., *J. Materials Science: Materials in Med.* 14: 211-218 (2003) and in U.S. Pat. No. 5,486,359, which are incorporated herein by reference. In brief, bone marrow aspirates of 30-50 mL were obtained from healthy human donors. Marrow samples were washed with saline and centrifuged over a density cushion of ficoll. The interface layer was removed, washed, and the cells counted. Nucleated cells recovered from the density separation were washed and plated in tissue culture flasks in Dulbecco's Modified Eagle's Medium (DMEM) containing 10% fetal bovine serum ("FBS", HyClone Laboratories, Inc.). Non-adherent cells were washed from the culture during biweekly feedings. Colony formation was monitored for a 14-17 day period. MSC's were passaged when the tissue culture flasks were near confluent. At the end of the first passage, MSCs were enzymatically removed from the culture flask using trypsin-EDTA and replated at a lower density for further expansion. At the end of the second passage, MSC's were either seeded onto scaffolds or cryopreserved until future use. The hMSC cells were identified as multipotent stem cells based on surface marker characterization, which distinguishes the stem cells from other cell types in the bone marrow, for example white blood cells. Cells expressing CD44 (CD44+) and the absence of CD45 (CD45–) and CD34 (CD34–) surface antigens were verified by fluorescence-activated-cell-sorter.

Chondrogenic Differentiation.

Chondrogenic differentiation of hMSCs was performed according to published procedures. See Barry, F. et al., *Exp. Cell Res.* 268, 189 (2001), which is incorporated herein by reference. $2 \times 10^5$ cells were seeded on PVDF-TrFE scaffolds in 24-well plates using three different culture media: (i) the chondrogenic culture media containing TGFβ3, or induction media, (CCM+), consisted of 1 mM sodium pyruvate (Sigma), 0.1 mM ascorbic acid-2-phosphate (Wako), $1 \times 10^{-7}$ M dexamethasone (Sigma), 1% ITS 1 (Collaborative Biomedical Products), and 10 ng/ml recombinant human TGFβ3 (Oncogene Sciences) dissolved in Dulbecco's Modified Eagle's Medium containing 4-5 g/L glucose (DMEM-LG), (ii) chondrogenic culture media (CCM) without TGFβ3 (CCM–); (iii) mesenchymal stem cell growth media (MSCGM), the standard growth media for hMSCs, consisting of DMEM-LG with 10% fetal bovine serum and 1% antibiotic-antimycotic. Cells were harvested after 1, 14, and 28 days of culture.

Cell pellet cultures served as controls for these experiments. A single cell pellet was produced by centrifuging $2.5 \times 10^5$ cells in a 15 mL centrifuge tube and culturing the pelleted cells in the tube.

Cell Viability.

Metabolic activity and cell growth were measured using the XTT kit (Biotium, USA). XTT is a tetrazolium derivative that measures cell viability based on the activity of mitochondria enzymes in live cells that reduce XTT and are inactivated shortly after cell death. XTT is reduced to a highly water-soluble orange colored product, the amount of which is proportional to the number of living cells in the sample, and can be quantified by measuring absorbance at wavelength of 475 nm.

Cells were plated onto scaffolds in 96-well tissue culture plates at 10,000 cells per well for up to 7 days. Reagents were added such that the final volume of tissue culture medium (containing 10% FBS) in each well was 0.1 ml. For one 96-well plate, 25 µl Activation Reagent was mixed with 5 ml XTT Solution to derive activated XTT solution. 25 µl or 50 µl of the activated XTT solution was added to each well and the plate incubated in an incubator for 4 hours. The plate was shaken gently to evenly distribute the dye in the wells. The absorbance of the samples was measured spectrophotometrically at a wavelength of 450-500 nm. Reference absorbance is measured at a wavelength of 630-690 nm.

Real Time Reverse Transcriptase-Polymerase Chain Reaction (RT-PCR).

RNA was isolated using a Qiagen Mini kit (Qiagen). Samples were lysed and then homogenized using QiaShredder columns (Qiagen). Ethanol was added to the lysate and the lysate was loaded onto the RNeasy silica-gel membrane. Pure, concentrated RNA then was eluted from the membrane in water.

Gene Expression Markers.

Relative gene expression analysis (QuantiTect SYBR Green RT-PCR kit, Qiagen) for chondrogenic markers (chondroadherin, type II collagen), and focal adhesion kinase (FAK) was performed using the MX4000 detection system (Stratagene). Ribosomal protein, large, PO ("RPLPO") was used as housekeeping gene.

Qiagen PCR Kit.

2× QuantiTect SYBR Green RT-PCR Master Mix (stored at –20° C.), template RNA, primers, and RNase-free water were thawed, mixed individually and placed on ice. A reaction components master mix was prepared as follows:

| Component | Volume/reaction | Final concentration |
|---|---|---|
| 2x QuantiTect SYBR Green RT-PCR Master Mix | 12.5 µl | 1x |
| Primer A | Variable | 0.5-2.0 µM |
| Primer B | Variable | 0.5-2.0 µM |
| QuantiTect RT Mix | 0.25 µl | 0.25 µl |
| RNAse-free water | Variable | — |
| Optional: Uracil-N-glyeolase, heat labile | Variable | 1-2 units/reaction |
| Template RNA | Variable | ≤500 ng/reaction |
| Total volume | 25 µl | |

Where final reaction volumes other than 25 µl were used, the volumes of 2.times. Quanti-Tect SYBR Green RT-PCR Master Mix and Quanti Tect RT Mix used were adjusted so that the ratio between them remained constant.

The master mix was mixed thoroughly and appropriate volumes dispensed into PCR tubes. Template RNA (≤500 ng/reaction) was added to the individual PCR tubes and incubated on ice for less than 30 min. The MX4000 was programmed and data acquisition performed during the extension step. A melting curve analysis of the RT-PCR product(s) between 55° C. and 95° C. was performed to verify specificity and identify of the RT-PCR products.

A standard curve was generated using various RNA concentrations, which contain substantial levels of chondrogenic markers (chondroadherin, type II collagen) and focal adhesion kinase (FAK). Two optical channels, one for SYBR Green and one for a reference dye (ROX), were used to correct for volume and plate location differences. Each template was analyzed in triplicate. Stratagene reaction tubes (Cat. No. 41002) and caps (Cat. No. 410024) were used, and fluorescence data was collected for SYBR Green. A typical thermal profile used was the following: 50° C. for 30 min (reverse transcriptase step), 95° C. for 15 min (to activate the DNA polymerase), 40 cycles of: 94° C. for 15 sec, 55° C. for 30 sec, 72° C. for 30 sec (triplicate readings of fluorescence were taken during this phase of the cycle.)

A dissociation curve was generated after the amplification cycles were completed. For the amplification plots, fluorescence was analyzed as "dRn" to generate C.sub.t values for all of the samples simultaneously. Gene expression levels were analyzed according to Mueller (Mueller, P. Y., Janoviak, H., Miserez, A. R., Dobbie, Z., *Biotechniques* 32, 1372-74 (2002)), which is incorporated herein by reference, and expressed as "mean normalized expression."

Confocal Microscopy.

Confocal fluorescence microscopy was used to obtain fluorescence images of cells cultured on fiber scaffolds. A fluorescent stain, which visualizes nuclear DNA (4',6-diamidino-2-phenylindole, DAPI, Invitrogen, USA) and the actin cytoskeleton (Alexa Fluor 488 phalloidin; Invitrogen, USA) in fixed cells was used. Fluorescence images of cells cultured on fiber scaffolds were taken with a confocal fluorescence microscope (Clsi, Nikon, Japan).

Cell Proliferation.

Cell number over time was measured using the PicoGreen assay (Invitrogen).

sGAG Synthesis.

Absorbance at 656 nm was used to measure total sulfated proteoglycan content ("sGAG") using the Blycan assay (Biodyne Science, UK).

Results

The results show that PDVF-TrFE fiber piezoelectric scaffolds are biocompatible and stimulate differentiation of hMSCs into chondrocytes, PC-12 neuronal cells into neurites; and stimulate attachment and growth of fibroblasts on the PVDF-TrFE scaffold as compared to growth of these cells under normal culture conditions.

Figure 3:
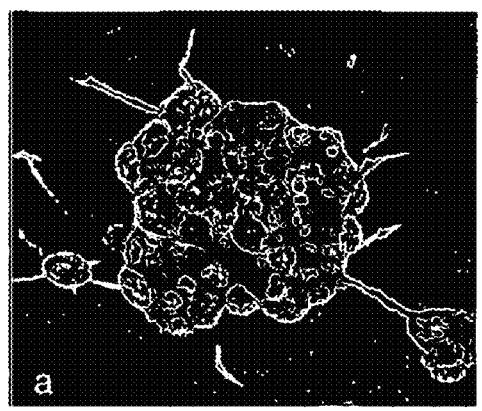
FIG. 3 shows confocal images of PC-12 cells cultured on (a) PVDF-TrFE meshes in induction media; (b) in standard growth media; and (c) PC-12 cells on PLLA meshes in induction media (60× objective D); and metabolic activity of PC-12 cells at 10 days in culture *P<0.05 for PVDF-TrFE versus collagen.
Figure 3:
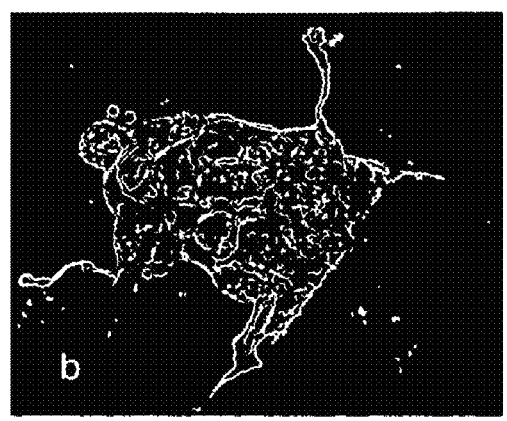
Figure 3:
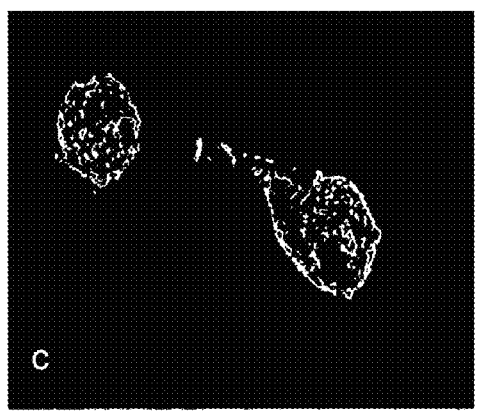
Figure 3:
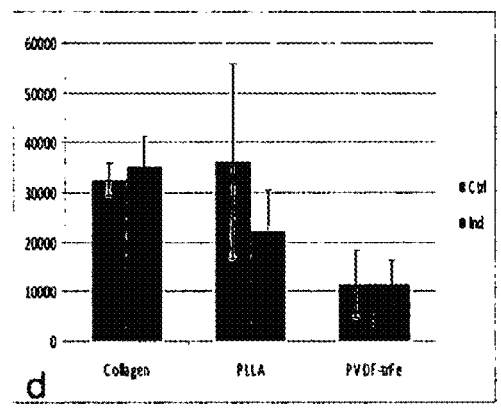

FIGS. 3a-3c shows that at 10 days in culture, extensive neurite extension on PVDF-TrFE meshes was seen with or without media containing Nerve Growth Factor (NGF). Neurite extension of cells grown on electro spun poly-L-lactic acid [PLLA] (average fiber diameter of 1.0±0.4 μm) scaffolds appeared less extensive and only occurred in the presence of NGF. As shown in FIG. 5d, cell growth, as measured by metabolic activity using the XTT kit (Biotium, USA), was significantly lower on PVDF-TrFE meshes for both growth and induction media as compared to tissue culture polystyrene and PLLA scaffolds, suggesting that PVDF-TrFE downregulates proliferation and facilitates differentiation.

Figure 4:
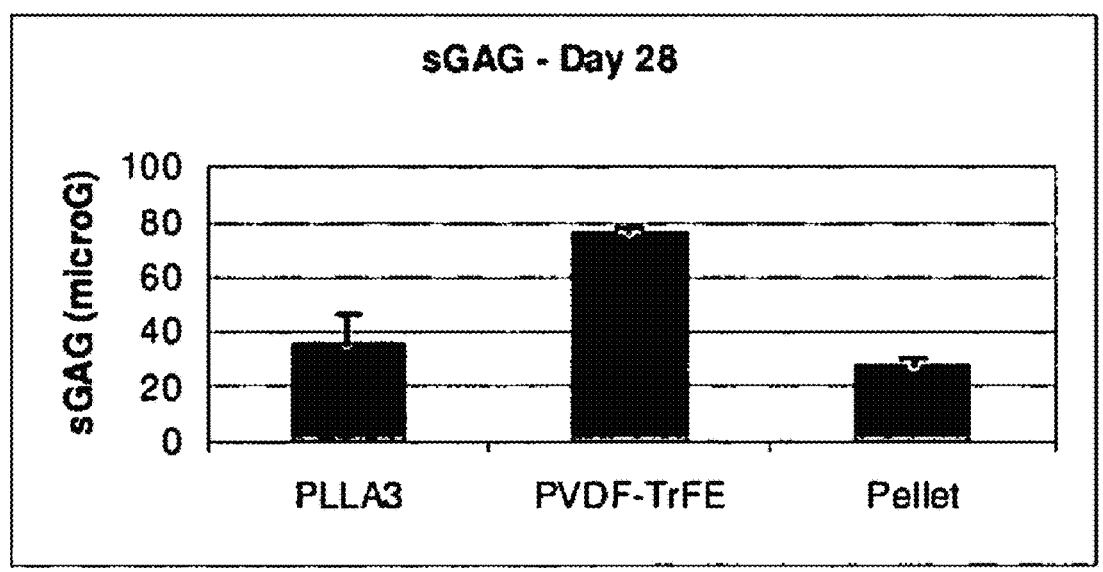
FIG. 4 shows chondroadherin and focal adhesion kinase (FAK) gene expression in human mesenchymal stem cells (hMSCs) cultured for 28 days on PLLA and PVDF-TrFE scaffolds. Cell pellet cultures serve as controls.
Figure 5:
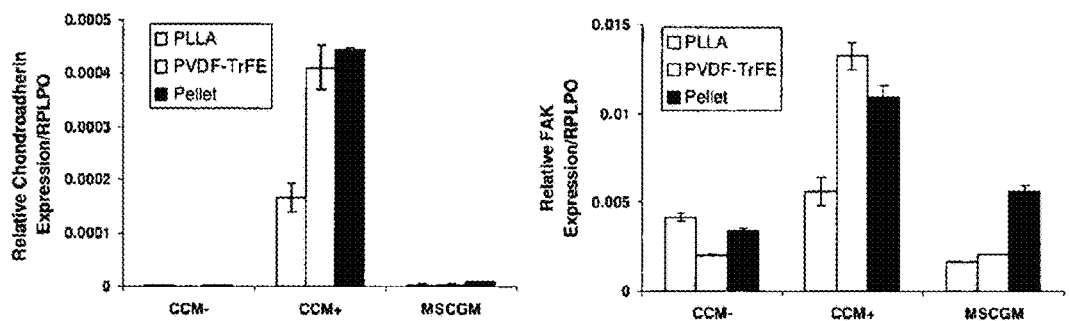
FIG. 5 shows glycosaminoglycan production (sGAG) for human mesenchymal stem cells cultured in chondrogenic induction media on PLLA and PVDF-TrFE meshes at 28 days. Pellet cultures served as a positive control. *p<0.05.

FIGS. 4 and 5 shows that for human mesenchymal stem cell chondrogenesis, glycosaminoglycan production by cells on PVDF-TrFE meshes/mats was significantly higher than for cells on PLLA or in pellet culture (positive control) in inductive media. It is known that transforming growth factor β (TGF-β) induces chondrogenesis in hMSCs and involves deposition of a cartilage-specific extracellular matrix. Barry, F. et al., *Exp. Cell Res.* 268, 189 (2001). Initial studies showed that chondrogenic markers and sGAG synthesis was significantly induced by CCM+ media. As shown in FIG. 4, the sGAG concentrations and chondroadherin/FAK gene expression was significantly higher on PVDF-TrFE as compared to PLLA scaffolds (p<0.01). However, no significant differences between PVDF-TrFE and PLLA scaffolds could be seen using CCM− and MSCGM media (chondroadherin, type II collagen, and FAK gene expression; sGAG synthesis).

Figure 6:
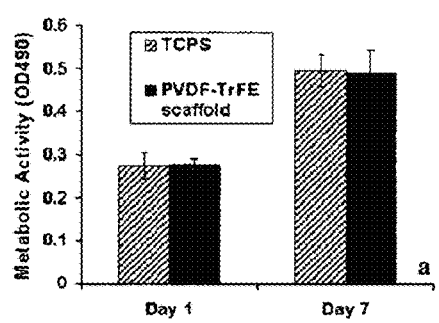
FIG. 6 shows (a) viability and growth of human skin fibroblasts on electrospun PVDF-TrFE fiber scaffold compared to tissue culture polystyrene (TCPS); (b) SEM image of electrospun PVDF-TrFE fibers.
Figure 6:
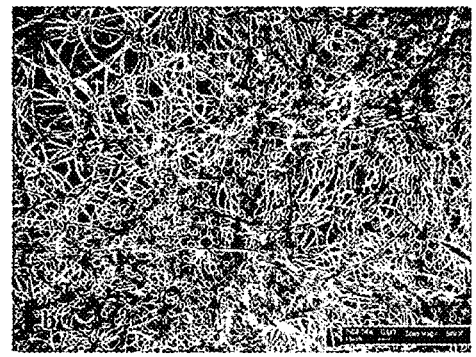
Figure 7:
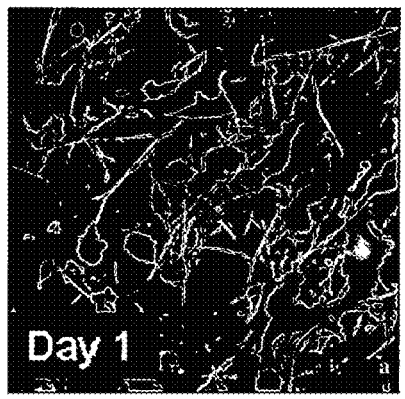
FIG. 7 shows confocal scanning laser microscopy images of human skin fibroblasts attached to PVDF-TrFE fibers after 1 day and after 7 days of cell culture.
Figure 7:
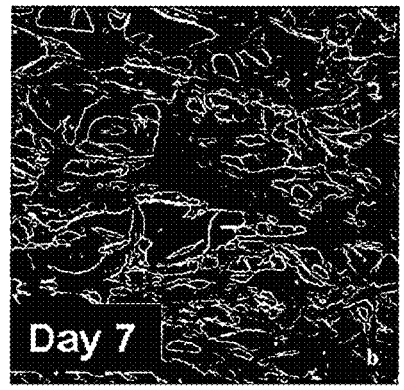

Human skin fibroblasts (ATCC number SCRC-1041) were cultured on PVDF-TrFE fiber scaffolds over a 7-day period. Tissue culture polystyrene (TCPS) served as the control). FIG. 6 and FIG. 7 show that fibroblasts grew and were well-spread on PVDF-TrFE meshes. This was comparable to growth on tissue culture plastic (positive control).

Confocal fluorescence microscopy verified the attachment and proliferation of the cells on the PVDF-TrFE fiber scaffolds. FIG. 7 shows confocal scanning laser microscopy images of human skin fibroblasts attached to PVDF-TrFE fibers after 1 day and after 7 days of cell culture. The cell morphologies of one day cultures on the fiber scaffolds are distinctly different from those of 7-day cultures. On day 1, the cells are not fully spread out. When grown on the scaffolds for a longer time (7 days) cells exhibit a more elongated and spread-out morphology.

Example 4: PC12 and DRG Culture

For one embodiment of the present invention the scaffolds were pre-conditioned in cell culture media for one day prior to seeding. PC12 cells were seeded at $0.18 \times 10^6$ cells/cm$^2$ on to the scaffolds and collagen coated plates (control) and were cultured in either control media or induction media containing neural growth factor (NGF, 250 ng/mL) a day after. PC12 cells were stained with Phalloidin (cytoskeletal stain, Invitrogen) and proliferation was evaluated by MTT cell proliferation assay (Invitrogen) at day 10 and 14.

In an exemplary embodiment of the present invention, DRGs isolated from E15 embryonic rat pup were plated on the scaffolds and stained with Vybrant® CFDA SE cell tracker (Invitrogen, Carlsbad, Calif.) at day 3.

Average fiber diameter in this exemplary embodiment of electrospun PVDF-TrFE was 0.75 μm±0.08. Directional fiber orientation was observed in the aligned scaffolds (FIG. 1). Crystallization (data not shown) and melting point of electrospun PVDF-TrFE (148.1° C.) were shifted to a higher temperature as compared to the unprocessed powder (146.1° C.) (FIG. 2). Current movement occurred just before melting in the unprocessed powder (FIG. 2a). Current movement started at 65° C. and continued before the melting in temperature of electrospun PVDF-TrFE (FIG. 2b). The 35° C. peak is the spontaneous relaxation of the Teflon sheets. When the mechanical deformation started, an increase in electric response occurred (FIG. 2c). Amplitude of response varied between −30 mV to 30 mV (FIG. 2d) for this embodiment of the present invention.

Figure 8:
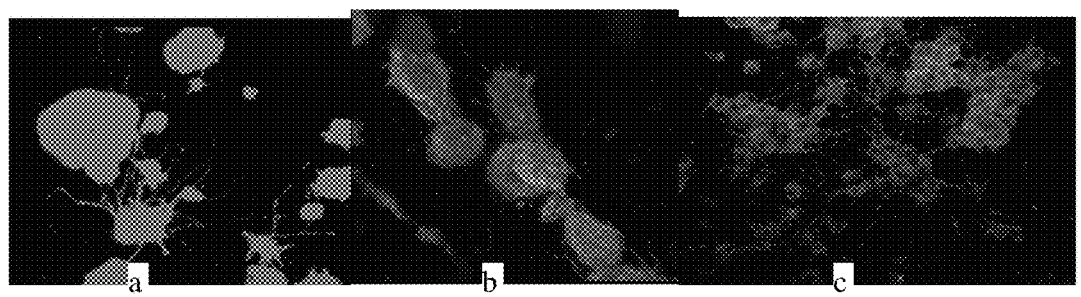
FIG. 8 depicts PC12 cells stained with Phalloidin on random (a) or aligned (b) PVDF-TrFE and collagen (c) in induction media (20×). (d) MTT viability assay for PC12 cells on random PVDF-TrFE and collagen in induction media. Cell proliferation on collagen was higher than PVDF-TrFE (p>0.05)
Figure 8:
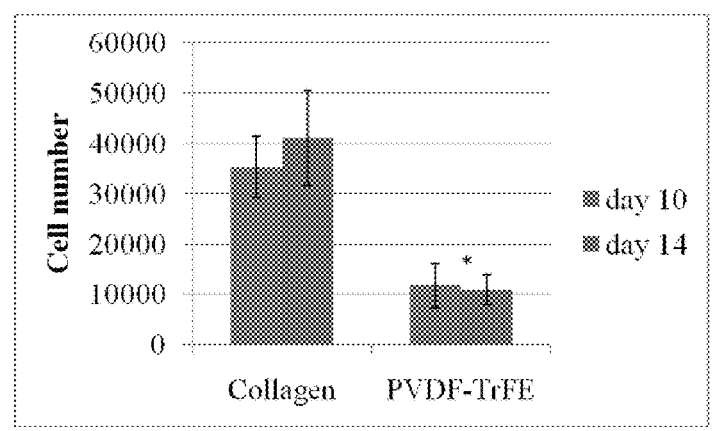
Figure 9:
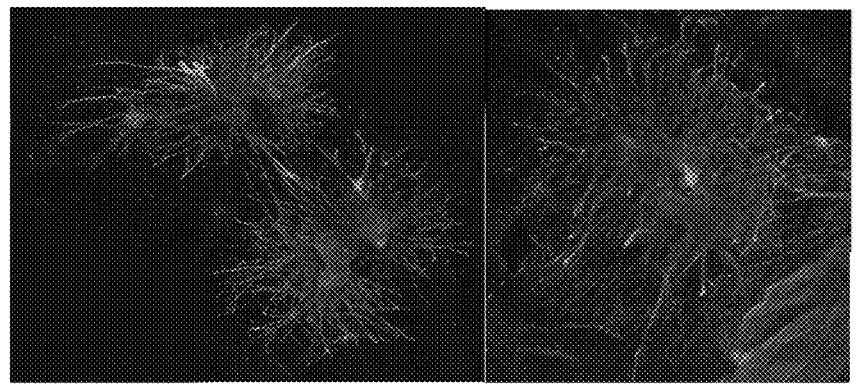
FIG. 9 depicts DRGs stained with Vybrant® CFDA SE cell tracker at day 3 on random (left) and aligned (right) PVDF-TrFE scaffolds (4×)

PC12 neurite extension was observed on both random and aligned scaffolds (FIG. 8b,d). Neurite extension both occurred along the direction of alignment (FIG. 8d) and on the collagen coated plates (FIG. 8f). PC12 proliferation was higher on collagen in the induction group on both days 10 and 14 (FIG. 8g). Proliferation in the control media was similar for both materials at both time points (data not shown). Neurite extension of DRGs was also observed on both random and aligned PVDF-TrFE scaffolds (FIG. 9).

In certain exemplary embodiments of the present invention, DSC results of unprocessed and electrospun PVDF-TrFE indicated no significant alternation occurred during the electrospinning process, as indicated by similar melting temperatures. Shifting of melting and crystallization temperature suggested extended chain crystallization during the electrospinning process. The piezoelectric phenomenon is characterized by the presence of dipole crystal structure. For certain embodiments, dipole movement would occur upon heating and could be observed as the current movement on TSDC. DSC and TSDC results of electrospun PVDF-TrFE (FIG. 2b) suggested a phase transform allowing dipole movement. Crystal structure movement upon melting contributed to the current movement in the unprocessed PVDF-TrFE powder (FIG. 2a). The electrical activity detected in these embodiments while deforming the electrospun PVDF-TrFE (FIG. 2c,d) corresponded to the observation of its piezoelectric properties.

PC12 cell proliferated and extended neurites along the direction of fiber alignment indicated the influence of contact guidance. No difference in cell proliferation was observed in control media on both days suggesting it may due to the differentiation process.

Figure 10:
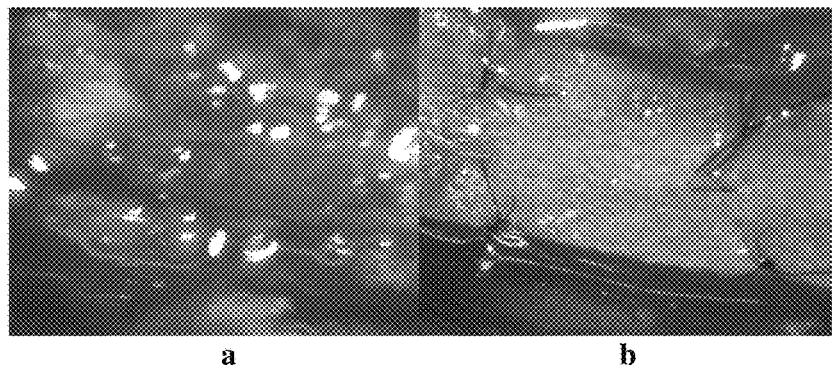
FIG. 10 depicts an image of contused spinal cord in the rat a) after contusion and b) after the insertion of the PVDF-TrFE scaffold.

Neurite extension of both PC12 cells and DRGs was observed on both random and aligned electrospun PVDF-TrFE scaffolds, suggesting its utility as a scaffold for spinal cord repair. The piezoelectric scaffolds can be implanted in contusion or transection spinal cord injury (SCI) models (FIG. 10). We are currently evaluating the scaffold seven days after contusion injury to evaluate the effect of this intervention. The contusion injury model in rats is routinely used to mimic human SCI. (21) A 200 kilodyne (kd) (1 dyne=10 uN) contusion spinal cord injury can be inducted using an infinite horizon impactor. At one week post-injury, the spinal cords will be re-exposed in all animals and scaffold constructs will be inserted into the contused area of the cords. Functional recovery can be evaluated histologically and by motor and sensory function.

Figure 11:
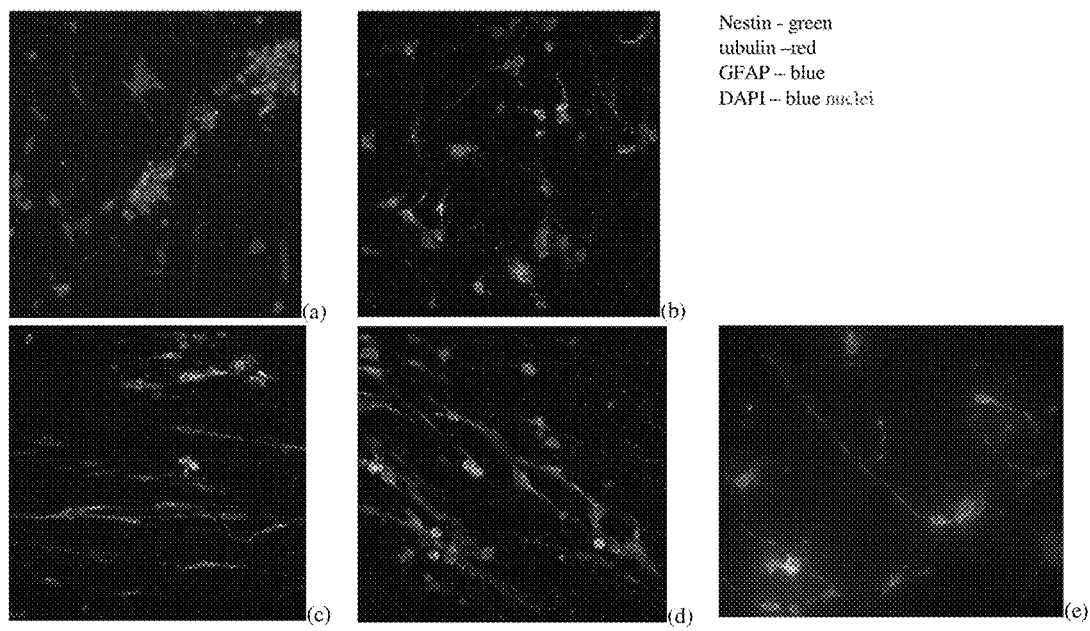
FIG. 11 provides confocal microscopy images of hNPCs on PVDF-TrFE-L a) random, b) random-annealed, c) aligned, d) aligned-annealed (all at 40× obj), and e) laminin (20× obj.)
Figure 12:
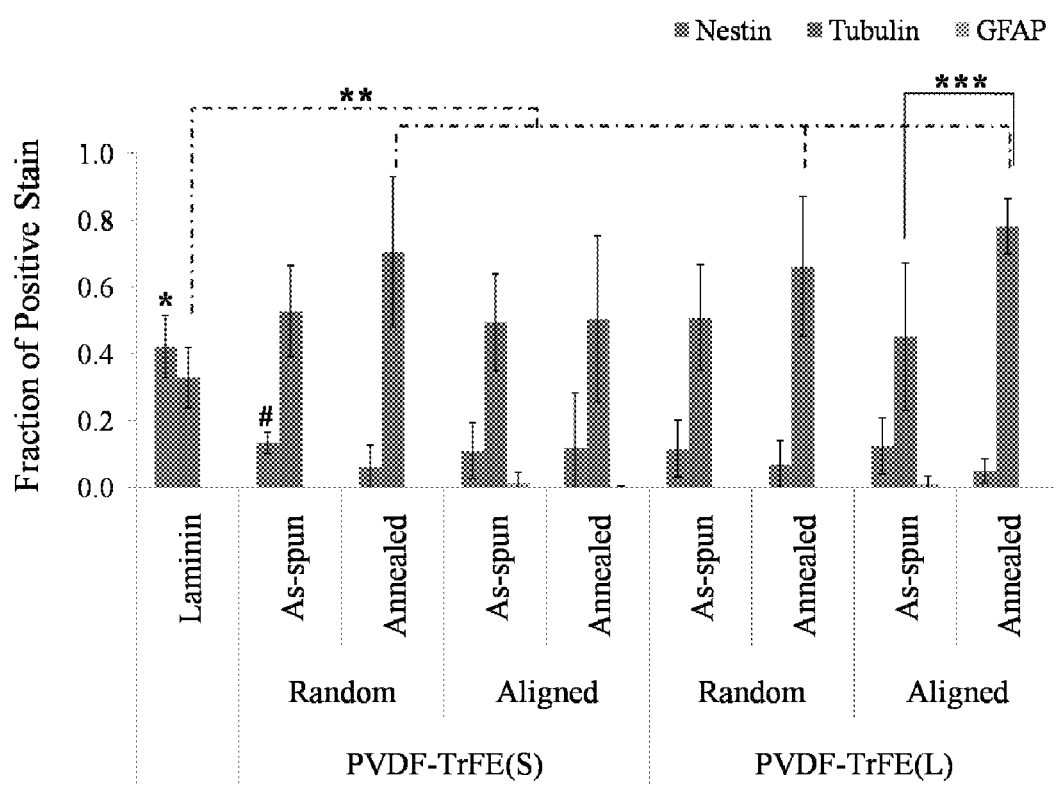
FIG. 12 Fraction of positive nestin, tubulin, and GFAP on various scaffolds. *Nestin positive cells were the highest on laminin. Tubulin positive cells were the lowest on laminin in comparison to annealed, random and aligned PVDF-TrFE (L) and annealed random PVDF-TrFE(S). *Tublin positive cells on annealed, aligned PVDF-TrFE(L) was significantly greater than as-spun aligned PVDF-TrFE(L). Very little GFAP positive cells could be detected in all of the samples.

Example 5: Evaluation of Neural Differentiation of Human Neural Stem/Progenitor Cells on Piezoelectric Scaffolds (with Reference to FIGS. 11 and 12)

This study investigates the neural differentiation of human neural stem/progenitor cells (hNPCs) on fibrous, PVDF-TrFE to determine its potential use as a scaffold in nerve repair. The piezoelectric properties of PVDF-TrFE were enhanced by annealing to increase crystal organization. Comparisons were made with laminin coated tissue culture plastic (control).

Scaffold Fabrication (Electrospinning):

Polymer solutions for electrospinning were prepared with PVDF-TrFE in methyl-ethyl-ketone (MEK) Random and aligned electrospun scaffolds were collected on a plate and a rotating drum, respectively. Annealed samples were kept at 135° C. for 96 hours and quenched with ice water.

Characterization of Thermal and Piezoelectric Properties Evaluation.

Scanning electron microscopy (SEM) images were taken to evaluate the fiber diameter and orientation. Differential scanning calorimetry (DSC) was used to evaluate thermally active transition such as melting temperature. X-ray diffraction (XRD) was performed to evaluate crystal structure of as-spun and annealed PVDF-TrFE. Thermally-stimulated current (TSC) was used to confirm piezoelectricity by measuring the current indicating the dipole movement in response to an increase in temperature. In exemplary embodiments, thermal and piezoelectric properties were evaluated using differential scanning calorimetry (DSC) and thermal stimulated depolarization current (TSDC) on both unprocessed powder and electrospun PVDF-TrFE. A heat-cool-heat cycle from −60° C. to 200° C. with heating and cooling ramp of 7° C./min was used on DSC to evaluate thermally active transition such as crystallization, melting, and phase transition. Electrospun PVDF-TrFE or the powder was sandwiched between the two Teflon films and heated from −60° C. to 140° C. for TSDC experiments [6].

Electric Response.

Electrodes (10 mm×10 mm) were attached to the ends of the scaffold using silver conductive epoxy for one embodiment of the present invention. The scaffold of this inventive embodiment was mechanically deformed at the rate of 10 mm/min using Instron. The electrodes were then connected to a custom-made amplifier circuit and the signals were recorded using Matlab.

In Vitro Study:

hNPCs (Lonza), which are cryopreserved neurospheres obtained from fetal brain tissue (20 weeks), were seeded at 45,000 cells/cm$^2$ and cultured in differentiation media (Lonza) with 25 ng/mL brain-derived neurotrophic factor (BDNF) or standard growth media for 9 days. Comparisons were made with laminin coated plates. The cells were fixed and stained with anti-Nestin (NPCs), glial fibrillary acidic protein (GFAP) (astrocytes), and neuron-specific beta-III tubulin (neuron), followed by DAPI as counter stain. 4 images were taken for each sample (n=6 per group) and positive stain was manually counted to obtain percentage of differentiation. One-way analysis of variance (ANOVA) and Tukey-Kramer test were used to determined the statistic significance between the groups ($p<0.05$).

Results.

The average fiber diameter of micron-(L) and sub-micron-(S) PVDF-TrFE were 3.32±0.2 µm and 0.75±0.08 µm, respectively. The melting point of as-spun of PVDF-TrFE (L) and (S) increased from 147.9° C. and 147.8° C. to 152.4° C. and 154.5° C. after annealing, respectively. The increase in melting temperature suggested an increase in crystallinity due to annealing. XRD results indicated an increase in the intensity of the piezoelectric beta phase at 20.4° and the loss of the non-piezoelectric alpha phase around 18.5° on the annealed in comparison to the as-spun samples. The annealing process induced crystal organization hence, enhancing the piezoelectric properties.

This study demonstrates the potential for using an electroactive scaffold as described herein for nervous tissue repair. The scaffolds enhanced neural differentiation, as indicated by a lower level of nestin positive cells on scaffolds in comparison to laminin surfaces. Neuronal differentiation may be enhanced on annealed scaffolds, which display higher piezoelectricity, as indicated by the higher fraction of cells expressing beta-III tubulin.

Example 6: Use of Electrospun PVDF as Scaffold for Bone Tissue Engineering (in Connection with FIGS. 13-19)

In this study, PVDF scaffolds were prepared by electrospinning at different voltages (12-30 kV), evaluated for the presence of the piezoelectric beta-crystal phase and its effect on biological function. Electrospun PVDF was compared with unprocessed/raw PVDF, film and meltspun fibers for the presence of the piezoelectric beta-phase using Differential Scanning calorimetry (DSC), Fourier Transform Infrared Spectroscopy (FTIR) and X-Ray Diffraction (XRD).

The cytocompatibility and osteogenic differentiation potential of human mesenchymal stem cells (MSCs) was evaluated on scaffolds electrospun at 12 and 25 kV (PVDF-12 kV and PVDF-25 kV, respectively) and compared to tissue culture polystyrene (TCP). Electro spinning PVDF resulted in the formation of the piezoelectric beta-phase with the highest beta-phase fraction of 72% for electrospun PVDF at 25 kV. MSCs cultured on both the scaffolds and TCP had normal morphology and were well spread. The MSCs seeded on PVDF-25 kV scaffolds had the greatest alkaline phosphatase activity and mineralization by day 10 when compared to TCP and PVDF-12 kV. The results demonstrate the potential for the use of PVDF scaffolds for bone tissue engineering applications.

In particular, this MSC cell study showed the osteogenic differentiation of human MSCs on both mats (i.e., the low- and high-voltage electro spun mats) was enhanced, as determined by mineralization and alkaline phosphatase activity, in comparison to cells on tissue culture polystyrene.

Introduction

In bone tissue engineering, it is desirable to have a scaffold which is osteoconductive and osteoinductive. A scaffold is considered osteoconductive if it provides a three-dimensional matrix with adequate pore size, porosity, and a surface that allows for cells to attach, proliferate and form bone tissue[1]. The electrospinning process has been widely applied for the development of scaffolds for tissue engineering applications[2]. In electrospinning process, a high electric field is applied to a polymer solution resulting in the formation of a charged jet, which is later collected as a non-woven continuous fiber on a grounded plate. Electrospun scaffolds can mimic the fibrous architecture of the natural extracellular matrix and a provide large surface area, which has been shown to directly influence cell attachment and protein adsorption for various tissue engineering applications[2]. The scaffold properties such as porosity and fiber size can be tailored depending upon polymer concentration and spinning conditions.

The osteoinductive property in a scaffold induces the differentiation of mesenchymal stem cells towards the osteogenic lineage, which may be achieved by means of physical stimuli or delivery of bioactive molecules[1]. Piezoelectric polymers are intriguing due to its capability of generating transient surface charges under minute mechanical deformation, which may influence cell behavior[3]. A commonly used piezoelectric polymer is Poly (vinylidene) fluoride (PVDF)[4-6]. PVDF is a semi-crystalline polymer that can exist in at least four polymorphs α, β, γ and δ of which α and β re of great interest. The α-phase is most readily formed during crystallization from melt below 160° C. Its chain conformation is arranged in trans-gauche-trans-gauche (TG+TG−), where net dipole moment is zero due to its antiparallel arrangement of fluoride atoms along the carbon backbone, and as a result, is the non-piezoelectric form[6,7]. The β-phase can be formed by mechanical stretching of α-phase and is also the piezoelectric form. Its chains are arranged in a planar all-trans (TTTT) conformation resulting in a large dipole moment[7,8]. Among these polymorphs, β-phase is the most sought after due to its superior piezoelectric and pyroelectric properties hence may have potential osteoinductive properties for bone tissue engineering applications.

Previous studies have primarily used PVDF films for demonstrating the influence of the piezoelectric property on cell behavior. It has also been shown that poled PVDF substrates influence endothelial cells to secrete anti-thrombotic proteins. Nevertheless, these studies were primarily performed using films or substrates. However, a three-dimensional environment is essential to facilitate spatial distribution of cells, which can later organize into bone tissue resembling in vivo bone[2,3].

In the current study, PVDF scaffolds were prepared by using a similar polar solvent, dimethylacetamide and acetone. This study demonstrates for the first time the influence of electrospinning PVDF at various voltages on the formation of β-phase and comparing the resulting crystal structures to PVDF film and melt spun fibers. In addition, this study shows for the first time the osteogenic differentiation of human mesenchymal stem cells (MSCs) on these electrospun PVDF scaffolds processed using different voltages and examines the effect of the voltage variations on cell behavior.

Materials and Methods

PVDF.

Poly (vinylidene fluoride) (PVDF) pellets (M.W. 275000), N,N-Dimethylacetamide (DMAC) and acetone were supplied by Sigma Aldrich, St. Louis, Mo. (USA).

Scaffold Fabrication by Electrospinning 20 wt. % PVDF/DMAC-acetone (1:1 by volume) solutions were prepared at 50° C. and stored at room temperature overnight prior to electrospinning. The PVDF solution was placed in a plastic syringe fitted with 18 g needle (Harvard Apparatus, MA, USA). A syringe pump (Harvard Apparatus, MA, USA) was used to feed the solution into the needle at a fixed flow rate of 0.5 ml/h. A high voltage power supply (Gamma High Voltage, FL, USA) was used to produce different voltages ranging from 12-30 kV. The electrospun fibers were collected on a grounded aluminum plate placed at a distance of 20 cm from the tip of the needle. The scaffolds were placed under vacuum for 48 hours to remove organic solvents.

Melt Spun PVDF Fibers Fabrication

PVDF was meltspun into monofilament fibers from a capillary rheometer (Instron 3211, USA) consisting of a capillary die with a diameter of 0.254 mm. Fibers were melt spun at 230° C., 240° C., 260° C., 280° C. and 290° C. at a piston speed of 2 mm/min. They were spun through air at room temperature to a take-up wheel speed of 15 m/min. After spinning, the fibers were transferred from the take-up wheel to a small bobbin.

Film Fabrication

PVDF pellets (density: 1.78 g/cm$^3$) were placed within a circular mold with approximate volume of 5 cm$^3$. The mold was then placed between preheated flat plates (280° C.) of a hydraulic press (Carver 3912, USA), which was compressed, and then cooled to form a thin film with an approximate diameter of 9.5 cm with 0.1 cm depth.

Scanning Electron Microscopy

Scanning electron microscopy (SEM, LEO 1530 Gemini, Germany) was used to evaluate the fiber morphology and average fiber diameter of the scaffolds. Mats (n of 3 per scaffold type) were sputter coated with gold palladium and viewed using an accelerating voltage of 5-10 kV and a working distance of 2 to 5 cm. Image J software (National Institutes of Health, MD, USA) was used to determine fiber size from SEM images using previously reported protocols[4].

Fourier Transform Infrared Spectroscopy

Fourier transform infrared (FTIR) analysis was performed for PVDF pellets, melt spun fibers and electrospun scaffolds (Perkin Elmer FTIR-ATR 100 series, MA, USA), and the data presented are representative of three independent samples and runs. The samples were scanned from 400 to 1500 cm$^{-1}$ with a resolution of 4 cm$^{-1}$ and total of 40 scans.

Previously described procedures were used to determine the relative fraction of β-phase present in each sample[9-11]. Using characteristic absorption bands of α and β phases at 531 cm$^{-1}$ and 840 cm$^{-1}$, respectively, and assuming that these absorption bands follow Beer-Lambert law with absorption coefficients of $K_\alpha=6.1\times10^4$ and $K_\beta=7.7\times10^4$ cm$^2$/mol, the fraction of β-phase can be calculated using the following equation (1): where $X_\alpha$ and $X_\beta$ are the crystalline mass fractions of the α and β phases and $A_\alpha$ and $A_\beta$ correspond to absorption bands at 531 cm$^{-1}$ and 840 cm$^{-1}$, respectively.

$$F(\beta) = \frac{X_\beta}{X_\alpha + X_\beta} = \frac{A_\beta}{1.26 A_\alpha + A_\beta} \quad (1)$$

Differential Scanning Calorimetry

Differential scanning calorimetry (DSC; TA Q100, DE, USA) was used to determine the melting temperature ($T_m$) and Heat of Fusion ($\Delta H_f$) of all samples and compared with unprocessed PVDF pellet. The samples underwent a heat-cool-heat temperature cycle program with a heating and cooling rate of 10° C./minute from −70° C. to +250° C. under nitrogen purge. The DSC data presented were representative of six independent runs. The crystallinity ($X_c$) of samples was calculated using the following relation: where, $H_{fs}$ is the measured heat of fusion for melting of sample, and $H_{ft}$ is the heat of fusion for 100% crystalline PVDF. $H_{ft}$ was assumed to be 104.7 Jg$^{-1}$ [12].

$$X_c(\%) = \frac{H_{fs}}{H_{ft}} \times 100 \quad (2)$$

X-Ray Diffraction

X-ray diffraction (XRD) of all the samples was recorded on an X'pert Pro Diffractrometer (Philips PW3050/60, Netherlands). The samples were irradiated with monochromatized Cu Kα (λ=0.154 nm) X-ray source with a step size [2θ] of 0.02 and scan step time [s] of 1.0. The operating voltage and current used were 45 kV and 40 mA, respectively. The samples were scanned in the 2-theta range of 15 to 45 degrees.

In Vitro Cell Study

Human mesenchymal stem cells (MSCs) were isolated from commercially available whole bone marrow aspirates (Cambrex, Md., USA)[13]. The isolation method followed has been previously reported[13,14]. The MSCs were plated on tissue culture polystyrene flasks (Nunc, N.Y., USA) and maintained at 37° C. and 5% $CO_2$ in control medium consisting of Dulbecco's Minimum Essential Medium (DMEM; Invitrogen, USA) supplemented with 10% fetal bovine serum (Hyclone, Utah, USA), and 1% antibiotic-antimycotic (Invitrogen). The cells were harvested at 70-80% confluency and resuspended in control medium for cell seeding. PVDF scaffolds electro spun at 12 KV (PVDF-12 kV) and 25 KV (PVDF-25 kV) were cut into 6 mm diameter disks using a biopsy punch (Miltek, USA). The scaffolds were sterilized with 100% ethanol (Fisher Scientific, USA) for 20 mins and later rinsed four times with PBS. Prior to cell seeding, scaffolds were transferred to a non-adherent, 96-well polypropylene plate (Fisher Scientific). MSCs were seeded at $3\times10^4$ cells/cm$^2$ on the scaffolds and tissue culture polystyrene served as a control. The cells were cultured either in control medium or osteoinduction (OS) media. OS medium consisted of control medium supplemented with 10 mM beta-glycerophosphate (Sigma Aldrich), 50 μM L-ascorbic acid phosphate (Wako, Va., USA) and 100 nM of dexamethasone (Sigma Aldrich). Cells were harvested at days 7, 10, 14, and 21 for proliferation and differentiation assays.

Cell Proliferation

Cell proliferation was determined by DNA quantification using the PicoGreen® ds DNA assay (Invitrogen). Standards were prepared with a known number of MSCs. Standards and samples (n=5 per group per time point) were lysed with 0.1% Triton X-100 (Sigma Aldrich). An aliquot of cell lysate was mixed with an equal volume of diluted PicoGreen reagent in 1× TE buffer (1:200, Invitrogen). Fluorescent intensity was measured with a microplate reader (FLX800, Biotek Instruments, VT, USA.) at 480 nm excitation and 520 nm emission. Fluorescent intensity was correlated to cell number using a standard curve.

Alkaline Phosphatase Activity

Alkaline phosphatase (ALK) activity was measured by quantifying the conversion of para-nitrophenyl phosphate (Sigma Aldrich) to para-nitrophenol (p-NP). Samples (n=5 per group per time point) were prepared by lysing cells with 0.1% Titon X-100 and incubated at 37° C. for 30 minutes. The absorbance was read at 405 nm with a microplate spectrophotometer (Emax, Molecular Devices, CA, USA). The ALK activity was normalized to cell number and expressed as nmol of p-Np/min/cell.

Mineralization Assay

Mineralization of the extracellular matrix was measured using a calcium detection kit (Fisher Scientific). Briefly, 0.5 N HCl was added to the samples (n=5 per group per time point). The calcium standards (Sigma Aldrich) were prepared at various concentrations. Samples and working solution was mixed and incubated for 3 minutes. The absorbance was read at 570 nm with a microplate spectrophotometer (Emax, Molecular Devices).

Cell Morphology

For viewing cell morphology, samples were fixed with 4% paraformaldehyde and stained using 4',6-diamidino-2-phenylindole (DAPI; Invitrogen) for the nucleus and Alexa Fluor 488 phalloidin (Invitrogen) for F-actin in the cytoskeleton. Fluorescence images of cells cultured on fibrous scaffolds were taken with a confocal fluorescence microscope (C1-si, Nikon, Japan) on days 7 and 14.

Statistics

SPSS 20.0 software (SPSS Inc., IL, USA) was used for statistical analysis of all quantitative analyses. Results are expressed as mean±standard deviation. One-way Analysis of Variance (ANOVA) and the post hoc multiple comparison using Tukey's test were applied. Probability (p) values <0.05 were considered statistically significant differences.

Results

Fiber Morphology and Diameters of the Electrospun PVDF

Figure 13:
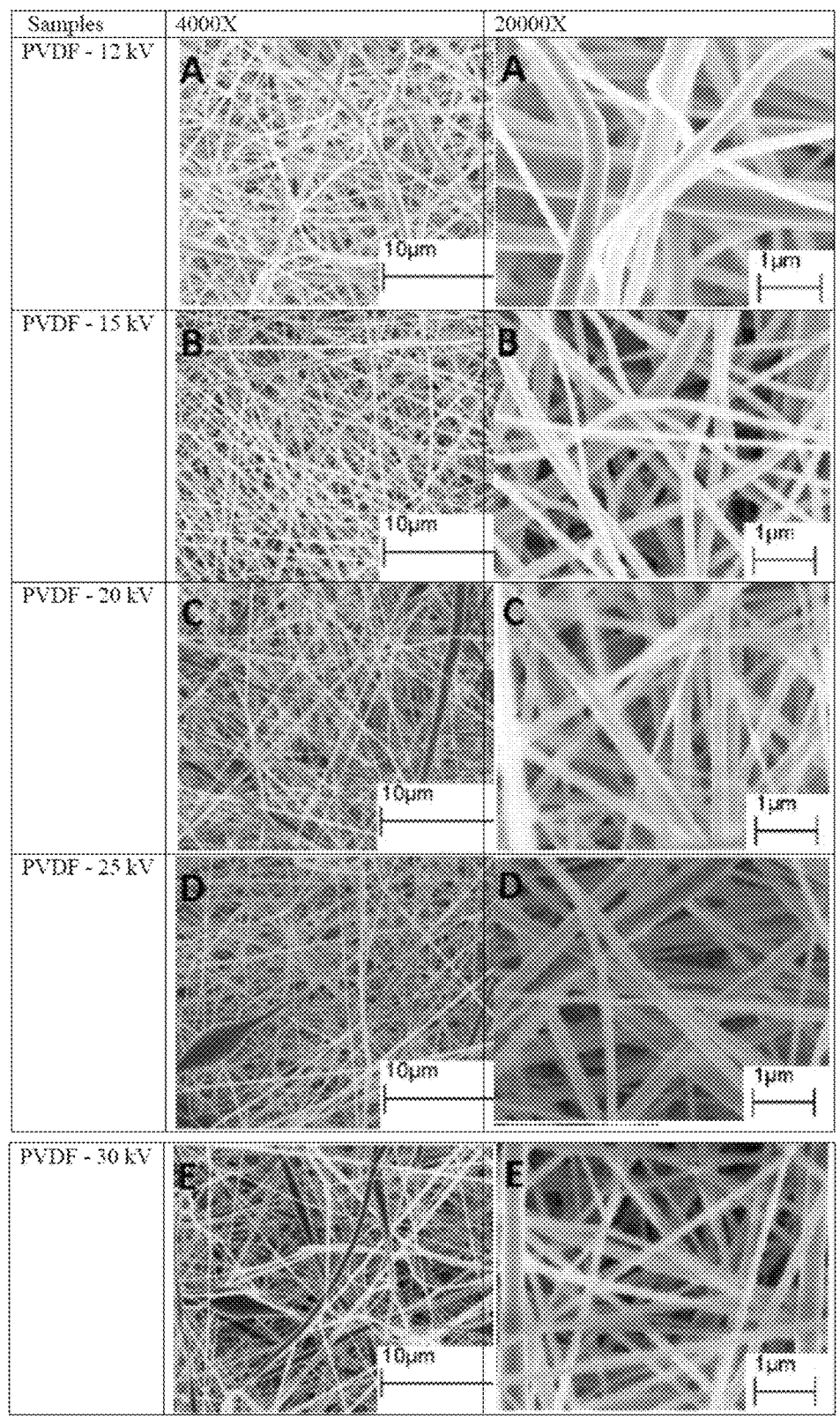
FIG. 13 shows SEM images of electro spun PVDF scaffolds (scale bar: 10 µm).

As shown in FIG. 13, nano-sized fibers were created using accelerating voltages of 12, 15, 20, 25, and 30 kV. The calculated fiber diameters are shown in the below table. Although not statistically significant, fiber diameters decreased from 295±112 nm to 151±70 nm with an increase in voltage during electrospinning.

| Samples | Fiber diameter |
| --- | --- |
| 12 kV | 295 ± 112 nm |
| 15 kV | 194 ± 72 nm |
| 20 kV | 191 ± 94 nm |
| 25 kV | 177 ± 84 nm |
| 30 kV | 151 ± 70 nm |

Above table: fiber diameter of electrospun fibers.

X-Ray Diffraction

Figure 14:
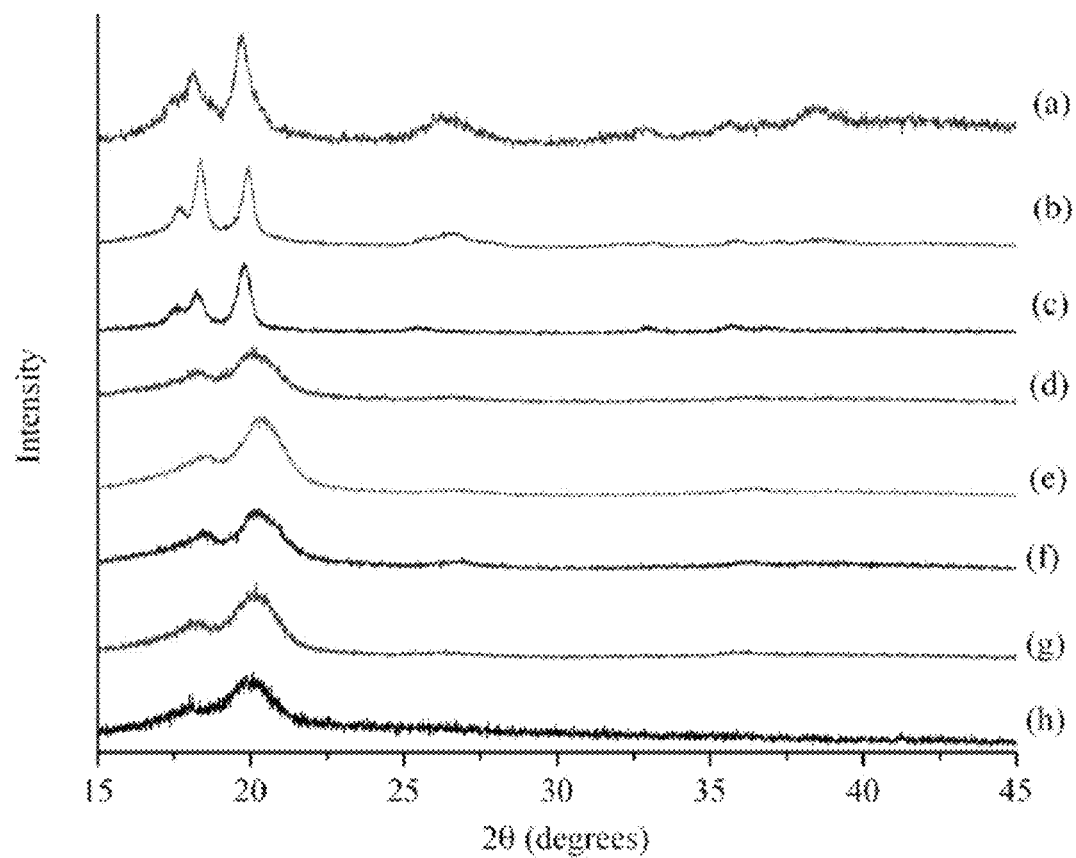
FIG. 14 shows XRD patterns of: (a) raw PVDF pellets, (b) PVDF film, (c) Melt-spun fiber at 240° C., (d) PVDF—30 kV, (e) PVDF—25 kV, (f) PVDF—20 kV, (g) PVDF—15 kV and (h) PVDF—12 kV.
Figure 15:
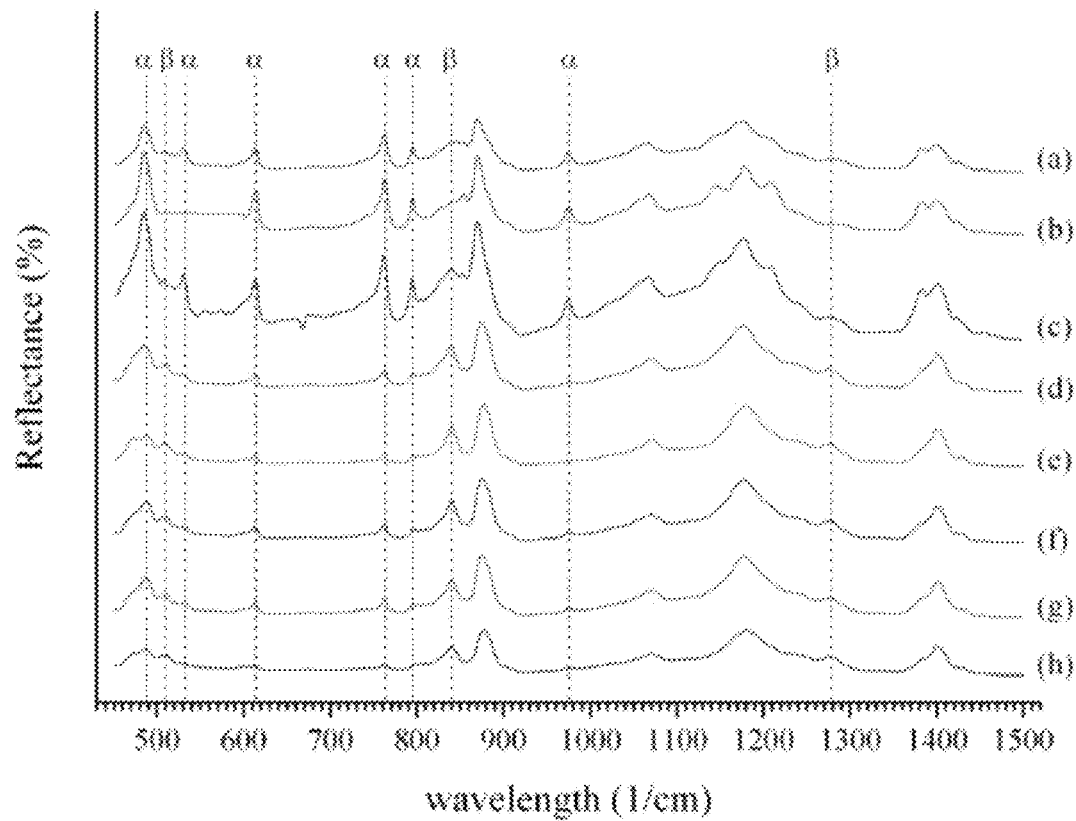
FIG. 15 shows FTIR spectra of: (a) PVDF—30 kV, (b) PVDF—25 kV, (c) PVDF—20 kV, (d) PVDF—15 kV and (e) PVDF—12 kV (f) Melt-spun fiber at 240° C., (g) PVDF film and (h) raw PVDF pellets.
Figure 16:
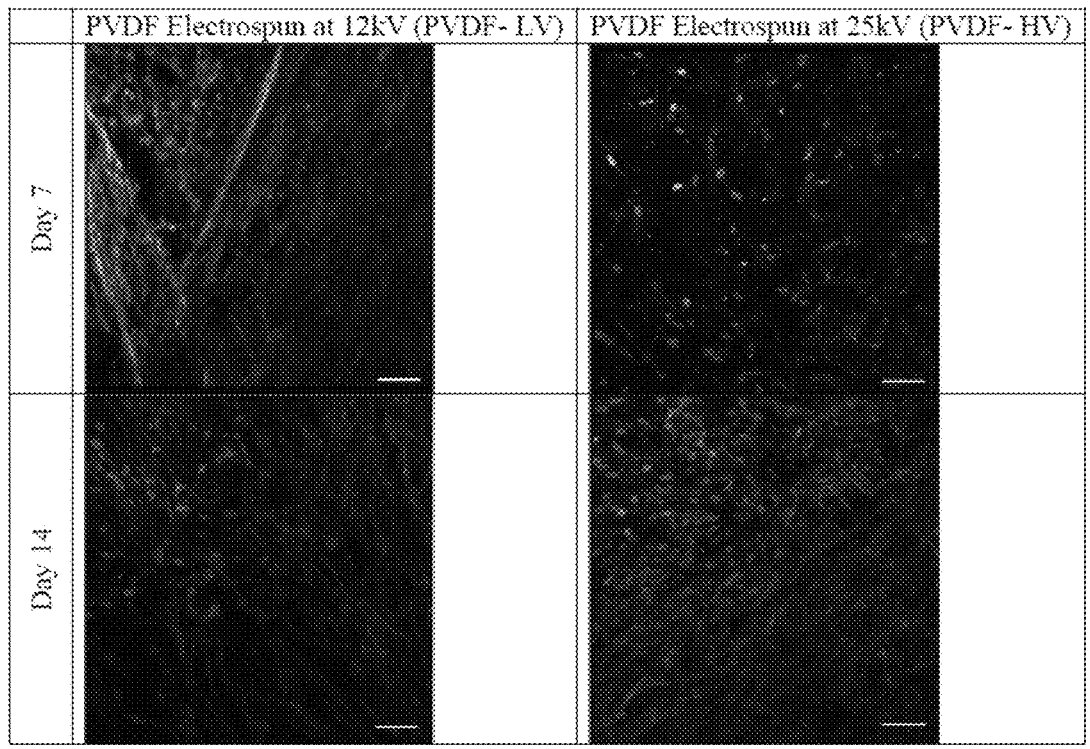
FIG. 16 shows confocal images of human MSCs on PVDF electrospun mats at day 7 and 14. Green is F-actin, and blue is nucleus, 20× objective, scale bar 100 µm.
Figure 17:
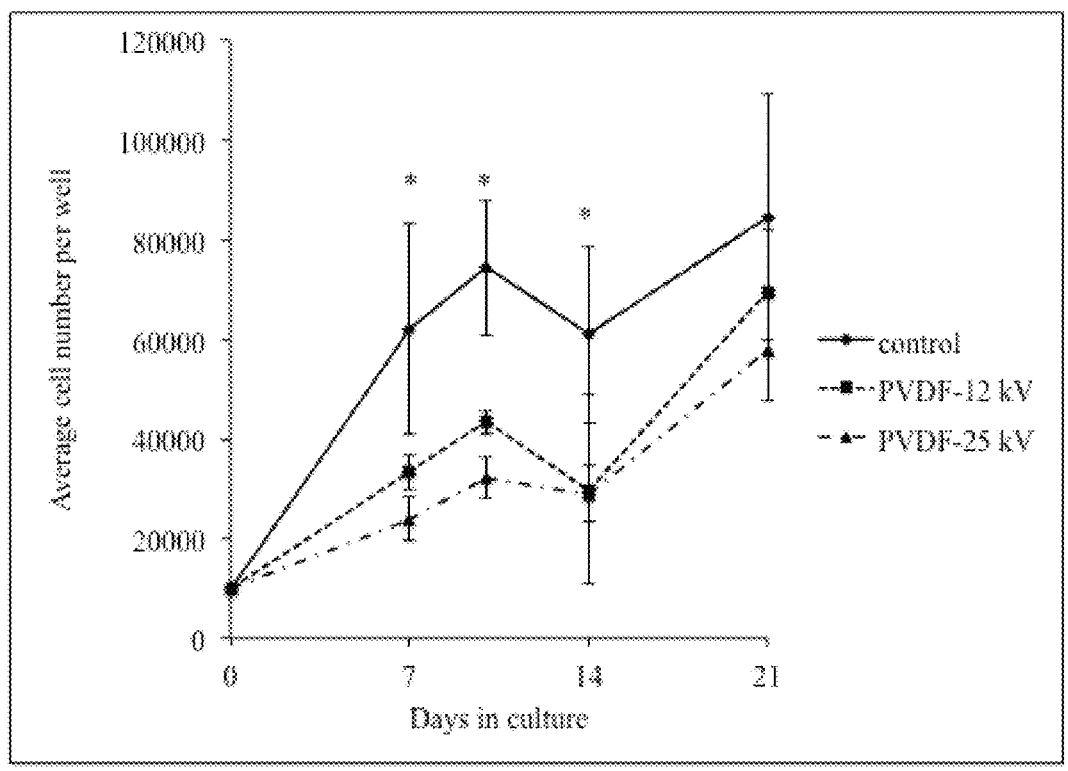
FIG. 17 depicts cell proliferation on PVDF electrospun mats versus control material. *p<0.05 significantly different between control and other groups at days 7, 10 and 14.

FIG. 14 shows the XRD patterns of all electrospun fibers, PVDF film and melt-spun fibers. For raw PVDF pellets, the XRD peaks were observed at 2θ=17.7°, 18.4°, 19.9° and 26.6° and 38.5°, which are characteristic of alpha-phase. PVDF film and melt spun fibers demonstrated similar peaks as raw PVDF pellets but had smaller to negligible peaks at 2θ=26.6° and 38.5°. The spectra of all electrospun fibers consistently showed a broad peak at 2θ=20.3° which corresponds to β-phase and a smaller broad peak at 18.4° which corresponds to α-phase.

Fourier Transform Infrared Spectroscopy

FTIR spectrum of PVDF pellets exhibited α-phase peaks located at 531, 614, 763, 796, 870 and 970 cm$^{-1}$ [8,10,15,16] (FIG. 15) Similarly, PVDF film and melt-spun fibers at 230° C. showed characteristic α-phase peaks at 614, 763, 796, 870 and 970 cm$^{-1}$. However, PVDF film did not show an α-phase peak at 532 cm$^{-1}$. A representative melt-spun fiber spectrum is shown since no differences were observed in the presence and intensities of peaks for fibers prepared at different temperatures. In contrast, the electrospun fibers consistently exhibited peaks primarily of β-phase located at 510, 840 and 1278 cm$^{-1}$. In addition, some smaller α-phase peaks were still present at aforementioned locations but the peaks at 796 and 970 cm$^{-1}$ were absent. In addition, the α-phase peak at 531 cm$^{-1}$ was absent for fibers electrospun at 25 kV. Interestingly, γ-phase peaks at 812, 882 and 1225 cm$^{-1}$ were not observed in any of the samples. From these FTIR spectra, relative fractions of β-phase in all electrospun samples were determined using equation 1, and the results are shown in the below table. The highest proportion of β-phase was achieved in 25 kV electrospun scaffolds where the fraction of β-phase was calculated to be 72.44%.

| Samples | β fraction (%) |
| --- | --- |
| 12 kV | 65.90 |
| 15 kV | 68.50 |
| 20 kV | 66.86 |
| 25 kV | 72.44 |
| 30 kV | 68.28 |

Above table: estimated relative beta-fraction for the electrospun scaffolds.

Differential Scanning Calorimetry

The DSC was performed to determine the changes in thermal properties and crystal structures for melt-spinning and electro spinning samples and were compared with raw PVDF pellets. All the samples showed similar endothermic peaks extending from 150° C. to 170° C. The melting temperature ($T_m$) and heat of fusion of these samples were determined from DSC curves as shown in the below table. The crystallinity of samples was calculated using equation 2. The results indicated lower melting temperatures for all electrospun fibers than the unprocessed PVDF pellets. The melt-spun fibers' melting temperature were similar to PVDF pellets. The electrospun fibers had statistically higher crystallinity than raw PVDF pellets and melt spun fibers.

| Scaffolds | Tm (avg) | % Xc |
| --- | --- | --- |
| Pellets | 168.58 ± 0.50 | 43.98 ± 0.81 |
| 12 kV | 165.91 ± 0.94 | 53.84 ± 1.88 |
| 15 kV | 164.24 ± 1.32 | 52.10 ± 1.42 |
| 20 kV | 165.77 ± 1.24 | 53.29 ± 2.11 |
| 25 kV | 164.74 ± 1.69 | 53.52 ± 1.66 |
| 30 kV | 164.99 ± 1.71 | 52.68 ± 1.24 |
| MS-230 | 167.27 ± 0.51 | 50.29 ± 5.25 |
| MS-240 | 167.32 ± 0.40 | 47.14 ± 1.34 |
| MS-260 | 167.22 ± 1.07 | 46.82 ± 1.20 |

Above table: DSC data of raw PVDF pellets, meltspun fibers and electrospun scaffolds samples.

In Vitro Cell Studies

Cell Morphology

The morphology of MSCs seeded on PVDF-12 kV and PVDF-25 kV scaffolds was evaluated using confocal microscopy. At day 7, cells were attached and spread on both scaffolds (FIGS. 16a and 16b). At day 14, cells appeared to have grown in number and remained well attached to both scaffolds as shown in FIGS. 16c and 16d.

Cell Proliferation

Over the course of 21 days in culture, cell proliferation was determined on TCP, PVDF-12 kV and PVDF-25 kV in control (not shown) and OS (FIG. 6) medium. The TCP group had significantly higher average cell number as compared to cells on both scaffolds at days 7, 10, and 14 ($p<0.05$) in OS medium Similar trend was observed in control medium where TCP group had significantly higher average cell number than both the scaffolds at all time points (not shown). By day 21, the average number of cells on both the scaffold groups in control and OS medium was the highest as compared to all other time points ($p<0.05$). No significant differences were detected between scaffolds at all time points in both medium conditions.

Alkaline Phosphatase Activity

Figure 18:
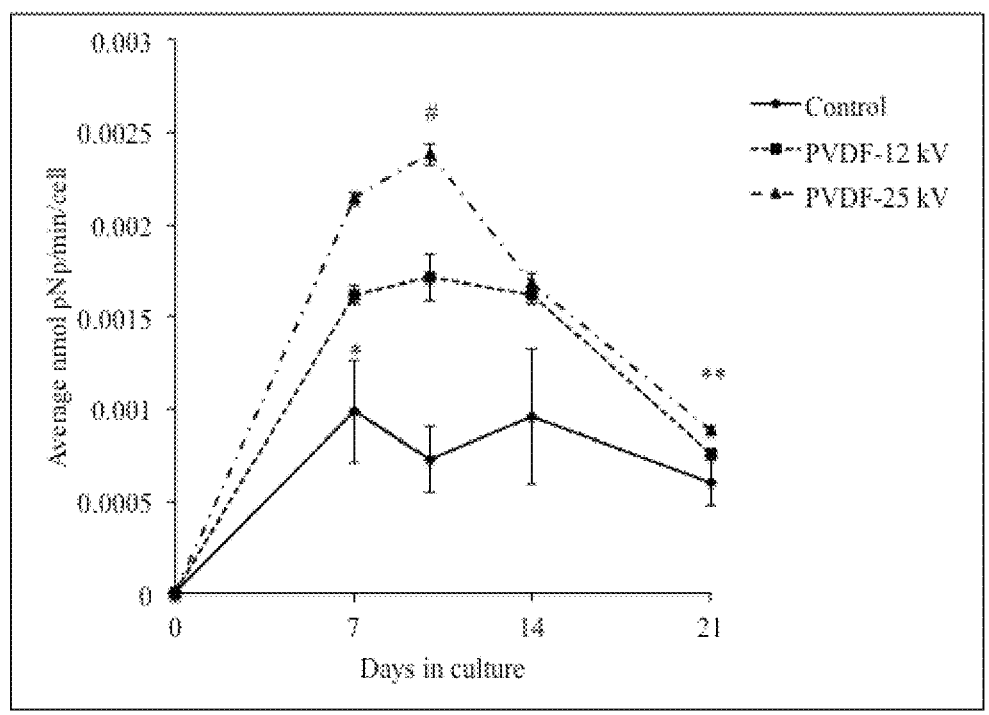
FIG. 18 Alkaline phosphatase activity normalized to cell number at different time points. *p<0.05 between control and other groups at day 7, p<0.05 between all groups at day 10, and *p<0.05 between PVDF-25 kV and control at day 21.

ALK activity, an early osteogenic differentiation marker, was determined for cells on TCP, PVDF-12 kV and PVDF-25 kV scaffolds at 7, 10, 14 and 21 days in control (not shown) and OS medium (FIG. 18). ALK activity in control medium for all groups was negligible. In OS medium, the ALK activity of cells on TCP was significantly lower than PVDF-12 kV and PVDF-25 kV scaffolds at day 7 ($p<0.05$). By day 10, all three groups were significantly different, where PVDF-25 kV scaffold had the highest ALK activity ($p<0.05$). By day 21, ALK activity on PVDF-25 kV was significantly higher than TCP group. However, there were no significant differences observed in ALK activity between both the scaffolds at 21 days.

Mineralization Assay

Figure 19:
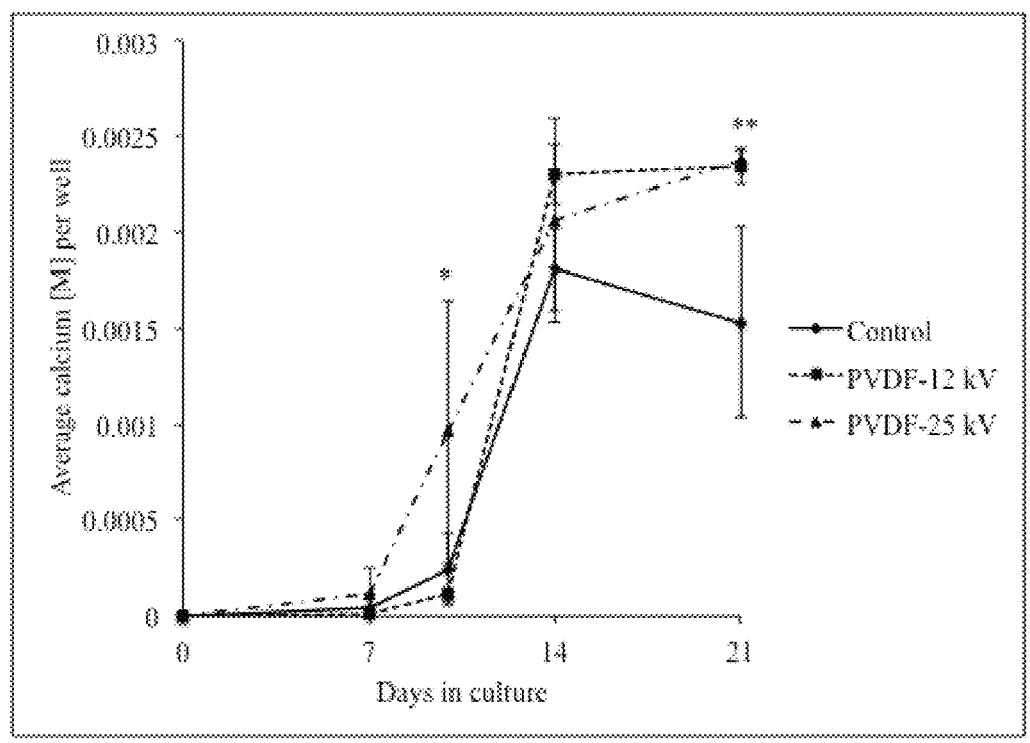
FIG. 19 Mineralization normalized to cell number at different time points. *p<0.05 at day 10 between PVDF-25 kV and other groups, **p<0.05 between control and other groups at day 21.

Mineralization/calcium, a mature osteogenic differentiation marker, was measured for cells cultured on TCP, PVDF-12 kV and PVDF-25 kV scaffolds at 7, 10, 14 and 21 days in control (not shown) and OS medium (FIG. 19). By day 10, the greatest mineralization was detected for cells on PVDF-25 kV scaffold as compared to TCP and PVDF-12 kV scaffolds ($p<0.05$). The amount of mineralization on both scaffolds increased significantly by day 21 and was higher than TCP group ($p<0.05$).

Discussion

The aim of this study was to examine the effect of varying the accelerating voltage during the electrospinning process on the formation of piezoelectric β-phase in PVDF scaffolds.

In addition, the osteogenic differentiation of MSCs was evaluated on PVDF scaffolds that were processed at different voltages. Varying applied voltage during electrospinning appeared to have an effect on β-phase content in electrospun scaffolds where the β-phase increased with increasing voltage from 12-25 kV. In addition, the fiber diameter decreased with increasing voltage. Cells on PVDF mats spun at higher voltages, PVDF-25 kV, also had the greatest ALK activity and mineralization as compared to TCP and PVDF-12 kV scaffold groups indicating favorable osteogenic differentiation of MSCs.

During electrospinning, applied voltage, solvent choice and concentration of polymer solution has a major effect in achieving bead free fibers. In this study, acetone and DMAC were used in a 1:1 ratio. Both DMAC and acetone are considered good solvents that are able to penetrate and dissolve the crystalline part of raw PVDF, which is primarily α-phase[17]. During electrospinning process, acetone evaporates at a faster rate than DMAC because DMAC has a higher boiling point (165° C.) than acetone (56° C.). It was expected that slower evaporation rate of DMAC would allow fibers to stretch and encourage transformation of α-phase to β-phase, while acetone would discourage any bead formation. The electrospun PVDF scaffolds achieved had nano-size fiber diameters ranging from 295±112 nm to 151±80 nm. Notably, fiber diameters had a broad range as noted by large standard deviation and some bead formation was also observed especially in samples electrospun at 25 and 30 kV. Similar trends have been noted previously during electrospinning process, where the nano-size fibers are primarily achieved as a result of increase in stretching under high electric field[12]. It has been implied that under the application of high voltage, the ejecting polymer solution becomes highly charged and overcomes its surface tension. As a result, a highly charged jet is ejected, which elongates due to repulsion of charges present on its surface[4,12]. In addition, ejected jets are highly unstable especially at high voltages, which have a direct effect on the rate of solvent evaporation further affecting the formation of beads versus fibers[12]. Therefore, thinner and larger ranges of fiber diameters were achieved as voltage increased.

Electrospinning at high voltage also had a direct effect on the $T_m$ and crystallinity as determined from DSC thermograms when compared with raw PVDF pellets, film and meltspun fibers. DSC analysis is not capable of discriminating between alpha and beta phases, but it can show if the crystallinity has changed, which is directly correlated to melting enthalpy and $T_m$[7]. When compared to raw PVDF pellets, melt spun fibers and film, the electrospun scaffolds all showed higher crystallinity, corresponding to the higher melting enthalpy. It can be explained that under high applied voltage combined with a slow flow rate, the polymer solution undergoes increased bending and elongation process, which directly influences the crystallization of PVDF[7,9]. Furthermore, when compared to the raw PVDF pellets, the melting peak of all electrospun scaffolds was broader implying the broad distribution of lamellar thicknesses of the α- and β-phase crystallites formed in electrospun scaffolds[7]. As a result, the broad endothermic peak may indicate the overlap of α- and β-phase melting peaks.

Crystal structure evaluation by XRD and FTIR corroborate that the electrospinning process modified PVDF crystalline phase. In XRD patterns, the β-phase is indicated by a broad peak with growing intensity as voltage increases from 12-25 kV in the electrospun scaffolds. Similarly, the relative β-phase fraction, estimated from FTIR spectrums, increased in electrospun scaffolds with increasing voltage. Whereas, the XRD and FTIR spectrums for raw PVDF pellets, film and melt spun fibers showed only characteristic α-phase peaks[8,12]. XRD for electrospun mats showed both β- and α-phases[6,11]. The broadness of beta phase peak may be due to the defects in the crystalline lattice caused by the formation of non-uniform, small crystal sizes during the electrospinning process[7,12]. In addition, it may be that electrospun scaffolds may consist of un-oriented β-phase crystals due to the electrospinning process where stretched molecular chains of PVDF solidified prematurely before forming oriented crystal structures[12].

For in vitro osteogenic differentiation evaluation, the PVDF-25 kV scaffold with the greatest relative β-phase fraction was compared to PVDF-12 kV scaffolds and TCP. In this study, TCP group had significantly higher average cell number than both the scaffolds. PVDF-12 and PVDF-25 kV scaffolds supported MSCs attachment and proliferation over a period of 21 days.

Osteogenic differentiation assays indicated that electrospun PVDF-25 kV scaffolds had the greatest ALK activity and mineralization by day 10 when compared to PVDF-12 kV and TCP groups. These differences could be attributed to the increased amount of β-phase fraction in PVDF-25 kV than PVDF-12 kV. It can be inferred that cell differentiation is sensitive to the differences in the amount of β-phase present in electrospun scaffolds, and thus affects differentiation. To confirm this, it has been previously shown that poled PVDF substrates, consisting primarily β-phase, significantly influence the differentiation of neuroblastoma cells than unpoled PVDF substrates[18]. In addition, the nanosize fibers of electrospun scaffolds offer large surface area compared with TCP, which may enhance cell attachment for osteogenic differentiation. Without being bound by theory, the differences in the β-phase fractions within the scaffolds and the cell attachment and movement on the scaffolds may elicit different levels of piezoelectricity from the scaffolds. This difference may have affected the differences observed in proliferation, ALK activity and mineralization of MSCs. Since no studies have previously reported the effect of piezoelectric scaffolds on MSCs osteogenic differentiation, it is important to further investigate the cellular interactions with such materials.

Conclusion

The electrospinning technique offers a simple method of producing piezoelectric PVDF scaffolds. Higher accelerating voltages used during the electrospinning process appears to increase the presence of the piezoelectric beta-phase. Results also suggest that the PVDF scaffolds may be conducive for osteogenic differentiation of MSCs with potential for bone tissue engineering applications. Future studies will focus on characterizing the electrical output from these electrospun PVDF scaffolds under varying deformations and elucidate cell response on these materials.

REFERENCES FOR EXAMPLE 6

1. Albrektsson T A, Johansson C J. Osteoinduction, osteoconduction and osseointegration. European Spine Journal 2001; 10:S96-S101.
2. Agarwal S, Wendorff J H, Greiner A. Use of electrospinning technique for biomedical applications. Polymer 2008; 49(26):5603-5621.
3 Martino S, D'Angelo F, Armentano I, Kenny J M, Orlacchio A. Stem cell-biomaterial interactions for regenerative medicine. Biotechnology advances 2012; 30(1):338-51.

4. Weber N, Lee Y S, Shanmugasundaram S, Jaffe M, Arinzeh T L. Characterization and in vitro cytocompatibility of piezoelectric electrospun scaffolds. Acta Biomaterialia 2010; 6(9):3550-3556.
5. Guo H-F, Li Z-S, Dong S-W, Chen W-J, Deng L, Wang Y-F, Ying D-J. Piezoelectric PU/PVDF electrospun scaffolds for wound healing applications. Colloids and Surfaces B: Biointerfaces 2012; 96:29-36.
6. Low Y K M N, Niphadkar N D, Boey F Y, and Ng K W. α- and β-poly(vinylidene fluoride) evoke different cellular behaviours. Journal of Biomaterial Science 2011; 22(12):1651-67.
7. Lund A, Hagström B. Melt spinning of poly(vinylidene fluoride) fibers and the influence of spinning parameters on β-phase crystallinity. Journal of Applied Polymer Science 2010; 116:2685-2693.
8. Yee W A, Kotaki M, Liu Y, Lu X. Morphology, polymorphism behavior and molecular orientation of electro spun poly(vinylidene fluoride) fibers. Polymer 2007; 48(2):512-521.
9. Andrew J S, Clarke D R. Effect of Electro spinning on the Ferroelectric Phase Content of Polyvinylidene Difluoride Fibers. Langmuir 2008; 24(3):670-672.
10. Salimi A, Yousefi A A. Analysis Method: FTIR studies of b-phase crystal formation in stretched of α and β phases PVDF films. Polymer Testing 2003; 22(6):699-704.
11. Gregorio R, Nociti D S. Effect of PMMA addition on the solution crystallization of the alpha and beta phases of poly(vinylidene fluoride) (PVDF). Journal of Physics D: Applied Physics 1995; 28(2):432-436.
12. Gao K, Hu X, Dai C, Yi T. Crystal structures of electro spun PVDF membranes and its separator application for rechargeable lithium metal cells. Materials Science and Engineering: B 2006; 131(1-3):100-105.
13. Briggs T, Treiser M D, Holmes P F, Kohn J, Moghe P V, Arinzeh T L.-Osteogenic differentiation of human mesenchymal stem cells on poly(ethylene glycol)-variant biomaterials. 2009;-91A(-4):-984.
14. Haynesworth S E, Goshima J, Goldberg V M, Caplan A I. Characterization of cells with osteogenic potential from human marrow. Bone 1992; 13(1):81-88.
15. Bormashenko Y, Pogreb R, Stanevsky O, Bormashenko E. Vibrational spectrum of PVDF and its interpretation. Polymer Testing 2004; 23(7):791-796.
16. Salimi A, Yousefi A A. Conformational changes and phase transformation mechanisms in PVDF solution-cast films. Journal of Polymer Science Part B: Polymer Physics 2004; 42(18):3487-3495.
17. Gregorio R. Determination of the α, β, and γ crystalline phases of poly(vinylidene fluoride) films prepared at different conditions. Journal of Applied Polymer Science 2006; 100(4):3272-3279.
18. R. F. Valentini T G V, J. A. Gardella Jr. and P. Aebischer. Electrically charged polymeric substrates enhance nerve fibre outgrowth in vitro. Biomaterials 1992; 13(3):183-190.

Example 7: Annealed PVDF-TrFE Enhances MSC Cell Number and Cell Differentiation Methods and Materials.
Scaffold Fabrication (Electrospinning).
Polymer solutions for electrospinning were prepared with PVDF-TrFE in methyl-ethyl-ketone (MEK) Random and aligned electrospun scaffolds were collected on a plate and a rotating drum, respectively. Annealed samples were kept at 135° C. for 96 hours and quenched with ice water.

Characterization of Thermal and Piezoelectric Properties Evaluation.

Scanning electron microscopy (SEM) images were taken to evaluate the fiber diameter and orientation. Differential scanning calorimetry (DSC) was used to evaluate thermally active transition such as melting temperature. X-ray diffraction (XRD) was performed to evaluate crystal structure of as-spun and annealed PVDF-TrFE. Thermally-stimulated current (TSC) was used to confirm piezoelectricity by measuring the current indicating the dipole movement in response to an increase in temperature. In exemplary embodiments, thermal and piezoelectric properties were evaluated using differential scanning calorimetry (DSC) and thermal stimulated depolarization current (TSDC) on both unprocessed powder and electrospun PVDF-TrFE. A heat-cool-heat cycle from −60° C. to 200° C. with heating and cooling ramp of 7° C./min was used on DSC to evaluate thermally active transition such as crystallization, melting, and phase transition. Electrospun PVDF-TrFE or the powder was sandwiched between the two Teflon films and heated from −60° C. to 140° C. for TSDC experiments [6].

Electric Response.

Electrodes (10 mm×10 mm) were attached to the ends of the scaffold using silver conductive epoxy for one embodiment of the present invention. The scaffold of this inventive embodiment was mechanically deformed at the rate of 10 mm/min using Instron. The electrodes were then connected to a custom-made amplifier circuit and the signals were recorded using Matlab.

Results.

The average fiber diameter of micron-(L) and sub-micron-(S) PVDF-TrFE were 3.32±0.2 μm and 0.75±0.08 μm, respectively. The melting point of as-spun of PVDF-TrFE (L) and (S) increased from 147.9° C. and 147.8° C. to 152.4° C. and 154.5° C. after annealing, respectively. The increase in melting temperature suggested an increase in crystallinity due to annealing. XRD results indicated an increase in the intensity of the piezoelectric beta phase at 20.4° C. and the loss of the non-piezoelectric alpha phase around 18.5° C. on the annealed in comparison to the as-spun samples. The annealing process induced crystal organization hence, enhancing the piezoelectric properties.

Figure 20:
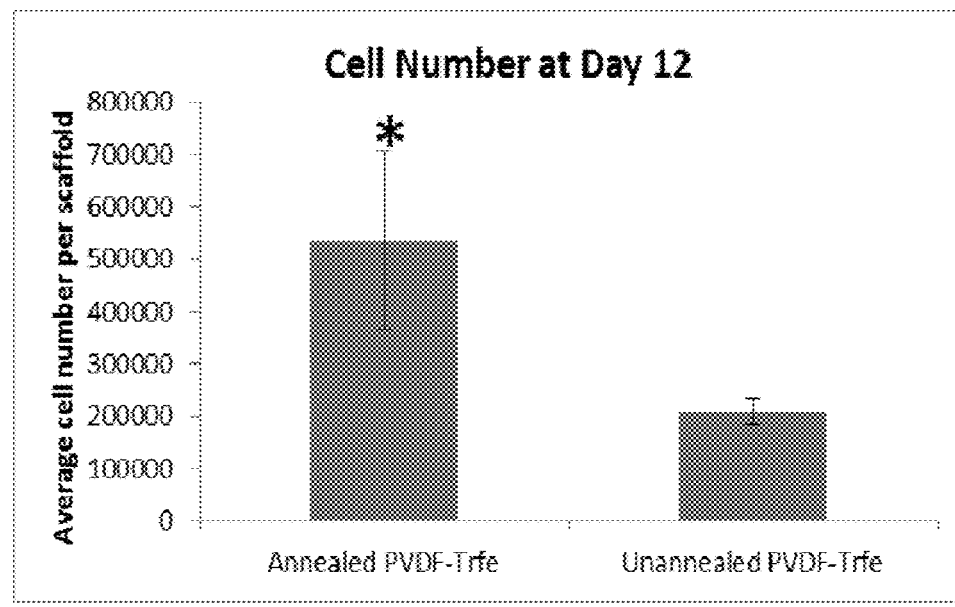
FIG. 20 shows cell number for human mesenchymal stem cells on annealed and unannealed PVDF-TrFE scaffolds in a compression bioreactor (Cartigen Compression Bioreactor, TISSUE GROWTH TECHNOLOGIES, Minnesota, US). The results show a statistically higher number of cells on annealed PVDF-TrFE (display greater piezoelectric activity) at day 12. (*p<0.05).

Piezoelectric materials display electrical activity when deformed. Human mesenchymal stem cells grown on piezoelectric materials (Annealed PVDF-TrFE) in a compression bioreactor had greater cell numbers as compared to materials that displayed less piezoelectric activity (unannealed PVDF-TrFE) (FIG. 20). Studies demonstrate for the first time that piezoelectric materials undergoing deformation may promote stem cell growth. Studies suggest that the piezoelectric property may be a beneficial feature in biomaterials to promote tissue repair.

This study demonstrates the potential for using an electroactive scaffold as described herein for bone and cartilage tissue repair. The scaffolds enhanced differentiation.

Example 8: PVDF-TrFE Scaffolds and their Use in Bone and Cartilage Tissue Engineering Introduction Musculoskeletal connective tissue injuries, specifically total joint injuries resulting from osteoarthritis or other conditions, are significant challenges to repair. Tissue engineering principles have been utilized in recent years as an approach for tissue regeneration. Tissue building during development can be imitated by combining cells and/or biological factors with a biomaterial that acts as a scaffold for tissue development. Stem cells have been sought after as the ideal cell type for tissue engineering therapies because of their ability to differentiate into various cell types and thus, promote the regeneration or repair of the diseased or damaged tissue of interest.(1;2) Increasing experimental evidence demonstrates that stem cells can adjust their properties according to their surroundings, and select specific lineages according to the cues they receive from their complex microenvironments.(3-5) Since the natural extracellular matrix of bone and cartilage, specifically collagen and glycosaminoglycan, display piezoelectric activity, we seek to investigate a piezoelectric scaffold in combination with stem cells for joint repair. Piezoelectric materials are capable of converting mechanical strain into electrical output and have been largely unstudied in the tissue engineering field.

The study examined the use of a smart material, permanently piezoelectric poly (vinylidene fluoride trifluorethylene) (PVDF-TrFE) copolymer, as a scaffold for stem cell induced cartilage and bone repair. In order to more closely mimic the structure of the natural extracellular matrix, PVDF-TrFE was fabricated into a fibrous form. Fibrous scaffolds have a beneficial structural feature for cell adhesion and growth due to their large surface-to-volume and high aspect ratios resulting from the smallness of the diameter. This structure may also enhance the piezoelectric effect due to increased surface area exposure to the surrounding milieu. To date, the use of a piezoelectric material in combination with stem cells to regenerate functional tissue has not been studied.

This study examined an in vitro model to demonstrate stem cell differentiation and to characterize the piezoelectric effect of electrospun PVDF-TrFE. The material properties of the PVDF-TrFE fibers were also studied. Therefore, in addition to developing a novel combination therapy for the repair of bone and cartilage defects, this study furthered the scientific understanding of the role of piezoelectric, or electromechanical, effects of materials on cell differentiation.

This study first aimed to fabricate and fully characterize the piezoelectric properties of the PVDF-TrFR scaffold. Piezoelectric, polyvinylidine fluoride trifluoroethylene (PVDF-TrFE) fibrous scaffolds were fabricated and characterized for electrical output in conditions that more closely mimic the biological setting. Electrical output of the scaffold was evaluated at both a local and bulk level in order to characterize the changes in electrical intensity. These findings can then be correlated with in vitro stem cell differentiation studies.

The study further aimed to investigate the osteogenic and chondrogenic differentiation of human MSCs on a piezoelectric PVDF-TrFE scaffold in vitro.

It was hypothesized that the use of a fibrous scaffold having similar physical properties as the native extracellular matrix would stimulate the differentiation of MSCs. The results obtained with this study demonstrate that human MSCs on piezoelectric, fibrous meshes grow and express enhanced levels of mature chondrocyte markers. Furthermore, on fibrous scaffolds, MSCS undergoing chondrogenesis express a reduction in markers for a more mixed phenotype. Differentiation of MSCs with or without the use of the piezoelectric scaffold was investigated using biochemical and molecular biology techniques. Transcriptional factors and markers of early and late stage chondrocytes, hypertrophic chondrocytes and osteoblasts were examined.

Background and Significance

Medicine has traditionally treated diseases or damaged tissues through drugs and/or surgery. In recent years, the approach to rebuilding tissues inside of the body or creating tissues outside of the body as in vitro models has been focused on using tissue engineering principles. Tissue building during development can be imitated by combining cells and/or biological factors (e.g. growth factors, genes) with a biomaterial that acts as a scaffold for tissue development. Cells can synthesize new tissue as well as provide the signals needed for tissue formation. Biomaterials can be designed in forms that imitate the natural organization of the extracellular matrix. Signaling molecules can be bound or incorporated into the scaffolds to aid in morphogenesis, pattern formation, and cell differentiation. Currently, however, the quality and function of many tissue-engineered therapies still need to be improved to fully address the clinical need. Innovative technologies are needed to regenerate tissues that are inherently complex for complete functional recovery. Musculoskeletal connective tissue, specifically articular cartilage and the underlying bone tissue, have been significant challenges to repair due to their complexity.

Articular cartilage has a limited intrinsic ability to heal. For this reason, orthopedic management of these lesions remains a persistent problem for the orthopedist and patient. The importance of treating injury to articular cartilage is underscored by the fact that several million people are affected in the United States alone by cartilage damage. (6) Lesions of articular cartilage typically progress to widespread cartilage destruction and arthritis that is disabling. Surgical procedures to restore articular cartilage in these lesions include debridement, abrasion arthroplasty, microfracturing, autologous chondrocyte transplantation and osteoarticular transfer.(7-9)

At present, none of these techniques have been able to restore a normal cartilaginous surface and have suffered from poor integration with the surrounding normal articular cartilage. The necessary prerequisite for a successful treatment is the integrity of the subchondral bone, which gives the joint shape and provides differentiation and development of cartilage tissue.(10) Therefore, therapy of deep osteochondral defects with a destroyed subchondral layer by one of the above-mentioned techniques leads to formation of biomechanically insufficient fibrous cartilage.

Current tissue engineering methods are aimed at filling the cartilage defects with cells or scaffolds alone, or in combination with one another.(11;12) It appears that the absence of cells leads to a poor quality reparative tissue. The use of autologous chondrocytes is the only FDA approved cell-based therapy for cartilage repair, Carticel™ (Genzyme, Inc., Cambridge, Mass.). However, of major concern is the limited proliferative capacity of differentiated chondrocytes in providing adequate cell numbers for transplantation and their proliferative capacity decreases with patient age, which poses a problem for treating age-related osteoarthritis.(13) In addition, long-term studies in patients have demonstrated that these treated defects are filled with fibrocartilage as opposed to normal hyaline cartilage, which may be a result of poor mechanical stability.(14) Adult stem cells have been sought as an alternative cell source.

Mesenchymal stem cells (MSCs) are multipotent cells that are capable of differentiating along several lineage pathways.(15) From a small bone marrow aspirate obtained from adults, MSCs can be isolated and expanded into billions of cells due to their proliferative capacity.(16) Additional characterization has also identified a panel of immunophenotypic and cell surface markers characteristic of the MSC.(17) In vitro and in vivo analyses have demonstrated that culture expanded MSCs can differentiate into osteoblasts, chondrocytes, adipocytes, tenocytes, myoblasts, and neural cell lineages. MSC populations that had been taken out to 15 passages as well as cyropreserved still have the capacity to differentiate and proliferate(18-20), suggesting that MSCs may be valuable as a readily available and abundant source of cells in the tissue engineering field. Furthermore, recent studies by the PI and others have demonstrated that the use of allogeneic MSCs can successfully repair bone and other tissue types in various animal models without provoking an adverse immune response.(21) An allogeneic MSC approach provides an off-the-shelf therapy, where allogeneic MSCs are used as universal cells and in turn, provide cells to a much larger clinical population. They are also currently in clinical trials for various disorders or conditions.

In the body, adult stem cells are often localized to specific chemically and topologically complex microenvironments, or so-called "niches". Increasing experimental evidence supports the notion that stem cells can adjust their properties according to their surroundings, and select specific lineages according to the cues they receive from their niche. (3-5) In order for an stem cell therapy to be successful in the repair of a specific tissue type, the microenvironment of the cells should be designed to relay the appropriate chemical and physical signals to them. Mimicking characteristics of the microenvironment during cartilage development may be a viable approach. During cartilage development, one of the earliest events is pre-cartilage mesenchymal cell aggregation and condensation resulting from cell-cell interaction, which is mediated by both cell-cell (neural cadherin and neural cell adhesion molecule) and cell-matrix adhesion (fibronectin, proteoglycans, and collagens).(22) Type I collagen being the predominant matrix protein present in the early stages of development is later transformed to Type II collagen by increased cell synthesis during differentiation. (23) Multiple growth factors and morphogens are also present contributing to the regulation of the differentiation process. Similarly, bone during development forms via mesenchymal cell condensation, cell-matrix adhesion and differentiation into the chondrocyte, followed by the hypertrophic chondrocyte (mineralizing chondrocyte) leading to the osteoblast.

Poorly understood physical phenomena in the in vivo microenvironment are local electric fields. Extracellular matrix materials, such as the collagens and glycosaminoglycans mentioned above, display piezoelectric activity. Specifically, they are capable of converting mechanical strain into electrical output. For type I collagen, a shear stress in the plan of polarization produces electric displacement perpendicular to the plane of the applied stress.(24) The electric fields generated in piezoelectric extracellular matrices may be solely or in part caused by cell-matrix interaction. It is well known that differentiated cells adhere, contract, and migrate/crawl in and along substrates. For these processes to occur, cells must deform the matrix. In in vitro conditions, cells contract their matrices up to 1-3 $\mu m$.(25) At the molecular scale, matrix sensing and deformation by the cell occurs via focal adhesion complexes that integrate the extracellular matrix with the actin cytoskeleton. (26-28) The force that the cell generates to deform the matrix results in signal transduction cascades leading to activation of transcription factors that affect gene expression in the cell. Recent studies by Engler et al (29) have demonstrated that MSCs are sensitive to matrix elasticity and are directed along a specific lineage. No one has studied the effects of a piezoelectric matrix, which would convert mechanical deformation or sensing by the cell into electrical activity, on stem cell function.

In order to more closely mimic the structure of the natural extracellular matrix, PVDF-TrFE was fabricated into a fibrous scaffold using the electrospinning technique. The micron to nanoscale fiber is a beneficial structural feature for cell adhesion and growth due to its large surface-to-volume and high aspect ratios resulting from the smallness of the diameters. This structure may also enhance the piezoelectric effect due to increased surface area exposure to the surrounding milieu. While structural and piezoelectric properties of PVDF-TrFE films has been widely studied and characterized, not much is known about electro spun PVDF-TrFE fibers.(39)

This study examined the use of the piezoelectric PVDF-TrFE fibrous mesh as a potential scaffold for stem cell induced cartilage and bone tissue repair. To date, the use of a piezoelectric material in combination with MSCs to regenerate functional tissue has not been studied. This study will be performed as an in vitro model to demonstrate human MSC differentiation and to characterize the piezoelectric effect. The material properties of the electrospun PVDF-TrFE nanofibers were also investigated.

Results

Fabrication and Characterization of Fibrous Arrays of PVDF-TrFE

The fabrication and characterization of electro spun, nonwoven meshes as well as studies of stem cell proliferation and differentiation on these meshes has been conducted using various polymer and ceramic compositions.(46-48) Electro spinning process produces meshes with high surface area, controllable porosity, architecture and mechanical properties. Traditional electrospinning has the limitation of producing sheet-like scaffolds or membranes due to the nature of the process, which, in turn, limits its use in vivo. In order to overcome this problem, we developed an improved electrospinning technique for the fabrication of thick, continuous electrospun scaffolds (i.e. greater than 3 mm in thickness). The technique uses a two power supply setup, in contrast to the commonly used one power supply setup (unpublished data). This novel setup creates a stronger and more focused electrostatic field, which becomes the driving force for the process.

Figure 21:
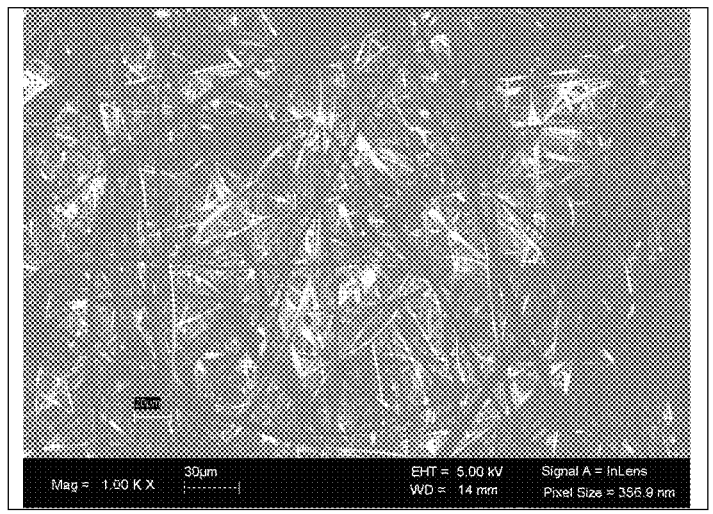
FIG. 21 shows: (A) SEM micrograph of PVDF-TrFE thick scaffolds for in vivo use and (B) confocal image of cross-section of MSCs loaded onto scaffolds. Cells are stained with DiI, a cytoplasm stain—cells appear large and rounded in morphology (40× objective).
Figure 21:
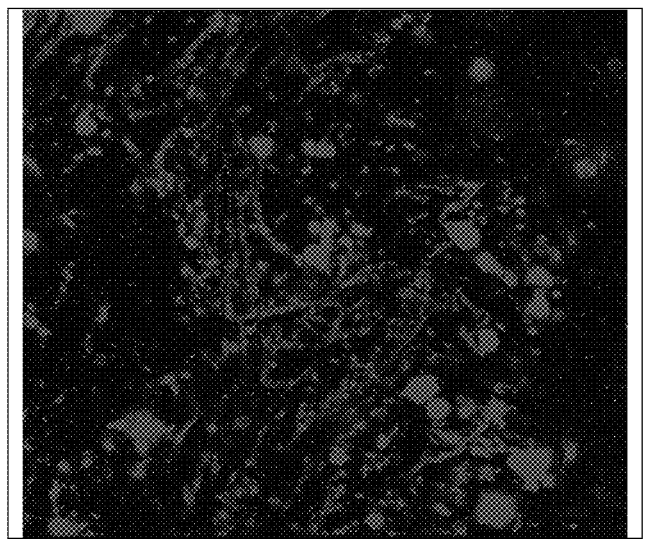

For the successful formation of fibers, spinning conditions were established (unpublished data).(49) The copolymer poly(vinylidene fluoride-trifluoroethylene) (65/35), PVDF-TrFE, was purchased from Solvay Solexis, Inc. (NJ). The electrospinning setup consisted of 25% w/v PVDF-TrFE solution in methyl ethyl ketone, 17' distance from the tip of the needle to the collecting plate, 15 mL/hr flowrate, 25 KV voltage at the tip of the needle and −1 KV at the collector plate, 15% humidity and a temperature of 20.8 Celsius. Micron-sized fibrous scaffolds were electrospun using PVDF-TrFE (FIG. 1.a.), having a mean fiber diameter of 4±0.4 $\mu m$, pore size of 28.2+18.1 $\mu m$ and porosity of approximately 80%, as determined by capillary flow porometry (PMI, Inc.). MSCs were then loaded onto the scaffolds and were determined to be evenly distributed throughout the thickness of the scaffold using confocal microscopy (FIG. 21(B)).

Structural Analysis

Differential Scanning calorimetry (DSC) determined the degree of crystalinity and confirmed the piezoelectric crystal form was present in the electrospun PVDF-TrFE mats. Comparisons were made with the piezoelectric unprocessed powder and solvent-cast film, as well as nonpiezoelectric-unpoled PVDF pellets. The Curie temperature (Tc) and melting temperature (Tm) peaks in the PVDF-TrFE polymer during the first and second heating cycle were determined. The differences in the first heating cycle between the test polymers were not detectable in the second heating cycle. This suggests that there is no chemical degradation or changes in the chemical structure due to the fabrication process. The melting points and heats of fusion for PVDF-TrFE materials were distinct from values obtained for the unpoled PVDF pellet, indicating that the piezoelectric beta-phase crystal form is present in the electrospun mat.

Thermally stimulated current (TSC) spectroscopy is widely used to understand dielectric relaxation in complex solid systems. TSC is based on the ability of polar molecules to be moved by an electric static field. TSC measurements confirmed that the electrospun PVDF-TrFE fiber scaffolds have internal charges comparable to the original piezoelectric polymer powder. There was polarization due to the applied electric field followed by a spontaneous relaxation for both the powder and electrospun forms. X-ray diffraction (XRD) and fourier transform infrared spectroscopy (FTIR) also confirmed the presence of the beta-crystal phase, which is the poled, piezoelectric phase in the electrospun PVDF-TrFE. Unprocessed and electrospun mats had similar spectrum.

Mechanical Properties

The PVDF-TrFE fibrous mats are mechanically flexible and are easy to cut using standard scissors. The mechanical properties of the micron-sized PVDF-TrFE fibrous mats, using tensile testing, were a young's modulus of 9.44±4.79 MPa., an ultimate tensile stress of 2.05±0.36 MPa., and an ultimate tensile strain of 2.48±0.22 mm/mm or 248%. These values correspond to the tensile properties of normal, human articular cartilage of the femoral condyles.(50)

Piezoresponse—Bulk Characterization

Figure 22:
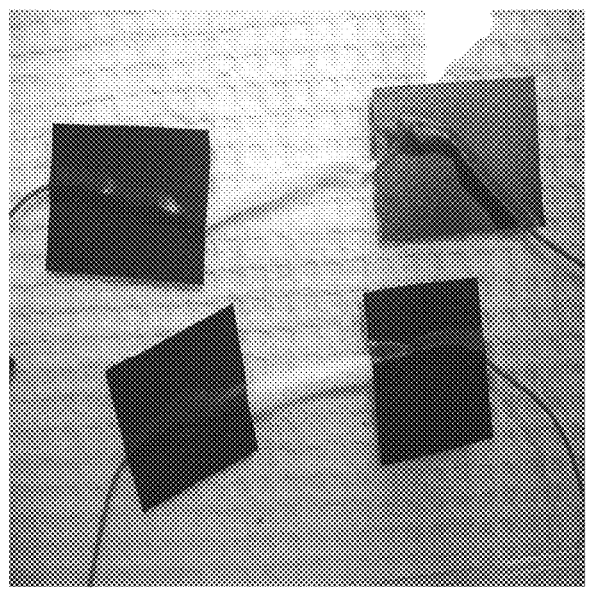
FIG. 22 shows: (A) Setup to test inverse piezoelectric effect, top is PVDF-TrFE and bottom is polyester. (B) Movement of fiber after applying AC voltage (Bar=deflection distance).
Figure 22:
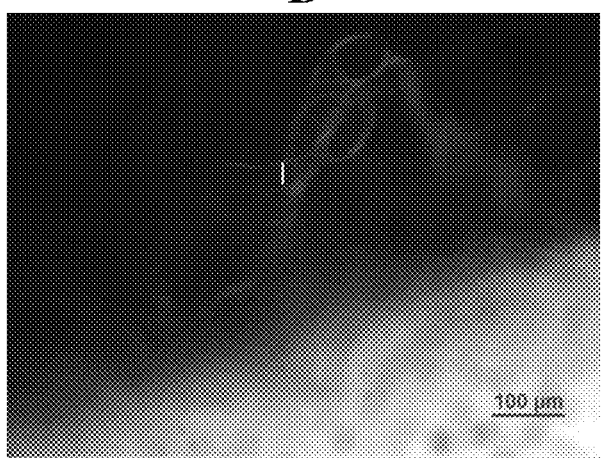

For poled PVDF-TrFe films, electrical outputs have been reported to be approximately 2.5 mV for frequencies within a physiological range(40), which correspond to a charge density of 0.8-1 $pC/cm^2$ or a film deflection of approximately 1-10 μm (41). The charge output has been shown to increase linearly with increases in deflection distance. Similarly for non-woven PVDF-TrFE electrospun meshes, electrical outputs have been reported to be approximately 2.5 mV when undergoing vibration tests at physiological frequencies.(51) These charge densities are within therapeutic range for therapies that use AC or DC voltage for wound healing. We investigated the indirect piezoelectric effect to confirm that our PVDF-TrFE electrospun meshes were piezoelectric by examining deformation in response to an applied voltage. Electrospun PVDF-TrFE and polyester (which is nonpiezoelectric as a reference) fibers were connected to an AC voltage (FIG. 22(A)). The fiber movement was recorded with a high-resolution camera (Cool SNAP $HQ^2$ from Photometrics) mounted on a microscope (NIKON SMZ1500). Sine waves with $V_{peak\ to\ peak}$=10 kV at 2 Hz were applied. Still images were taken at t=0 and t=0.5 s. The initial and final positions are shown in the FIG. 22(B) and the displacement was about 25 μm. No motion was observed for the reference polyester fiber with the same applied AC voltage.

Piezoresponse—Local Characterization at the Cellular Level

Figure 23:
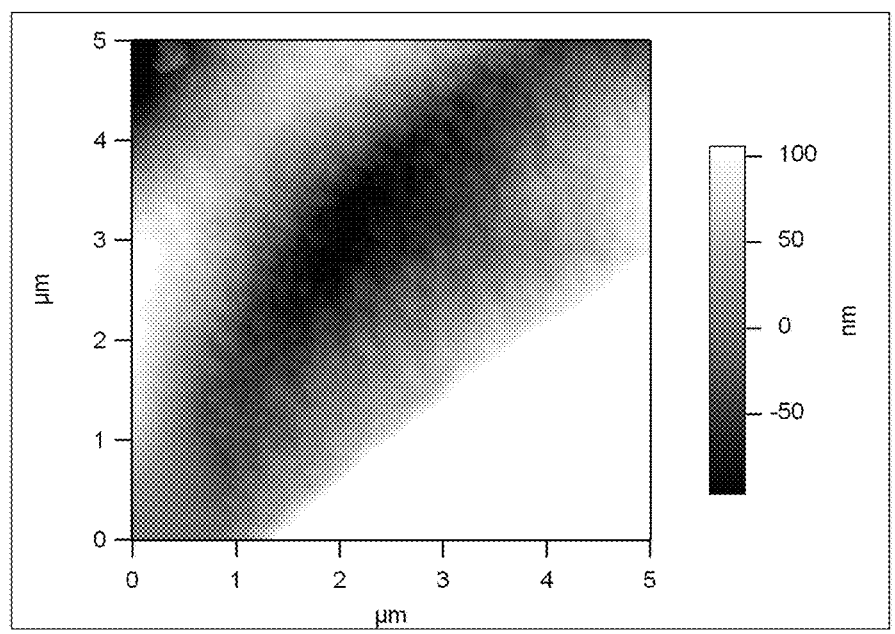
FIG. 23 shows: High resolution AFM image of piezoelectric PVDF-TrFE fiber. Nanoscale roughness was apparent.
Figure 24:
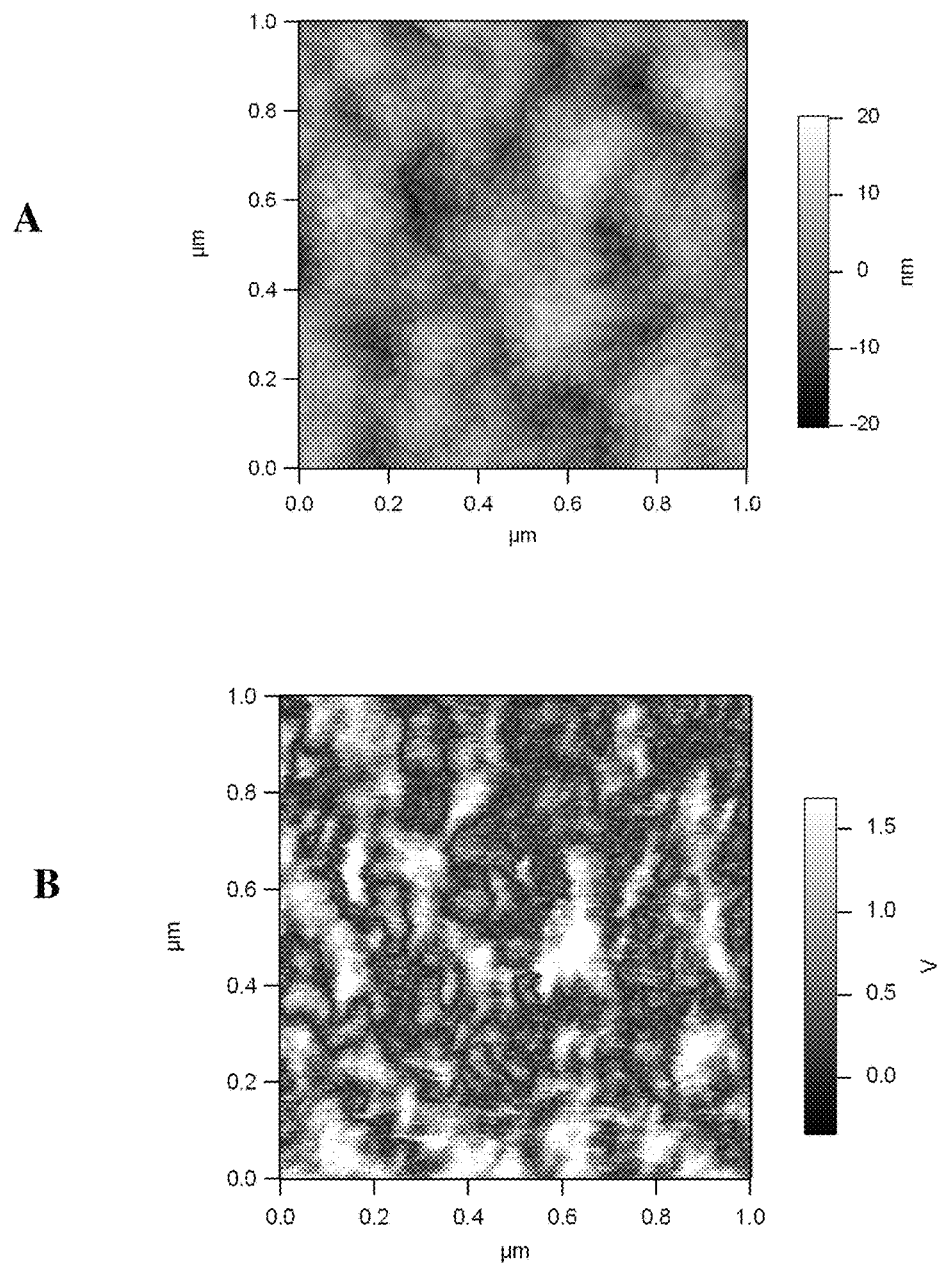
FIG. 24 shows: (A) AFM image of piezoelectric PVDF-TrFE demonstrating nanoscale roughness. (B) PFM image and corresponding PFM voltages (V) for the same area.

Without being bound by theory, it is hypothesized that the piezoelectric effect of the scaffold may be imposed via minute deformations of the fiber due to cell adhesion and/or migration, specifically in standard, static cell culture conditions and in vivo. The piezoelectric PVDF-TrFE scaffolds were characterized for electrical output at a local level in order to characterize the changes in electrical intensity. Local/minute deformations of the fibers were evaluated using a novel atomic force microscopy (AFM) technique, called piezoforce microscopy (PFM). This technique was developed recently for measuring properties of ferroelectric thin films for such applications as sensors and actuators. PFM applies an alternating voltage to the conductive tip in contact with the material surface resulting in periodic surface displacement due to inverse piezoelectric effect. Mapping of the amplitude and phase of the displacement and corresponding electrical output (voltage) can be determined. As shown in FIG. 23, the piezoelectric scaffold has a nanoscale roughness, as determined by standard AFM. The piezoresponse was detected at a 200 nm scale with PFM voltages ranging from +−1V (peak to peak) to +−5 Vpp (FIG. 24). No response was detected for nonpiezoelectric meshes.

Figure 25:
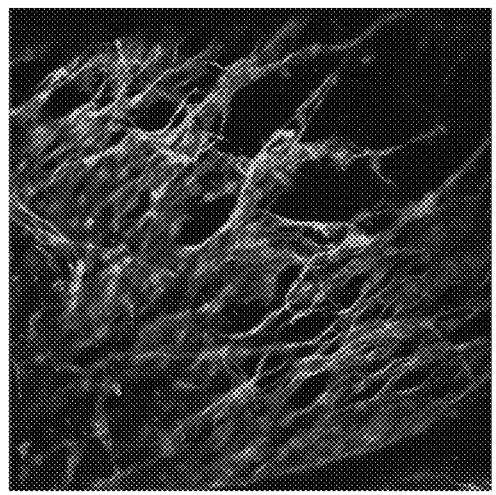
FIG. 25 shows: Confocal microscopy images of Human MSCs seeded on PVDF-TrFE meshes and cultured in (A) growth media, (B) chondrogenic induction media for 14 days in culture. FITC-phalloidin (green) for actin and DAPI (blue stain) for nucleus. 20× objective
Figure 25:
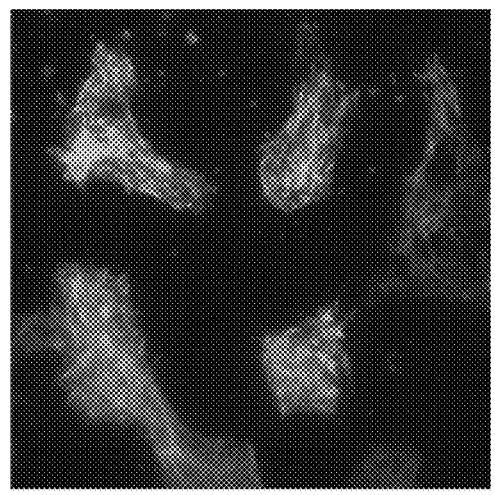
Figure 26:
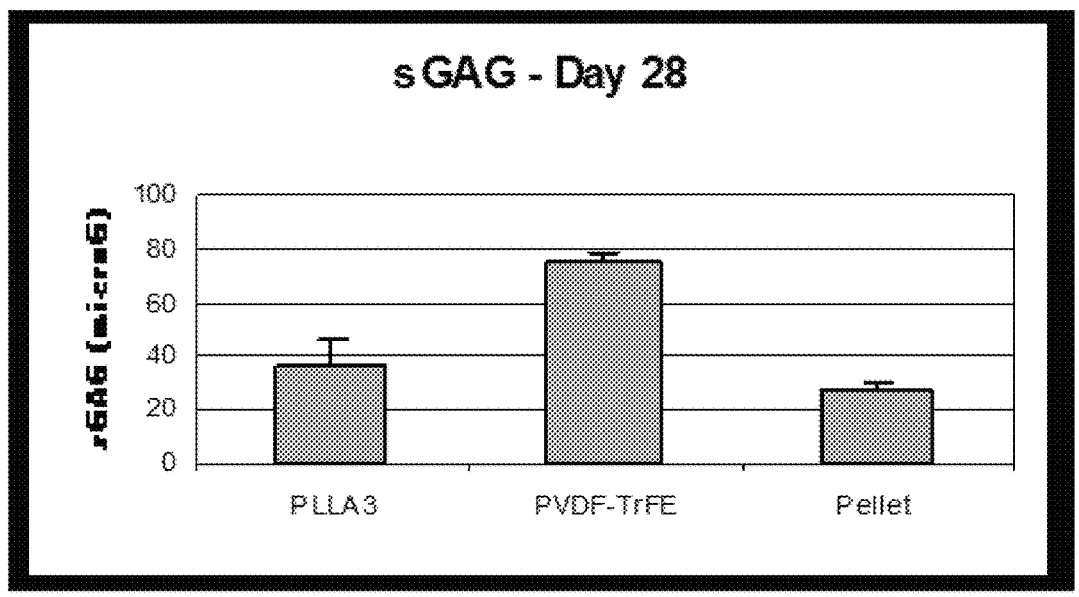
FIG. 26 shows: Glycosaminoglycan production (sGAG) for human MSCs cultured in condrogenic induction media on PLLA and PVDF-TrFE meshes at 28 days. Pellet cultures serve as positive control. *p<0.05
Figure 27:
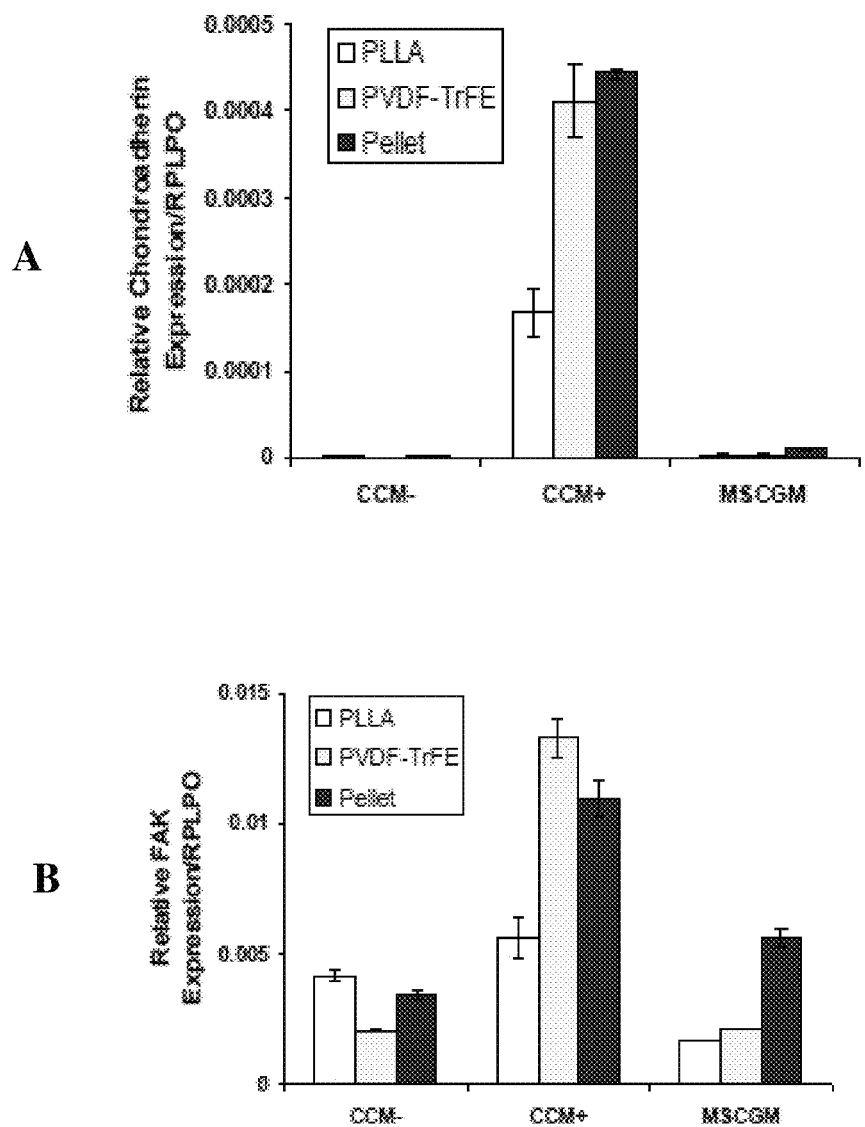
FIG. 27 shows: Gene expression of human MSCs cultured for 28 days on PLLA and PVDF-TrFE scaffolds. Cell pellet cultures served as positive control. (CCM−=condrogenic culture media without TGF-β3; CCM+=chondrogenic culture media with TGF-β3; MSCGM=standard growth media). (A) Chondroadherin, (B) FAK, (C) Sox9, and (D) Collagen Type II.
Figure 27:
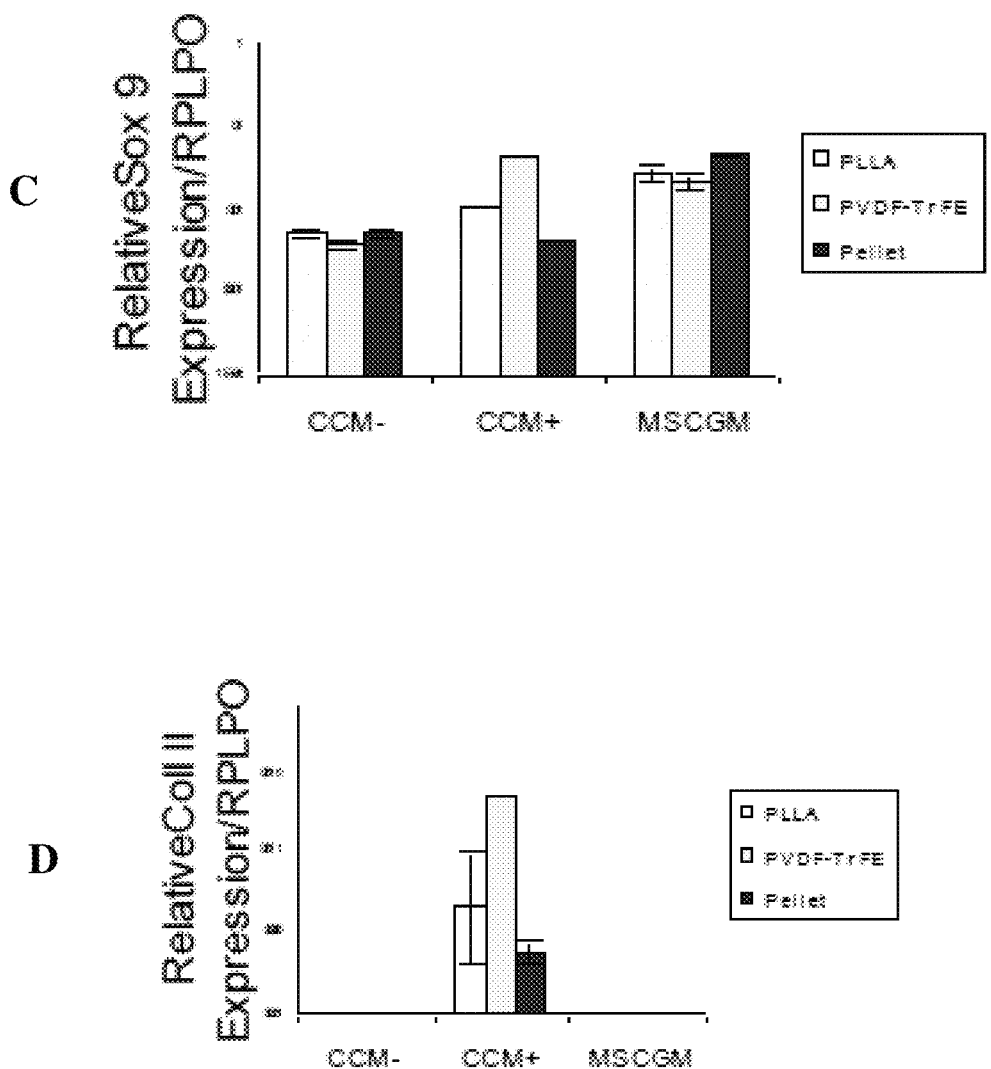

MSC Growth and Differentiation Along the Chondrogenic Lineage on PVDF-TrFE Meshes Human MSCs were seeded at a high density on PVDF-TrFE meshes and cultured in standard growth media or chondrogenic induction media. Cell growth as measured by metabolic activity and DNA was comparable to cells seeded onto poly L-lactic acid (PLLA) scaffolds, having comparable fiber diameters, and tissue culture polystyrene for up to 28 days. Cells adhered to the PVDF-TrFe mesh with a spread morphology in growth media, and in chondrogenic media, cells aggregated as shown by actin cystoskeleton organization and DAPI nuclear stain (FIG. 25). Glycosaminoglycan production for cells on PVDF-TrFe meshes was significantly higher than cells on PLLA or in pellet culture (positive control) in inductive media (FIG. 26). Greater gene expression for chondroadherin, collagen type II, focal adhesion kinase (FAK), and Sox 9, a transcription factor for chondrogenesis, was determined for cells on PVDF-TrFE meshes in inductive media (FIG. 27) as compared to cells on PLLA and pellet cultures, except for chondroadherin where values were comparable to pellet cultures. It was interesting to note that high levels of chondrocytic markers are only expressed in inductive media, suggesting electrical activity coupled with certain growth factors, such as transforming growth factor beta-3 (TGF-β3), result in a signal transduction cascade that will further promote chondrogenesis (52).

Figure 28:
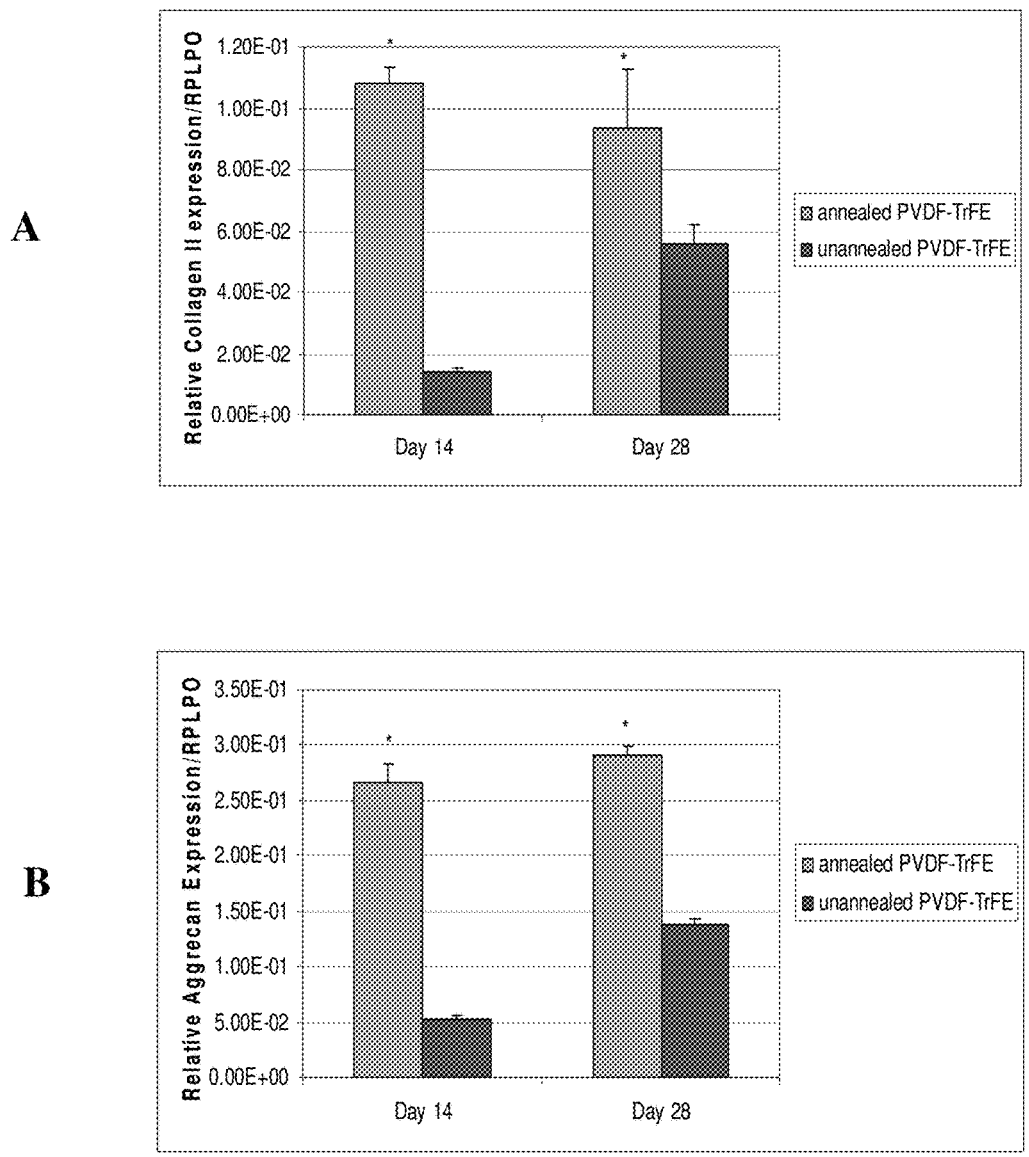
FIG. 28 shows: Gene expression of human MSCs cultured for 14 and 28 days annealed piezoelectric and unannealed PVDF-TrFE scaffolds. All cultures were in CCM+=chondrogenic culture media with TGF-β3, unless otherwise noted. (A) collagen type II, (B) aggrecan, (C) chondroadherin (D) Sox9 and (E) Sox2 (standard growth media). *p<0.05.
Figure 28:
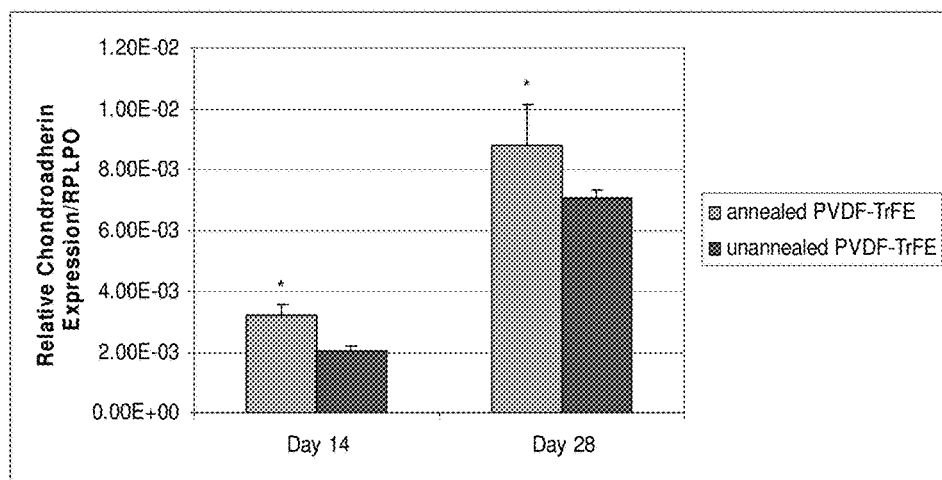
Figure 28:
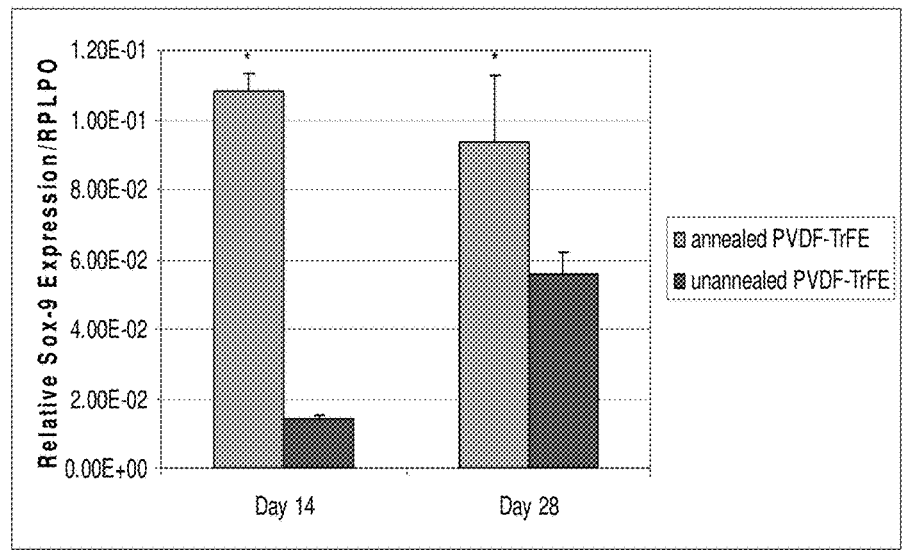
Figure 28:
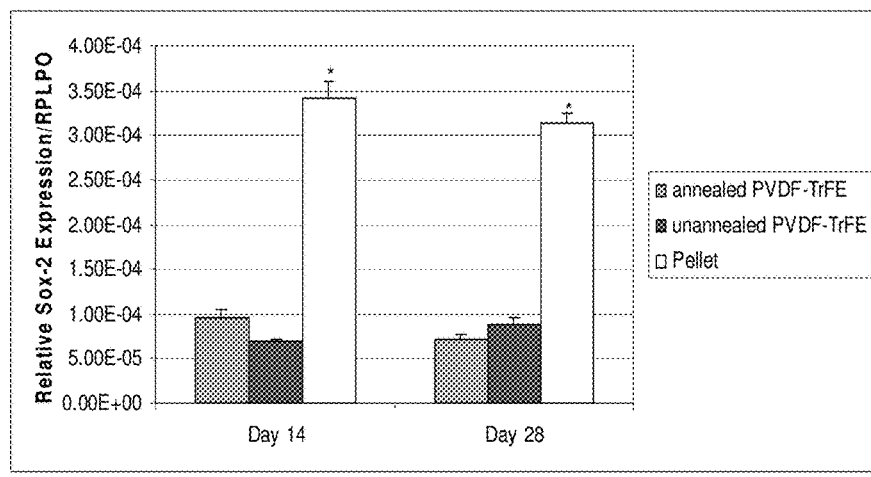

Further analysis of the gene expression of human MSCs undergoing chondrogenic differentiation on annealed PVDF-TrFE fibrous scaffolds, where annealing increases the piezoelectric beta-phase crystallinity in the material, was studied in standard static cultures. Comparisons were made with cells seeded on unannealed PVDF-TrFE fibrous scaffolds, which serves as a control substrate having the same chemistry but lower beta-phase content. Cells seeded on annealed PVDF-TrFE scaffolds expressed significantly higher levels of early and late stage markers for chondrocytes, such as aggregan, chondroadherin, collagen type II and Sox-9, as compared with cells on unannealed PVDF-TrFE (FIG. 28). This finding suggests that the piezoelectric property of the scaffold enhances chondrogenesis. It was also interesting to note that cells seeded on PVDF-TrFE scaffolds, whether annealed or unannealed, expressed lower levels of Sox-2, which is typically expressed at high levels in the MSC (undifferentiated), as compared to the standard pellet cultures. Although the pellet culture serves as a positive control, studies have reported that MSCs in pellet cultures, without the use of a scaffold, exhibit mixed phenotypes as opposed to the hyaline phenotype typically displayed by chondrocytes during chondrogenesis.(53) This data suggests that the use of a scaffold, in particular a piezoelectric scaffold, may better support the chondrogenic differentiation of MSCs as opposed to direct injection of MSCs into the cartilage defect.

Materials and Methods

Scaffold Fabrication

As described in the results, PVDF-TrFE fibrous scaffolds can be created using the electrospinning technique. The high accelerating voltage and uniaxial stretching of the viscous solution during the electrospinning process results in fibers containing a poled, piezoelectric phase.(54) An annealed PVDF-TrFE fibrous mesh can also be fabricated by heating the mesh and quenching in order to increase the piezoelectric beta-phase crystal size and crystallinity. Unannealed PVDF-TrFE will serve as a control in this study and will have the same geometry (fiber size and porosity) as the annealed PVDF-TrFE mesh. Other polymer processing techniques could be investigated to achieve fibrous structures with large pore sizes and porosities. However, electrospinning allows for a simple and efficient process to create poled scaffolds due to the large electric field applied during the process.

Structural Characterization

Meshes can be confirmed by the presence of the alpha phase or beta phase, respectively, using x-ray diffraction (XRD) and differential scanning calorimetry (DSC). Surface chemistry and morphology of meshes can be analyzed by electron spectroscopy for chemical analysis (ESCA), scanning electron microscopy (SEM) and air-water contact angle by goniometer.

The fiber size of the scaffolds can be determined from the SEM images using Image J software (National Institutes of Health, USA), as described elsewhere.(48) The porosity can be determined by using the density values of the raw material and the mat, which was adapted from a previously published protocol. The density of the electro spun mat ($D_{mat}$) can be calculated by measuring the diameter and thickness of the mat to determine the volume and the mass of the mat using an analytical balance. $D_{mat}$ can then determined by dividing the mass of the mat by its volume. Thirty samples will be measured from each mat to find the porosity of the mat. The porosity will be calculated using the formula:

Porosity (%)=$(1-D_{mat}/D_{raw})*100$, where $D_{raw}$, is density of PVDF-TrFE.

The mean pore diameter can be determined by capillary flow analysis (1100 AEX Capillary Flow Porometer, Porous Materials, Inc. Analytical Services Division, Ithaca, N.Y.). Tensile testing, using ASTM Standard D 882-02: Standard Test Method for Tensile Properties of Thin Plastic Sheeting, will also be performed to assess bulk mechanical properties.

Characterization of the Localized Electrical Activity

Localized electromechanical properties at the nanoscale can be evaluated by piezoforce microscopy (PFM), which is a specialized atomic force microscopy (AFM) technique. This technique has been developed recently for measuring properties of ferroelectric thin films for such applications as sensors and actuators. This technique was recently applied to measuring the nanoscale piezoelectric heterogeneities within individual collagen fibrils.(56) PFM applies an alternating voltage to the conductive tip in contact with the material surface resulting in periodic surface displacement due to inverse piezoelectric effect. Mapping of the amplitude and phase of the displacement at a resolution of ~3-10 nm can be achieved. Local piezoelectric coefficients will be determined. The direct voltage (charge) generating capabilities of such fibers can be determined upon deformation with specialized electromechanical characterization tools.(57) To our knowledge, this will be the first time this technique will be utilized for the application of electro spun meshes for biomedical applications. The range of deflection distances used in this technique will based on previous work where cells were observed to contract their matrices up to 1-3 µm.(25) Collagen fibrils have young's moduli ranging from 200 to 500 MPa (58) and have significant contraction/deformation in culture (59). Fiber deformations of the PVDF-TrFE scaffolds are expected since the young's moduli of the bulk fibrous samples were approximately 9 MPa and have been reported for films to be 160 MPa. Time-lapse imaging during MSC differentiation can also be performed on these scaffolds to quantify fiber deformation over time. Therefore, the data obtained here can be directly correlated to measurements determined in our culture.

Characterization of the Bulk Electrical Activity

The piezoelectric materials act as highly sensitive mechanoelectrical transducers that can generate charges in response to minute vibrational forces/deformations. In addition to the PFM characterization, the scaffold will undergo testing using a PZT (lead zirconate titanate) actuator which can be used as a cantilever beam (bimorph configuration) to measure electric output of the scaffold as function of displacement/deflection, according to previously reported protocols.(51) The electrospun PVDF-TrFE can be attached firmly to PZT actuator by applying a very thin layer of epoxy followed by a curing and setting process of the resin. The experiments can involve actuating the PZT beam by applying sinusoidal voltages of specific amplitude and frequency. The deflection of the beam can be transferred to the electrospun mat that can be attached firmly to it. The resulting strain induced in the mat will generate a voltage across its face due to the piezoelectric effect, which will be recorded along with deflection distance of the beam. Deflection distances and frequencies will correspond with frequencies and strains commonly used to characterize cartilage in dynamic compression testing(60), which can be the same setting used for the dynamic compression bioreactor studies above. The data obtained in these experiments can then be directly related to the differentiation cultures undergoing dynamic compression.

Study Design for In Vitro Differentiation Studies

Human MSCs can be evaluated for osteogenesis and chondrogenesis grown on annealed and unannealed scaffolds. Cell growth and differentiation can be evaluated using biochemical, histological and molecular biology techniques for up to 28 days. Both static and dynamic culture conditions can be examined. Findings can be correlated with electromechanical characterization results.

Cell Isolation and Culture

Human bone marrow from two healthy donors can be purchased from Lonza, Inc. or another commercial source. Bone marrow can be processed according to previously published protocols.(61) Briefly, marrow samples can be fractionated by centrifugation over a density cushion and plated on tissue culture flasks in Dulbecco's Modified Eagle's Medium (DMEM) containing 10% fetal bovine serum and 1% antibiotic (standard growth media). Cultures can be maintained at 37° C., 5% $CO_2$. Colony formation can be monitored for a 14-17 day period and then, cells can be subcultured. Cells can be examined for morphology and cell surface markers typical for undifferentiated MSCs.(15) Cells that express CD44, CD29 and SH2, and do not express CD14, CD45, and CD34 surface antigens can be verified by fluorescence-activated-cell-sorter.

Chondrogenesis and Osteogenesis Culture (Static Conditions)

The osteogenic and chondrogenic differentiation of MSCs can be evaluated on piezoelectric scaffolds. MSCs can be seeded onto annealed PVDF-TrFE and unannealed PVDF-TrFE meshes (having a thickness of approximately 100 micron), grown in standard pellet cultures (as a positive/negative control for chondrogenesis) or grown on tissue culture plastic (as a positive/negative control for osteogenesis). Scaffolds can be inserted in 96-well polypropylene plates and the pellet cultures can be grown in centrifuge tubes. They can be cultured in 1) osteogenic inductive medium (OS) consisting of standard growth medium supplemented with 10 mM beta glycerophosphate (Sigma), 50 µM L-ascorbic acid phosphate (Wako, Richmond, Va.) and 100 nM of dexamethasone (Sigma), 2) serum-free chondrogenic inductive complete medium (CCM+) consisting of 1 mM sodium pyruvate (Sigma), 0.1 mM ascorbic acid-2-phosphate (Wako), $1 \times 10^{-7}$ M dexamethasone (Sigma), 1% ITS+ (Collaborative Biomedical Products), and 10 ng/mL recombinant human TGF-β3 (Oncogene Sciences) dissolved in DMEM-low glucose, or 3) standard growth media.(62;63) These media conditions were chosen to evaluate MSC differentiation on these meshes in the presence of inductive factors or without inductive cues to determine the influence of the scaffold on differentiation.

Analysis of Differentiation

All assays can be performed at days 4, 7, 14 and 28, unless otherwise noted. Proliferation can be evaluated for all scaffold groups and controls. Proliferation and metabolic activity can be evaluated by DNA quantitation and MTT assay (as described in the results section). For chondrogenesis, chondrogenic pellets formed from MSCs and cell-laden scaffolds can be harvested and analyzed for glycosaminoglycan, Type II collagen, and proteoglycan synthesis. Glycosaminoglycan and proteoglycan synthesis can be measured quantitatively using an ELISA kit (Blyscan™ Kit, Accurate Chemical and Scientific Corporation, Westbury, N.Y.).(64) Type II collagen synthesis can be measured by an ELISA kit (Arthrogen-CIA, Chondrex, Inc.). TGF-beta3 synthesis in the culture media can be measured by ELISA kit (R&D systems). For osteogenesis, alkaline phosphatase activity can be measured by quantifying the conversion of para-nitrophenyl phosphate to para-nitrophenol (Sigma). The alkaline phosphatase activity can be normalized to cell number determined from the cell proliferation data expressed as nmol of p-Np/min/cell. Osteocalcin production will be determined using harvested samples obtained at days 14 and 28 using an ELISA assay (MetraBiosystems, Mass.).

Confocal microscopy can be utilized to visualize the cell interaction and overall morphology of the cells on the scaffolds using actin cystoskeleton stain (Alexa Fluor 488 phalloidin; Invitrogen, USA) and a nuclear stain ((4',6-diamidino-2-phenylindole, DAPI; Invitrogen, USA) for all groups.

Real-time RT-PCR can be performed as described in the preliminary results section for the gene expression of early, mid-stage and late markers of chondrogenesis and osteogenesis at days 1, 7, 14 and 28 days. For chondrogenesis, early markers of fibromodulin and cartilage oligomeric matrix protein, mid-stage markers of aggrecan and versican, mature chondrocyte markers for type II collagen and chondroadherin, and sox9, a transcription factor, can be evaluated. Additional factors that can be analyzed are Sox-2, Oct-4 and NANOG as a marker for the undifferentiated MSC, as an indicator of stem cell self-renewal and maintenance.(65)

Based on the data, TGF-beta3 can also be investigated since its expression is associated with signal transduction via the calcium/calmodulum. Its pathway becomes activated in chondrocytes during mechanotransduction when exposed to mechanical stress as well as electric fields.(33;66) Chondrocyte hypertrophic markers of Type X collagen, Type I collagen, matrix metalloproteinase 13, vascular endothelial growth factor (VEGF) and alkaline phosphatase can also be examined.(67) Gene expression at day 0 for MSCs and human articular chondrocytes (obtained from two healthy donors from Asterand, Inc.) can serve as controls. Osteogenic markers of Runx2, which is a transcription factor, osteopontin, osteocalcin as well as type I collagen can be investigated. Quantitative RT-PCR analysis can be performed with the One Step QuantiTect SYBR Green RT-PCR Kit (Qiagen, Calif., USA) using the MX4000 detection system (Stratagene, Calif., USA), according to the manufacturers' instructions. Briefly, cells can be harvested. Total RNA can be isolated using the RNeasy Mini Kit (Qiagen) including the homogenization (QIA Shredder; Qiagen) and DNA digestion step (RNase Free DNase Set; Qiagen). The reverse transcription step can run for 30 min at 50° C., followed by PCR activation for 15 min at 95° C. Forty amplification cycles can run, consisting of 15 s denaturation at 94° C., 30 s of annealing at 55° C., and 30 s of extension at 72° C. For each reaction, a melting curve analysis of the RT-PCR product can be included. Samples can be assayed and the values can be normalized to the relative amounts of the housekeeping gene RPLPO (ribosomal protein, large, PO) according to Muller et al.(68)

Protein level expression for Oct-4, Sox-2, and Nanog can be evaluated using western analysis.(65) Briefly, rabbit anti-Oct4, -SOX-2, -NANOG, and fluorescein isothiocyanate (FITC)-goat anti-rabbit can be purchased from Abcam (Cambridge, M.A.). Nuclear proteins can be extracted with the Extract kit according to the manufacturer's specified guidelines (Sigma-Aldrich). Total protein can be determined with a Bio-Rad (Hercules, Calif.) DC protein assay kit. Extracts can be treated with protease inhibitor and analyzed using 4%-20% SDS-polyacrylamide gel electrophoresis pre-cast gels (Bio-Rad). Proteins can be transferred onto membranes (PerkinElmer Life and Analytical Sciences) and incubated overnight with primary antibodies. Detection will g3 performed with HRP-conjugated IgG. Primary and secondary antibodies can be used at dilutions of 1/1,000 and 1/2,000, respectively. Membranes were stripped with Restore Stripping Buffer (Pierce, Rockford, Ill.) for reprobing with other antibodies. Cytoplasmic contamination of nuclear extracts can be determined by reprobing the membranes with anti-ribosomal protein L28.

Time-lapse Confocal Microscopy for Measuring Fiber Deformation

Cells on PVDF-TrFE scaffolds can be observed using time-lapse imaging on a confocal microscope, as previously described.(63) The goal is to observe fiber deformation in response to cell movement or attachment over time. Briefly, cells on scaffolds can be cultured in inductive and standard growth medium in 37° C., 5% $CO_2$ incubator. Cells can be harvested at time-points of days 0, 14, and 28, which correspond to assay time points in the cultures. Cells can be stained with Cell Tracker (Invitrogen) and placed in $CO_2$ independent medium (Invitrogen) for viewing on a 37° C. incubated microscope stage on a Nikon C1-si confocal system with the TE2000E inverted microscope with a HC Plan APO CS 20x/0.4 air lens. Fibers have a red autofluoresence. Images can be taken at 10 minute intervals over 18 hours. Fiber deformation distances over time can be measured using EZ-C1 analysis software. The average frequency of deformation (distance/time) can be calculated.

Dynamic Compression Cultures

Cultures subjected to dynamic compression can be performed using the C10-12c CartiGen Bioreactor System (Tissue Growth Technologies, Inc., Minnetonka, Minn., http://www.tissuegrowth.com/prod_cartilage.cfm). This bioreactor system is commercially available, specifically designed for cartilage tissue engineering projects and is simple to use (technical training and support from the company is provided). In addition, the PIs laboratory has experience using bioreactors.(69) This bioreactor applies oscillatory compressive stimulation of up to 12 samples at once in the chamber. Samples are held in separate wells so different media conditions can be used on each sample. Scaffolds of the dimension of 4 mm in diameter×5 mm thick will be used. MSCs can be vacuum loaded, as previously described(21), in order to achieve a homogeneous distribution of cells throughout the thickness of the scaffold. Cell-seeded scaffolds can then be subjected to the following parameters: dynamically tested in unconfined compression with a peak-to-peak compressive strain amplitude of 10 percent, at a frequency of 1 Hz, 3× (1 hour on, 1 hour off)/day, 5 days/week for 4 weeks.

These parameter were chosen based on reported protocols for dynamic loading of functional, cartilage tissue engineered scaffolds that mimic the in vivo conditions.(70) Both chondrogenesis and osteogenesis media conditions as well as standard growth media can be investigated. Biochemical and gene expression studies can be performed as described above for the static culture. Histological characterization can also be performed. Briefly, histological staining can be performed on the cell-laden scaffolds as well as pellets at days 7, 14 and 28. All samples can be fixed in formalin 10%, dehydrated through graded alcohols, and embedded in paraffin. Sections can be cut at a thickness of 5 μm and stained with Alcian blue, Safranin-O, and Sirius Red to detect sulfated and carboxylated acid mucopolysaccharides and sulfated and carboxylated sialomucins, proteoglycans, and different collagen types in tissue sections, respectively. Masson's trichrome stain can be used for detecting bone. H&E can also be used. Cell morphology can also be observed. Direct comparisons can be made with results from the static culture studies.

Group Size and Statistical Analyses

The experimental groups are: MSCs seeded onto annealed PVDF-TrFE and unannealed PVD-TrFE, pellet cultures, and tissue culture polystyrene. All of these groups can be cultured in either standard growth media (control), chondrogenic induction media (CCM+) or osteogenic induction media (OS). Unless otherwise stated, the quantitative assays can be performed on days 4, 7, 14, and 28 or days 1, 14 and 28 days for gene expression. A sample size, n of 6, will be used to detect statistical differences for all quantitative biochemical and proliferation assays. A sample size, n of 9, can be used for quantitative gene expression using a 96-well plate format as performed in the preliminary results section. This sample size was determined based on a power analysis using an alpha of 0.05, power of 0.8, and standard deviations based on preliminary data described in this proposal. These studies can be repeated using two different donors and repeated per donor. For the time-lapse fiber deformation studies, a minimum of 10 fibers per image can be analyzed and averaged. One way and two way ANOVAs can be performed to test for statistical differences between groups at each time point and over time, respectively for p<0.05. The Tukey-Kramer Method, p<0.05, can be used to perform multiple comparisons between groups.

REFERENCES FOR EXAMPLE 8

(1) Murphy M, Fink D J, Hunziker E B, Barry F P. Stem cell therapy in a caprine model of osteoarthritis. Arthritis Rheumatism 2003; 48:3464-74.

(2) Ponticiello M S, Schinagl R M, Kadiyala S, Barry F P. Gelatin-based resorbable sponge as a carrier matrix for human mesenchymal stem cells in cartilage regeneration therapy. J Biomed Mat Res 2000; 52:246-55.

(3) Xie L, Spradling A C. A niche maintaining germ line stem cells in the Drosophila ovary. Science 2000; 290(5490):328.

(4) Fuchs E, Segre J. Stem cells: a new lease on life. Cell 2000; 100:143-55.

(5) Watt F M, Hogan B L M. Out of eden: stem cells and their niches. Science 2000; 287(5457):1427.

(6) Praemer A, Furner S, Rice D P. Musculoskeletal conditions in the United States.: American Academy of Orthopaedic Surgeons; 1999 p. 34-9.

(7) Magnussen R A, Dunn W R, Carey J L, Spindler K P. Treatment of focal articular cartilage defects in the knee: a systematic review. Clinical Orthopaedics and Related Research 2008; 466(4):952-62.

(8) Browne J E, Anderson A F, Arciero R, Mandelbaum B, Moseley J B, Micheli L J, et al. Clinical outcome of autologous chondrocyte implantation at 5 years in US subjects. Clinical Orthopaedics and Related Research 2005; 436:237-45.

(9) Frosch K H, Drengk A, Krause P, Viereck V, Miosge N, Werner C, et al. Stem cell coated titanium implants for the partial joint resurfacing of the knee. Biomaterials 2006; 27:2542-9.

(10) Radin E L, Rose R M. Role of subchondral bone in the initiation and progression of cartilage damage. Clinical Orthopaedics 1986; 213:34-40.

(11) Kuo C K, Li W J, Mauck R L, Tuan R S. Cartilage tissue engineering: its potential and uses. Current Opinion in Rheumatology 2006; 18(1):64-73.

(12) Kang S W, Jeon O, Kim B S. Poly(lactic-co-glycolic acid) microspheres as an injectable scaffold for cartilage tissue engineering. Tissue Engineering 2005; 11(3-4):438-47.

(13) Dozin B, Malpeli M, Camardella L, Cancedda R, Pietrangelo A. Response of young, aged and osteoarthritic human articular chondrocytes to inflammatory cytokines: molecular and cellular aspects. Matrix Biology 2002; 21(5):449-59.

(14) Clar C, Cummins E, McIntyre L, Thomas S, Lamb J, Bain L, et al. Clinical and cost-effectiveness of autologous chondrocyte implantation for cartilage defects in knee joints: systematic review and economic evaluation. Health Technology Assessment 2005; 9(47):1-82.

(15) Pittenger M F, Mackay A M, Beck S C, Jaiswal R K, Douglas R, Mosca J D, et al. Multilineage potential of adult human mesenchymal stem cells. Science 1999; 284:143-7.

(16) Friedenstein A, Chailakhyan R, Gerasimov U V. Bone Marrow Osteogenic Stem Cells: In Vitro Cultivation and Transplantation in Diffusion Chambers. Cell Tissue Kinet 1987; 20(3):263-72.

(17) Haynesworth S, Baber M, Caplan A. Cell Surface Antigens on Human Marrow-Derived Mesenchymal Stem Cells are Detected by Monoclonal Antibodies. J Cell Physiol 1992; 138:8-16.

(18) Jaiswal N, Haynesworth S E, Caplan A I, Bruder S P. Osteogenic differentiation of purified culture-expanded human mesenchymal stem cells in vitro. J Cell Biochem 1997; 64:295-312.

(19) Kadiyala S, Jaiswal N, Bruder S P. Culture-expanded, bone marrow-derived mesenchymal stem cells can regenerate a critical-sized segmental bone defect. Tissue Engineering 1997; 3(2):173-85.

(20) Rickard D J, Sullivan T A, Shenker B J, Leboy P S, Kazhdan I. Induction of rapid osteoblast differentiation in rat bone marrow stromal cell cultures by dexamethason and BMP-2. Dev Bio 1994; 161:218-28.

(21) Livingston T L, Peter S P, Archambault M, Van Den Bos C, Gorden S, Kraus K, et al. Allogeneic stem cells regenerate a critically-sized canine segmental gap. Journal of Bone and Joint Surgery American 2003; 85-A(10): 1927-35.

(22) DeLise A M, Fischer L, Tuan R S. Cellular interadctions and signaling in cartilage development. Osteoarthritis and Cartilage 2000; 8:309-34.

(23) Safronova E E, Borisova N V, Mezentseva S V, Krasnopol'skaya K D. ZCharacteristics of the macromolecular components of the extracellular matrix in human hyaline cartilage at different stages of ontogenesis. Biomedical Science 1991; 2:162-8.

(24) Fukada E. Piezoelectricity and pyroelectricity of biopolymers. In: Nalwa H S, editor. Ferroelectric polymers, chemistry, physics and application. New York: Marcel Dekker, Inc.; 1995. p. 393.

(25) Wang N, Tolic-Norrelykke I M, Chen J, Mijailovich S M, Butler J P, Fredberg J J, et al. Cell prestress. I. Stiffness and prestress are closely associated in adherent contractile cells. American Journal of Physiology and Cell Physiology 2002; 282:C606-C616.

(26) Burridge K, Fath K, Kelly T, Nuckolls G, Turner C. Transmembrane junctions between extracellular matrix and the cytoskeleton. Annual Review of Cell Biology 1988; 4:487-525.

(27) Clark E A, Brugge J S. Integrins and signal transduction pathways: the road taken. Science 1995; 268:233-9.

(28) Schwartz M A, Schaller M D, Ginsberg M H. Integrins: emerging paradigms of sinal transduction. Annual Review of Cell Development Biology 1995; 11:549-99.

(29) Engler A J, Sen S, Sweeney H L, Discher D E. Matrix elasticity directs stem cell lineage specification. Cell 2006; 126:677-89.

(30) Kotwal A, Schmidt C E. Electrical stimulation alters protein adsorption and nerve cell interactions with electrically conducting biomaterials. Biomaterials 2001; 22(10):1055-64.

(31) Moreira P L, An Y H, Santos A R, Genari S C. In vitro analysis of anionic collagen scaffolds for bone repair. Journal of Biomedical Materials Research Part B: Applied Biomaterials 2004; 71(2):229-37.

(32) Bouaziz A, Richert A, Caprani A. Vascular endothelial cell responses to different electrically charged poly(vinlidene fluoride) supports under static and oscillating flow conditions. Biomaterials 1997; 18:107-12.

(33) Wang W, Wang Z, Zhang G, Clark C, Brighton C. Upregulation of chondrocyte matrix genes and products by electric fields. Clinical Orthopaedics and Related Research 2004; 427S:S163-S173.

(34) Haddad J B, Obolensky A G, Shinnick P. The biologic effects and the therapeutic mechanism of action of electric and electromagnetic field stimulation on bone and cartilage: new finds and a review of earlier work. Journal of Alternative and Complementary Medicine 2007; 13(5): 485-90.

(35) Urban E, King M W. Way to make monofilament sutures out of polyvinylidene fluoride. ASAIO J 1994; 40:145-56.

(36) Laroche G, Marois Y, Guidon R, King M W, Martin L, How T, et al. Polyvinylidene fluoride (PVDF) as a biomaterial: from polymeric raw material to mnofilament vascular suture. J Biomed Mat Res 1995; 29:1525-36.

(37) Mary C, Marois Y, King M W, Laroche G, Douville Y, Martin L, et al. Comparison of the in vivo behavior of polyvinylidene fluoride sand polypropylene sutures used in vascular surgery. ASAIO J 1998; 44:199-206.

(38) Lovinger A J. Ferroelectric polymers. Science 1983; 220:1115-21.

(39) Eberle G, Schmidt H, Eisenmenger W. Piezoelectric Polymer Electrets. IEEE Transactions on Dielectrics and Electrical Insulation 1996; 3:624-46.

(40) Valentini R F, Vargo T G, Gardella J A, Aebischer P. Electrically charged polymeric substrates enhance nerve fibre outgrowth in vitro. Biomaterials 1992; 13(3):183-90.

(41) Fine E G, Valentini R F, Bellamkonda R, Aebischer P. Improved nerve regeneration through piezoelectric vinylidenefluoride-trifluoroethylene copolymer guidance channels. Biomaterials 1991; 12:775-80.

(42) Charlton D C, Peterson M G E, Spiller K, Lowman A, Torzilli P A, Maher S A. Semi-degradable scaffold for articular cartilage replacement. Tissue Engineering Part A 2008; 14(1):207-13.

(43) Ramaswamy S, Wang D A, Fishbein K W, Elisseeff J, Spencer R G. An analysis of the integration between articular cartilage and nondegradable hydrogel using magnetic resonance imaging. Journal of Biomedical Materials Research Part B: Applied Bio materials 2006; 77B(1):144-8.

(44) Livingston T, Ducheyne P, Garino J. An in vivo evaluation of a bioactive ceramic scaffold for bone tissue engineering. J Biomed Mat Res 2002; 62:1-13.

(45) Livingston Arinzeh, T., Peter S, Archambault M, Van Den Bos C, Gordon S, et al. Allogeneic mesenchymal stem cells regenerate bone in a critical-sized canine segmental defect. Journal of Bone and Joint Surgery American 2003; 85-A(10):1927-35.

(46) Shanmugasundaram S, Mautone A, Jaffe M, Rizo L, Livingston Arinzeh T. The Effect of Varying the Architecture of Scaffolds on Mesenchymal Stem Cell Osteogenesis and Chondrogenesis. Transactions of the 2006 Annual Meeting of the Society for Bio materials. 2006.

(47) Livingston Arinzeh T, Shanmugasundaram S, Jaffe M, inventors; Substrate Recognition by Differentiable Human Mesenchymal Stem Cells. USA patent 2005.

(48) Patlolla A, Collins G, Livingston Arinzeh T. Solvent-dependent properties of electrospun fibrous composites for bone tissue regeneration. Acta Biomaterialia. In press 2009.

(49) Arinzeh T, Weber N, Jaffe M, inventors; Electrospun electroactive polymer for regenerative medicine applications. 2008.

(50) Temple M M, Bae W C, Chen M Q, Lotz M, Amiel D, Coutts R D, et al. Age- and site-associate biomechanical weakening of human articular cartilage of the femoral condyle. Osteoarthritis and Cartilage 2007; 15:1042-52.

(51) Laxminarayana K, Jalili N. Functional nanotube-based textiles: pathway to next generation fabrics with enhanced sensing capabilities. Journal of Textile Research 2005; 75(9):670-80.

(52) Aaron R K, Boyan B D, Ciombor D M, Schwartz Z, Simon B J. Stimulation of growth factor synthesis by electric and electromagnetic fields. Clinical Orthopaedics 2004; 419(30):37.

(53) Karlsson C, Brantsing C, Svensson T, Brisby H, Asp J, Tallheden T, et al. Differentiation of human mesenchymal stem cells and articular chondrocytes: analysis of chondrogenic potential and expression pattern of differentiation-related transcription factors. Journal of Orthopaedic Research 2007; 25:152-63.

(54) Andrew J S, Clarke D R. Effect of electro spinning on the ferroelectric phase of polyvinylidene difluoride fibers. Langmuir 2008; 24(3):670-2.

(55) Christie M C, Scheinbeim J I, Newman B A. Ferroelectric and piezoelectric properties of a quenched poly(vinylidene fluoride-trifluoroethylene) copolymer. Journal of Polymer Science: Part B: Polymer Physics 1997; 35:2671-9.

(56) Jolandan M M, Yu M F. Nanoscale characterization of isolated individual type I collagen fibrils: polarization and piezoelectricity. Nanotechnology 2009; 20:1-6.

(57) Wang Z, Hu J, Suryavanshi A P, Yum K, Yu M F. Voltage generation from individual BaTiO3 nanowires under periodic tensile mechanical load. Nanoletters 2007; 7(10):2966-9.

(58) Yang L, Van der Werf K O, Fitie C F C, Bennink M L, Dijkstra P J, Feijen J. Mechanical properties of native and cross-linked type I collagen fibrils. Biophysical Journal 2008; 94(6):2204-11.

(59) Vader D, Kabla A, Weitz D, Mahadevan L. Strain-induced alignment in collagen gels. PloS One 2009; 4(6):1-12.

(60) Bian L, Kaplun M, Williams D Y, Xu D, Ateshian G A, Hung C T. Influence of chondroitin sulfate on the biochemical, mechanical and frictional properties of cartilage explants in long-term culture. Journal of Biomechanics. In press 2008.

(61) Bruder S P, Kurth A A, Shea M, Hayes W C, Jaiswal N, Kadiyala S. Bone Regeneration by Implantation of Purified, Culture-Expanded Human Mesenchymal Stem Cells. J Orthop Res 1998; 16:155-62

(62) Mackay A M, Beck S C, Murphy J M, Barry F P, Chichester C O, Pittenger M F. Chondrogenic differentiation of cultured human mesenchymal stem cells from marrow. Tissue Engineering 1998; 4(4):415-28.

(63) Briggs T, Trieser M, Holmes P, Kohn J, Moghe P V, Livingston Arinzeh T. Osteogenic differentiation of human mesenchymal stem cells on poly(ethylene glycol)-variant biomaterials. Journal of Biomedical Materials Research: Part A 2008; Epub ahead of print.

(64) Barry F, Boynton R E, Liu B, Murphy J M. Chondrogenic differentiation of mesenchymal stem cells from bone marrow: differentiation-dependent gene expression of matrix components. Experimental Cell Research 2001; 268:189-200.

(65) Greco S J, Liu K, Rameshwar P. Functional similarities among genes regulated by oct-4 in human mesenchymal and embryonic stem cells. Stem Cells 2007; 25(12):3143-54.

(66) Shimazaki A, Wright M O, Elliot K, Salter D M, Millward-Sadler S J. Calcium/calmodulin-dependent protein kinase II in human articular chondrocytes. Biorheology 2006; 43:223-33.

(67) Mueller M B, Tuan R S. Functional characterization of hypertrophy in chondrogenesis of human mesenchymal stem cells. Arthritis and Rheumatism 2008; 58(5):1377-88.

(68) Muller P Y, Janovjak H, Miserez A R, Dobbie Z. Processing of gene expression data generated by quantitative real-time R T-PCR. Biotechniques 2002; 32(6):1372-4.

(69) Ducheyne P, Livingston T, Shapiro I, Ayyaswamy P, Gao H, Radin S. Surface modified bioactive glass particles as microcarriers in a microgravity environment. Tissue Engineering 1997; 3(3):219-29.

(70) Mauck R L, Soltz M, Wang C, Wong D, Chao P, Valhmu W, et al. Functional tissue engineering of articular cartilage through dynamic loading of chondrocyte-seeded agaros gels. Journal of Biomechanical Engineering 2000; 122:252-9.

Example 9: Repair of Osteochondral Defect In Vivo Using PVDF-TrFE Scaffold

Figure 29:
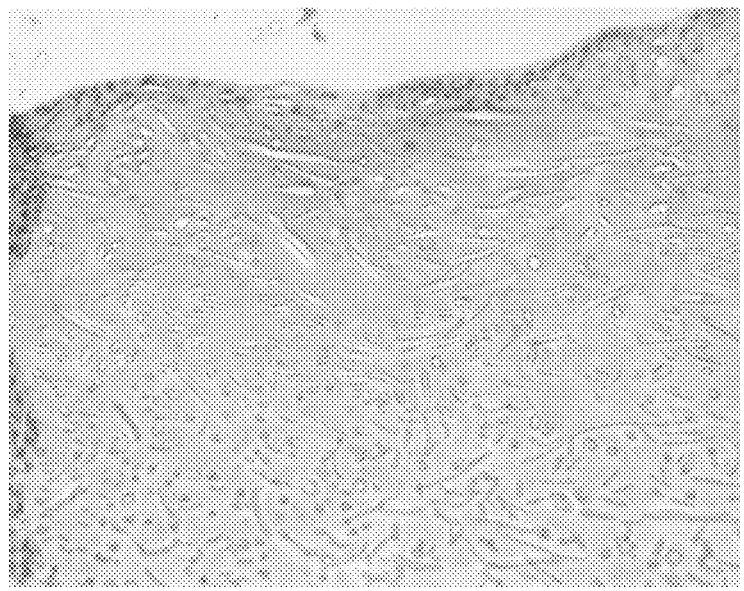
FIG. 29 demonstrates use of PVDF-TrFE scaffold for in vivo repair of osteochondral defect. Images (A)-(D) are histological images of osteochondral defects, cross-section, containing PVDF-TrFE at 12 weeks post-implantation (n=3). (A) shows an upper portion of an osteochondral defect at 20× objective, stained with H&E (hematoxylin and eosin histological stain). (B) shows the entire defect at 4× objective, stained with toluidine blue, stains for proteoglycans in purple (arrow is a processing artifact). (C) shows lower left interface, at 20× objective, stained with H&E. (D) lower right interface, at 20× objective, stained with H&E. Whitish grey areas are the scaffold. Outer surface of the defect is continuous with the native cartilage. The defect is filled with cartilage and the arrows in (C) and (D) show blood vessels and bone tissue from the subchondral area. Cartilage and bone tissue integrated and was in direct opposition with the fibers.
Figure 29:
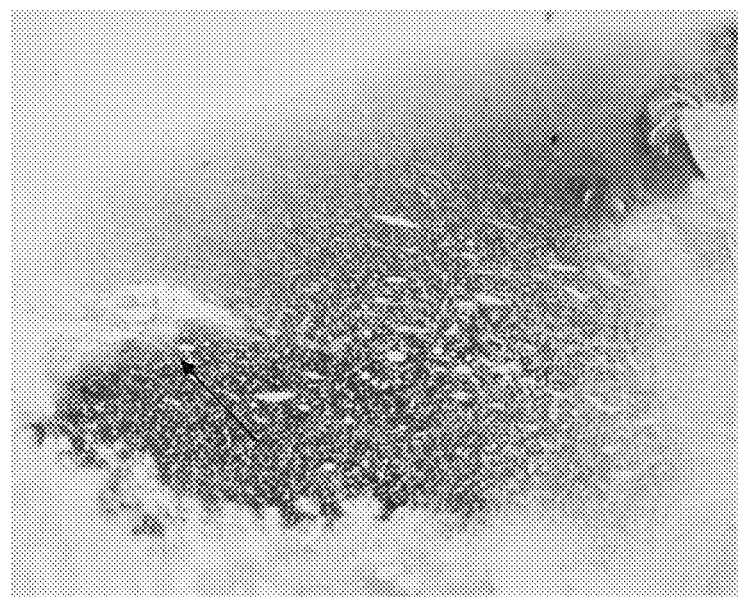
Figure 29:
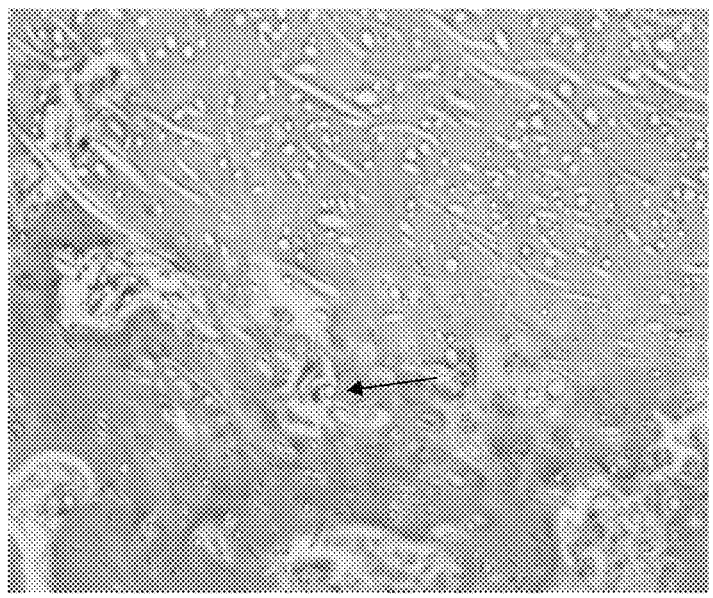
Figure 29:

The PVDF-TrFE scaffold was implanted in an osteochondral defect for 12 weeks (n=3) as a preliminary in vivo study and findings demonstrated that the scaffold was biocompatible, filled with cartilage and integrated with surrounding cartilage and bone tissue. (See FIG. 29).

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

REFERENCES

The following references are incorporated herein by reference in their entirety for all purposes.

(1) N. Zhang, H. Yan, X. Wen, "Tissue-engineering approaches for axonal guidance," *Brain Res Brain Res Rev*, vol 49, pp. 48-64, 2005.

(2) R. B. Borgens, "Electric Fields in Vertebrate Repair" in *Natural and Applied Voltage in Vertebrate Regeneration and Healing*, Wiley-Liss, 1989.

(3) N. B. Patel, M. M. Poo, "Perturbation of the direction of neurite growth by pulsed and focal electric fields," *Journal of Neurosci*, vol 4, pp 2939-47, 1984.

(4) R. Valentini, "Electrically charged polymeric substrates enhance nerve-fiber outgrowth in vitro," *Biomaterials*, vol 13, pp. 183-90, 1992.

(5) A. J. Lovinger, "Ferroelectric Polymers," *Science*, vol 220, pp 1115-21, 1983.

(6) L. H. Catalani, G. Collins, M. Jaffe, "Evidence for molecular orientation and residual charge in the electrospinning of poly (butylenes terephthalate) nanofibers," *Macromolecules*, vol 40, pp. 1693-7, 2007.

(7) Kim Y, Haftel V K, Kumar S, Bellamkonda R V. The role of aligned polymer fiber-based constructs in the bridging of long peripheral nerve gaps. Biomaterials 2008; 29(21):3117-27.

(9) Borgens R B. Electrically mediated regeneration and guidance of adult mammalian spinal axons into polymeric channels. Neuroscience 1999; 91(1):251-64.

(10) Shapiro S, Borgens R, Pascuzzi R, Roos K, Groff M, Purvines S, et al. Oscillating field stimulation for complete spinal cord injury in humans: a phase 1 trial. Journal of Neurosurgery Spine 2005; 2(1):3-10.

(11) Himes B T, Neuhuber B, Coleman C, Kushner R, Swanger S A, Kopen G C, et al. Recovery of function following grafting of human bone marrow-derived stromal cells into the injured spinal cord. Neurorehabilitation and Neural Repair 2006; 20:278-96.

(12) Cummings B J, Uchida N, Tamaki S J, Salazar D L, Hooshmand M, Summers R, et al. Human neural stem cells differentiate and promote locomoter recovery in spinal cord-injured mice. Proceedings of the National Academy of Sciences 2005; 102(39):14069-74.

(13) Cizkova D, Rosocha J, Vanicky I, Jergova S, Cizek M. Transplants of human mesenchymal stem cells improve functional recovery after spinal cord injury in the rat. Cellular and Molecular Neurobiology 2006; 26(7/8): 1167-80.

(14) N.S.C.I.A. Spinal cord injury fact sheet. Birmingham; 2001.

(15) Yannas I V. Tissue and organ regeneration in adults. Springer; 2001.

(16) Brook G A, Lawrence J M, Raisman G. Columns of Schwann cells extruded into the CNS induce in-growth of astrocytes to form organized new glial pathways. Glia 2001; 33:118-30.

(17) Oudega M, Xu X M. Schwann cell transplantation for repair of the adult spinal cord. Journal of Neurotrauma 2006; 23(3-4):453-67.

(18) Negishi H. Optic nerve regeneration within artificial Schwann cell graft in the adult rat. Brain Research Bulletin 2001; 55:409-19.

(19) Lankford K L, Sasaki M, Radtke C, Kocsis J D. Olfactory ensheathing cells exhibit unique migratory, phagocytic, and myelinating properties in the X-irradiated spinal cord not shared by Schwann cells. Glia 2008; epub ahead of print.

(20) Desawa M. Specific induction of neuronal cells from bone marrow stromal cells and application for autologous transplantation. Journal of Clinical Investigation 2004; 113:1701-10.

(21) Rosenzweig E S, McDonald J W. Rodent models for treatment of spinal cord injury: research trends and progress toward useful repair. Current Opinion in Neurology 2004; 17(2):121-31.

We claim:

1. An electroactive structure for growing and differentiating a differentiable cell comprising a three dimensional matrix of electro spun fibers; wherein
the electro spun fibers are formed by electrospinning a biocompatible synthetic piezoelectric polymer at an electric potential of between about 15 kV and about 30 kV;
wherein the electro spun fibers comprise a higher β phase content than electro spun fibers formed by electrospinning the biocompatible synthetic piezoelectric polymer at an electric potential of less than about 15 kV;
wherein the electro spun fibers are annealed, wherein annealing of the electro spun fibers further increases the β phase content and enhances piezoelectric characteristics;
wherein the matrix of electro spun fibers forms a scaffold for supporting cell growth and differentiation; and
wherein the scaffold conditions are sufficient to induce differentiation of a mesenchymal stem cell into a cell with either an osteogenic or chondrogenic phenotype.

2. The electroactive structure according to claim 1, wherein the biocompatible synthetic piezoelectric polymer is a homopolymer, a copolymer or combination thereof.

3. The electroactive structure according to claim 2, wherein the homopolymer is a polyvinylidene fluoride (PVDF) homopolymer or a trifluoroethylene homopolymer (TrFE).

4. The electroactive structure according to claim 2, wherein the copolymer is a poly(vinylidene fluoride trifluoroethylene) (PVDF-TrFE) copolymer.

5. The electroactive structure of claim 1, wherein the matrix of electrospun fibers further comprises a growth factor capable of further promoting the differentiation of the mesenchymal stem cell into a cell with osteogenic or chondrogenic phenotype.

6. The electroactive structure of claim 5, wherein the growth factor is associated with the matrix of electrospun fibers through at least one of a covalent interaction, a non-covalent interaction or a combination of both.

7. The electroactive structure according to claim 1, wherein the matrix of electrospun fibers is forms a nonwoven mesh of nanofibers, microfibers or a combination of both.

8. The electroactive structure according to claim 1, wherein the electrospun fibers are arranged in the matrix randomly, are substantially aligned or are a combination of both.

9. The electroactive structure according to claim 1, wherein the fibers are thermally or chemically annealed.

10. The electroactive structure according to claim 1, wherein the osteogenic or chondrogenic phenotype is demonstrated by at least one of increased collagen expression, growth or a combination thereof.

11. The electro active structure according to claim 1, wherein the fibers are formed by electrospinning a biocompatible synthetic piezoelectric polymer at an electric potential of about 25 kV.

12. The electro active structure according to claim 1 further comprising a mesenchymal stem cell.

13. The electro active structure according to claim 1 further comprising a cell with osteogenic or chondrogenic phenotype, wherein the cell has differentiated from a mesenchymal stem cell.

14. An electro active structure for growing and differentiating a differentiable cell comprising a three dimensional matrix of electro spun fibers; wherein
the electro spun fibers are formed by electrospinning a biocompatible synthetic piezoelectric polymer selected from the group consisting of a polyvinylidene fluoride (PVDF) homopolymer, a trifluoroethylene homopolymer (TrFE) and a poly(vinylidene fluoride trifluoroethylene) (PVDF-TrFE) copolymer at an electric potential of between about 15 kV and about 30 kV;
wherein the electro spun fibers comprise a higher β phase content than electro spun fibers formed by electrospinning the biocompatible synthetic piezoelectric polymer at an electric potential of less than about 15 kV;
wherein the electro spun fibers are annealed, wherein annealing of the electro spun fibers further increases the β phase content and enhances piezoelectric characteristics;
wherein the matrix of electro spun fibers forms a scaffold for supporting cell growth and differentiation; and wherein the scaffold conditions are sufficient to induce differentiation of a mesenchymal stem cell into either an osteogenic or chondrogenic phenotype.

* * * * *